(12) United States Patent
Seo et al.

(10) Patent No.: US 12,145,946 B2
(45) Date of Patent: Nov. 19, 2024

(54) COMPOSITION FOR EL DEVICE

(71) Applicant: SEMICONDUCTOR ENERGY LABORATORY CO., LTD., Atsugi (JP)

(72) Inventors: Satoshi Seo, Kanagawa (JP); Nobuharu Ohsawa, Kanagawa (JP); Toshiki Sasaki, Kanagawa (JP); Hiromitsu Kido, Kanagawa (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 837 days.

(21) Appl. No.: 17/287,407

(22) PCT Filed: Nov. 20, 2019

(86) PCT No.: PCT/IB2019/059953
§ 371 (c)(1),
(2) Date: Apr. 21, 2021

(87) PCT Pub. No.: WO2020/109927
PCT Pub. Date: Jun. 4, 2020

(65) Prior Publication Data
US 2021/0395271 A1 Dec. 23, 2021

(30) Foreign Application Priority Data
Nov. 30, 2018 (JP) ................................. 2018-225634

(51) Int. Cl.
| | | |
|---|---|---|
| C07D 519/00 | (2006.01) | |
| C09K 11/06 | (2006.01) | |
| H10K 50/11 | (2023.01) | |
| H10K 50/15 | (2023.01) | |
| H10K 50/16 | (2023.01) | |
| H10K 85/60 | (2023.01) | |
| H10K 101/10 | (2023.01) | |
| H10K 101/40 | (2023.01) | |

(52) U.S. Cl.
CPC ............ *C07D 519/00* (2013.01); *C09K 11/06* (2013.01); *H10K 85/657* (2023.02); *H10K 85/6576* (2023.02); *C09K 2211/1048* (2013.01); *C09K 2211/1051* (2013.01); *H10K 50/11* (2023.02); *H10K 50/15* (2023.02); *H10K 50/16* (2023.02); *H10K 2101/10* (2023.02); *H10K 2101/40* (2023.02)

(58) Field of Classification Search
CPC .. H10K 85/657; H10K 85/6576; H10K 50/15; H10K 50/16; H10K 50/11; C09K 11/06; C09K 2211/1048; C09K 2211/1051
See application file for complete search history.

(56) References Cited

U.S. PATENT DOCUMENTS

| | | |
|---|---|---|
| 9,324,949 B2 | 4/2016 | Kwong et al. |
| 9,831,437 B2 | 11/2017 | Zeng et al. |
| 9,905,782 B2 | 2/2018 | Inoue et al. |
| 10,074,806 B2 | 9/2018 | Adamovich et al. |
| 10,193,086 B2 | 1/2019 | Inoue et al. |
| 10,700,291 B2 | 6/2020 | Inoue et al. |
| 10,734,588 B2 | 8/2020 | Park et al. |
| 10,749,114 B2 | 8/2020 | Adamovich et al. |
| 11,611,042 B2 | 3/2023 | Adamovich et al. |
| 2004/0016907 A1† | 1/2004 | Shi |
| 2013/0112952 A1* | 5/2013 | Adamovich ......... H10K 85/622 252/500 |
| 2014/0291645 A1 | 10/2014 | Inoue et al. |
| 2015/0021555 A1 | 1/2015 | Kwong et al. |
| 2016/0351833 A1 | 12/2016 | Hosoumi et al. |
| 2017/0200903 A1 | 7/2017 | Park et al. |
| 2018/0166641 A1 | 6/2018 | Inoue et al. |
| 2019/0031673 A1 | 1/2019 | Yamaguchi et al. |
| 2019/0173024 A1 | 6/2019 | Inoue et al. |
| 2020/0024282 A1 | 1/2020 | Parham et al. |
| 2020/0083462 A1 | 3/2020 | Kurihara et al. |

(Continued)

FOREIGN PATENT DOCUMENTS

| | | |
|---|---|---|
| CN | 105103327 A | 11/2015 |
| CN | 106206963 A | 12/2016 |

(Continued)

OTHER PUBLICATIONS

Translation for JP 2018-127402, Aug. 16, 2018.*
Translation for JP 2018-127433, Aug. 16, 2018.*
International Search Report (Application No. PCT/IB2019/059953) Dated Jan. 28, 2020.
Written Opinion (Application No. PCT/IB2019/059953) Dated Jan. 28, 2020.
Seo.S et al., "Exciplex-triplet energy transfer: A new method to achieve extremely efficient organic light-emitting diode with external quantum efficiency over 30% and drive voltage below 3V", Jpn. J. Appl. Phys. (Japanese Journal of Applied Physics) , Mar. 17, 2014, vol. 53, No. 4, pp. 042102-1-042102-8.

*Primary Examiner* — C Melissa Koslow
(74) *Attorney, Agent, or Firm* — Fish & Richardson P.C.

(57) ABSTRACT

An object is to provide a novel composition for an EL device. Another object of one embodiment of the present invention is to provide a composition for an EL device capable of easily manufacturing an EL device with stable characteristics. Another object of one embodiment of the present invention is to provide a composition for an EL device capable of manufacturing an EL device with stable characteristics at low cost. The present inventors have studied a composition for an EL device in which different substances are mixed in advance and which does not cause change in characteristics of the EL device even when evaporation is repeated with use of the composition. As a result, a composition for an EL device in which a difference in the 5% weight loss temperature under a pressure lower than or equal to 0.1 Pa between contained substances is less than or equal to 50° C. is provided.

21 Claims, 31 Drawing Sheets

(56) References Cited

U.S. PATENT DOCUMENTS

| | | |
|---|---|---|
| 2020/0152887 A1 | 5/2020 | Yamaguchi et al. |
| 2020/0321541 A1 | 10/2020 | Hosoumi et al. |
| 2021/0013428 A1 | 1/2021 | Inoue et al. |

FOREIGN PATENT DOCUMENTS

| | | | |
|---|---|---|---|
| CN | 106573938 A | | 4/2017 |
| CN | 109305971 A | | 2/2019 |
| CN | 109608473 A | | 4/2019 |
| CN | 109616572 A | | 4/2019 |
| CN | 109651384 A | | 4/2019 |
| CN | 109689658 A | | 4/2019 |
| CN | 110073510 A | | 7/2019 |
| CN | 110382502 A | | 10/2019 |
| DE | 102018212379 | | 1/2019 |
| EP | 2849240 A | | 3/2015 |
| EP | 2866273 A | | 4/2015 |
| EP | 3425693 A | | 1/2019 |
| JP | 2014-209611 A | | 11/2014 |
| JP | 2015-021008 A | | 2/2015 |
| JP | 2015-041775 A | | 3/2015 |
| JP | 2015-097201 A | | 5/2015 |
| JP | 2016-147897 A | | 8/2016 |
| JP | 2016-174161 A | | 9/2016 |
| JP | 2016-225619 A | | 12/2016 |
| JP | 2017-098561 A | | 6/2017 |
| JP | 2017-210483 A | | 11/2017 |
| JP | 2018-110223 A | | 7/2018 |
| JP | 2018-127402 | * | 8/2018 |
| JP | 2018-127433 | * | 8/2018 |
| JP | 2018127402 A | † | 8/2018 |
| JP | 2018127433 A | † | 8/2018 |
| JP | 2018-154622 A | | 10/2018 |
| JP | 2019-085393 A | | 6/2019 |
| JP | 2019-085418 A | | 6/2019 |
| JP | 2019-090023 A | | 6/2019 |
| JP | 2019-149572 A | | 9/2019 |
| KR | 2015-0009461 A | | 1/2015 |
| KR | 2015-0132837 A | | 11/2015 |
| KR | 2015-0136942 A | | 12/2015 |
| KR | 2016-0140393 A | | 12/2016 |
| KR | 2019-0013567 A | | 2/2019 |
| KR | 2019-0059949 A | | 5/2019 |
| KR | 2019-0099508 A | | 8/2019 |
| TW | 201443058 | | 11/2014 |
| TW | 201829414 | | 8/2018 |
| TW | 201829415 | | 8/2018 |
| TW | 201831650 | | 9/2018 |
| TW | 201839095 | | 11/2018 |
| TW | 201910337 | | 3/2019 |
| WO | WO-2014/157599 | | 10/2014 |
| WO | WO-2015/182872 | | 12/2015 |
| WO | WO-2018/060307 | | 4/2018 |
| WO | WO-2018/122664 | | 7/2018 |
| WO | WO-2018/167606 | | 9/2018 |

\* cited by examiner
† cited by third party

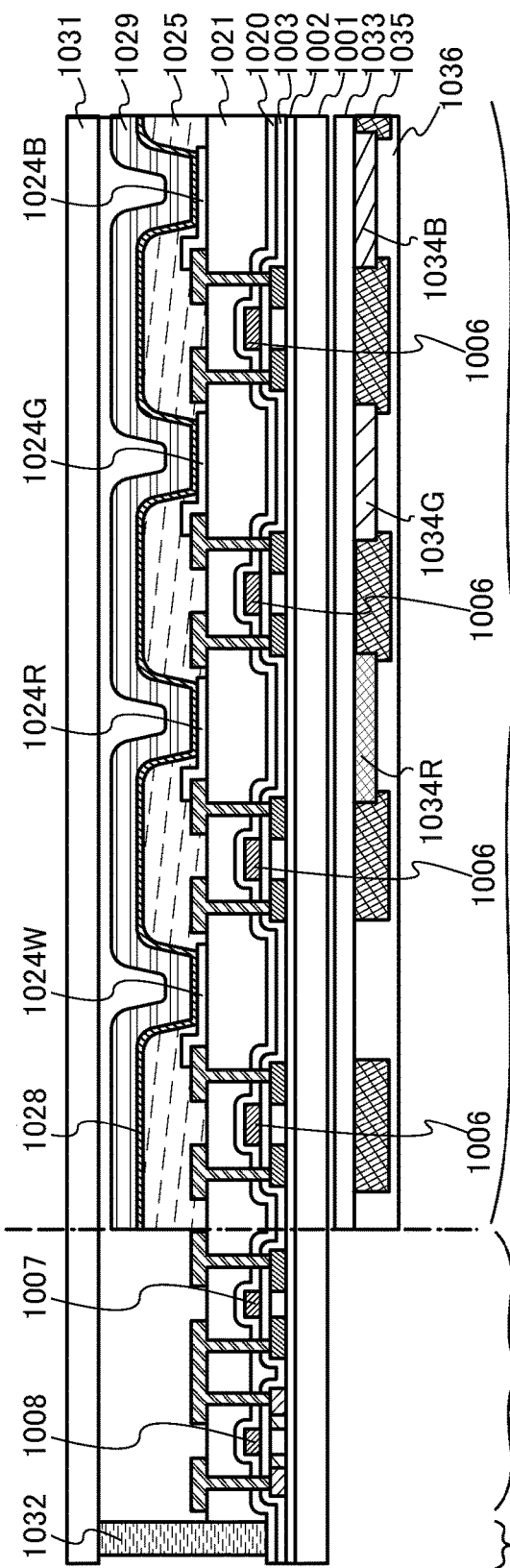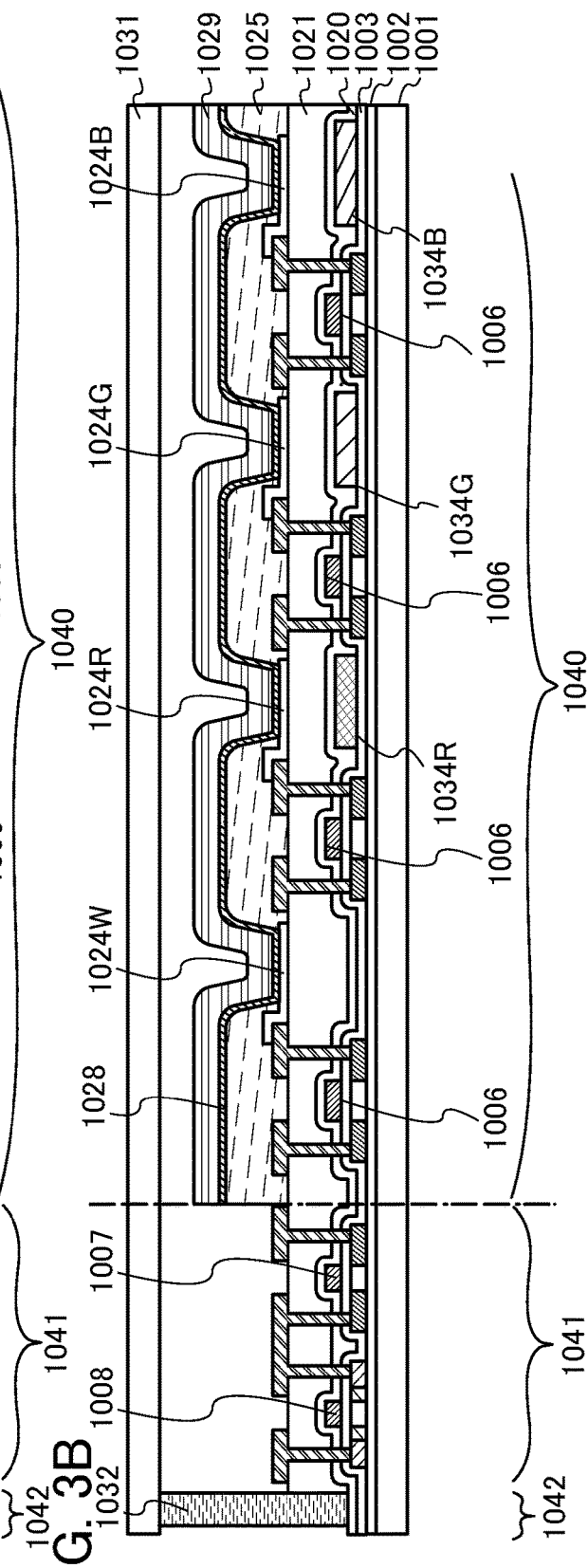
FIG. 3A
FIG. 3B

COMPOSITION FOR EL DEVICE

CROSS REFERENCE TO RELATED APPLICATIONS

This application is a U.S. National Phase Application under 35 U.S.C. § 371 of International Application PCT/IB2019/059953, filed on Nov. 20, 2019, which is incorporated by reference and claims the benefit of a foreign priority application filed in Japan on Nov. 30, 2018, as Application No. 2018-225634.

TECHNICAL FIELD

One embodiment of the present invention relates to a composition for an EL device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting apparatus, a power storage device, a memory device, an imaging device, a driving method thereof, and a manufacturing method thereof.

BACKGROUND ART

EL devices (organic EL devices) including organic compounds and utilizing electroluminescence (EL) have been put into practical use. In the basic structure of such EL devices, an organic compound layer containing a light-emitting material (an EL layer) is interposed between a pair of electrodes. Carriers are injected by application of voltage to the device, and recombination energy of the carriers is used, whereby light emission can be obtained from the light-emitting material.

Such EL devices are of self-light-emitting type, and have advantages over liquid crystal, such as high visibility and no need for backlight when used for pixels of a display; accordingly, the EL devices are suitable as flat panel display element. Displays using such EL devices are also highly advantageous in that they can be fabricated thin and lightweight. Moreover, an extremely fast response speed is also a feature.

Since light-emitting layers of such EL devices can be successively formed two-dimensionally, planar light emission can be achieved. This feature is difficult to realize with point light sources typified by incandescent lamps and LEDs or linear light sources typified by fluorescent lamps; thus, the EL devices also have great potential as planar light sources, which can be applied to lighting apparatuses and the like.

Such EL devices are manufactured through a wet process typified by an ink-jet method or a dry process typified by an evaporation method, and currently, manufacturing by an evaporation method is mainstream because it facilitates increases in resolution and lifetime.

In the manufacturing of an EL device by an evaporation method, a light-emitting layer is formed by co-evaporation of at least two kinds of substances, an emission center substance and a host material. Co-evaporation refers to an evaporation method by which different substances are evaporated from different evaporation sources at the same time, and three or more kinds of substances are co-evaporated in some cases for improving the carrier balance in the light-emitting layer or other reasons.

Co-evaporation of a plurality of substances needs evaporation sources whose number is the same as the kinds of substances, which might increase the cost of an evaporation apparatus and time and effort for maintenance.

REFERENCE

Patent Document

[Non-Patent Document 1] Japanese Published Patent Application No. 2015-97201

SUMMARY OF THE INVENTION

Problems to be Solved by the Invention

An object of one embodiment of the present invention is to provide a novel composition for an EL device. Another object of one embodiment of the present invention is to provide a composition for an EL device capable of easily manufacturing an EL device with stable characteristics. Another object of one embodiment of the present invention is to provide a composition for an EL device capable of manufacturing an EL device with stable characteristics at low cost.

Note that the description of these objects does not preclude the existence of other objects. In one embodiment of the present invention, there is no need to achieve all of these objects. Other objects are apparent from and can be derived from the description of the specification, the drawings, the claims, and the like.

It is only necessary that at least one of the above-described objects be achieved in the present invention.

Means for Solving the Problems

One embodiment of the present invention is a composition for an EL device, including at least two kinds of organic compounds. A difference in the 5% weight loss temperature between the at least two kinds of organic compounds measured by thermogravimetry under a pressure of 0.1 Pa or lower is less than or equal to 50° C.

Another embodiment of the present invention is a composition for an EL device, including a first organic compound and a second organic compound. A difference in the 5% weight loss temperature between the first organic compound and the second organic compound measured by thermogravimetry under a pressure of 0.1 Pa or lower is less than or equal to 50° C.

Another embodiment of the present invention is the composition for an EL device with the above structure in which the first organic compound has an electron-transport property, and the second organic compound has a hole-transport property.

Another embodiment of the present invention is the composition for an EL device with the above structure in which the first organic compound has a benzofurodiazine skeleton or a benzothiodiazine skeleton.

Another embodiment of the present invention is the composition for an EL device with the above structure in which the first organic compound has any one of a naphthofuropyrazine skeleton, a phenanthrofuropyrazine skeleton, a naphthothiopyrazine skeleton, and a phenanthrothiopyrazine skeleton.

Another embodiment of the present invention is the composition for an EL device with the above structure in which the first organic compound is represented by General Formula (G1).

[Chemical Formula 1]

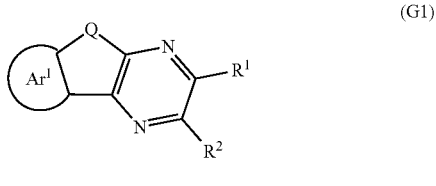

(G1)

In General Formula (G1) above, Q represents oxygen or sulfur. Furthermore, Ar¹ represents a substituted or unsubstituted condensed aromatic ring. One of $R^1$ and $R^2$ represents hydrogen and the other represents a group having a hole-transport property skeleton and 1 to 100 carbon atoms in total.

Another embodiment of the present invention is the composition for an EL device with the above structure in which the first organic compound is represented by Structural Formula (100) below.

[Chemical Formula 2]

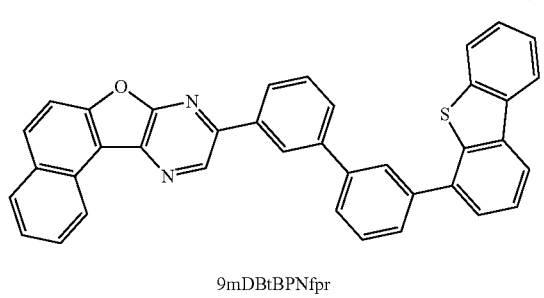

(100)

9mDBtBPNfpr

Another embodiment of the present invention is the composition for an EL device with the above structure in which the first organic compound has a benzofuropyrimidine skeleton or a benzothiopyrimidine skeleton.

Another embodiment of the present invention is the composition for an EL device with the above structure in which the first organic compound is represented by General Formula (G2).

[Chemical Formula 3]

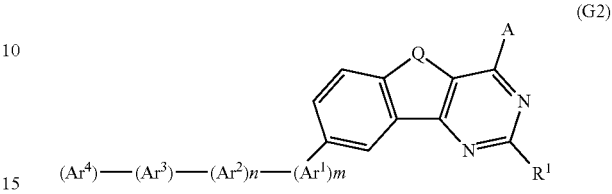

(G2)

In the formula, Q represents oxygen or sulfur. Each of $Ar^1$, $Ar^2$, $Ar^3$, and $Ar^4$ independently represents a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is greater than or equal to 6 and less than or equal to 25. In addition, each of m and n independently represents 0 or 1. Moreover, A represents a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

Another embodiment of the present invention is the composition for an EL device with the above structure in which the first organic compound is represented by Structural Formula (200) or Structural Formula (201) below.

[Chemical Formula 4]

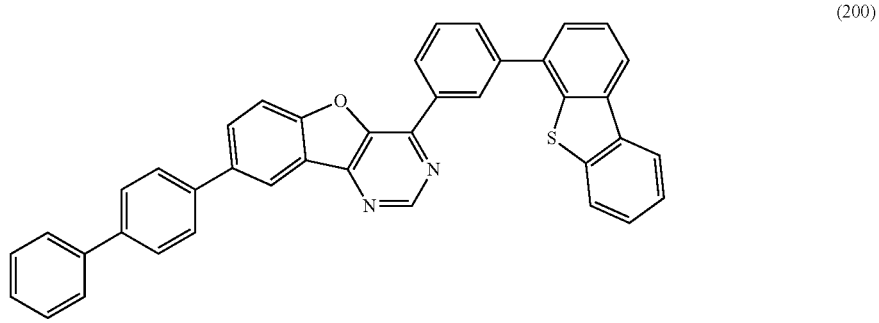

(200)

8BP-4mDBtPBfpm

-continued

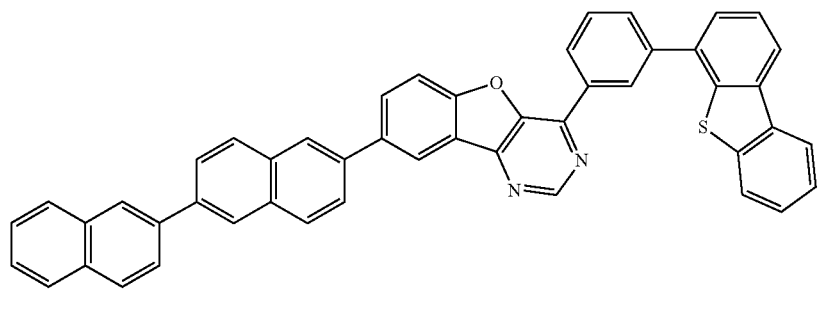

(201)

8(βN2)-4mDBtPBfpm

Another embodiment of the present invention is the composition for an EL device with the above structure in which the second organic compound has an aromatic amine skeleton.

Another embodiment of the present invention is the composition for an EL device with the above structure in which the second organic compound has a carbazole skeleton.

Another embodiment of the present invention is the composition for an EL device with the above structure in which the second organic compound has a triarylamine skeleton.

Another embodiment of the present invention is the composition for an EL device with the above structure in which the second organic compound has a bicarbazole skeleton.

Another embodiment of the present invention is the composition for an EL device with the above structure in which two carbazolyl groups in the bicarbazole skeleton are bonded to each other at any of the 2-position to the 4-position.

Another embodiment of the present invention is the composition for an EL device with the above structure in which the second organic compound has a triarylamine skeleton and a carbazole skeleton.

Another embodiment of the present invention is the composition for an EL device with the above structure in which a nitrogen atom in the triarylamine and the carbazole skeleton are bonded through a phenylene group.

Another embodiment of the present invention is the composition for an EL device with the above structure in which the carbazole skeleton is bonded at any one of the 2-position, the 3-position, the 4-position, and the 9-position.

Another embodiment of the present invention is the composition for an EL device with the above structure in which the second organic compound has at least one fluorene skeleton.

Another embodiment of the present invention is the composition for an EL device with the above structure in which the first organic compound and the second organic compound are a combination that forms an exciplex.

Another embodiment of the present invention is the composition for an EL device with the above structure in which the difference in the 5% weight loss temperature is less than or equal to 40° C.

Another embodiment of the present invention is the composition for an EL device with the above structure in which the difference in the 5% weight loss temperature is less than or equal to 30° C.

Note that the light-emitting apparatus in this specification includes, in its category, an image display device that uses an EL device. The light-emitting apparatus may also include a module in which an EL device is provided with a connector such as an anisotropic conductive film or a TCP (Tape Carrier Package), a module in which a printed wiring board is provided at the end of a TCP, and a module in which an IC (integrated circuit) is directly mounted on an EL device by a COG (Chip On Glass) method. Furthermore, in some cases, a lighting device or the like includes the light-emitting apparatus.

Effect of the Invention

One embodiment of the present invention can provide a novel composition for an EL device. Another embodiment of the present invention can provide a composition for an EL device capable of easily manufacturing an EL device with stable characteristics. Another embodiment of the present invention can provide a composition for an EL device capable of manufacturing an EL device with stable characteristics at low cost.

Note that the description of the effects does not preclude the existence of other effects. Note that one embodiment of the present invention does not need to have all these effects. Note that effects other than these will be apparent from the description of the specification, the drawings, the claims, and the like and effects other than these can be derived from the description of the specification, the drawings, the claims, and the like.

BRIEF DESCRIPTION OF THE DRAWINGS

FIG. 3A and FIG. 3B are conceptual diagrams of an active matrix light-emitting apparatus.
FIG. 7A, FIG. 7B1, FIG. 7B2, and FIG. 7C are diagrams illustrating electronic devices.

MODE FOR CARRYING OUT THE INVENTION

Figure 1A:
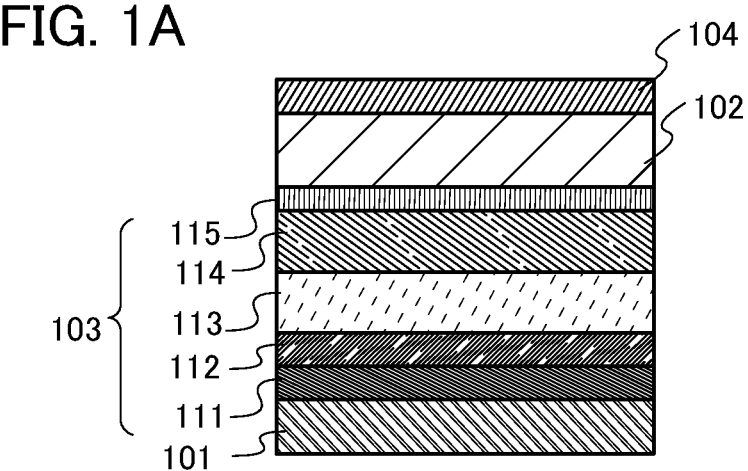
FIG. 1A to FIG. 1C are schematic diagrams of EL devices.

Embodiments of the present invention are described in detail below with reference to drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Embodiment 1

A general organic EL device is formed to include an EL layer containing an organic compound between a pair of electrodes. The EL layer has a stacked structure of layers having different functions. The stacked structure is composed of, for example, functional layers such as a carrier-blocking layer and a charge-generation layer, in addition to a hole-injection layer 111, a hole-transport layer 112, a light-emitting layer 113, an electron-transport layer 114, and an electron-injection layer 115 which are included in an EL layer 103 illustrated in FIG. TA.

Some functional layers may be a layer containing a single substance and some functional layers may be a layer in which a plurality of substances are mixed. In particular, the light-emitting layer 113 often has a host-guest type structure for the purpose of inhibiting a quenching phenomenon due to interference between excitons or adjusting the position of a light-emitting region.

In general, in manufacturing of an organic EL device through a dry process, in order to obtain a light-emitting device in which two or more different substances exist in one layer in a uniformly mixed state, a co-evaporation method using different evaporation sources for the respective substances is selected. This is because, since the substances have different sublimation temperatures and different evaporation temperatures, temperatures of the evaporation sources need to be adjusted to be suitable for the respective substances and required evaporation rates.

However, in this method, an evaporation source is prepared for each kind of materials, which causes disadvantages, such as an increase in investment amount for an apparatus and dependence of the number of substances to be mixed on the apparatus.

On the other hand, in order to obtain a more efficient EL device with a longer lifetime, the structure of the light-emitting layer 113 has been further developed from the above-described host-guest type, and a structure composed of three or more substances, such as host, assist, guest, and the like has been put into practical use.

As described above, the kinds of substances that can be mixed in one light-emitting layer depend on the number of evaporation sources of the apparatus, and an increase in evaporation sources needs a certain degree of investment.

Figure 14A:
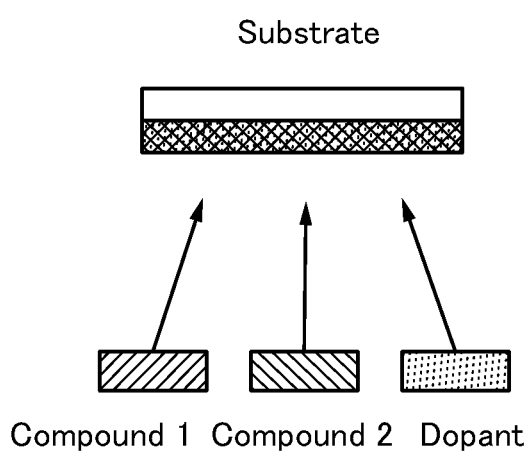
FIG. 14A and FIG. 14B are schematic diagrams of evaporation apparatuses.
Figure 14B:
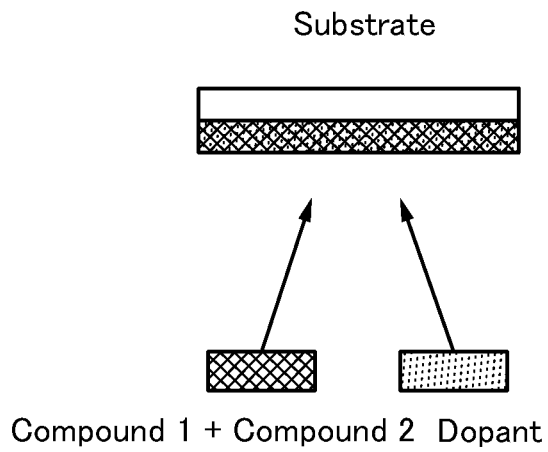

Here, considered is a method in which a plurality of substances are mixed in advance and are evaporated from one evaporation source so that substances whose number is greater than or equal to the number of evaporation sources are deposited. FIG. 14 is a schematic diagram illustrating formation of a mixed layer of three kinds of substances (a compound 1, a compound 2, and a dopant) by evaporation. FIG. 14A illustrates the case where the three kinds of substances are evaporated from different evaporation sources, in which case three evaporation sources are needed. On the other hand, FIG. 14B illustrates the case where a composition in which two kinds of substances (the compound 1 and the compound 2) are mixed in advance is evaporated from one evaporation source, in which case only two evaporation sources are needed for evaporation of three kinds of substances. However, since substances have inherent evaporation temperatures and sublimation temperatures, it is difficult to form a layer with a desired thickness and a desired composition even with use of a material mixed in advance.

In addition, in order to release a large number of commercialized products, the method is required to provide EL devices having characteristics which do not change even when a plurality of devices are manufactured using the same evaporation source successively.

As described above, substances have inherent values of evaporation temperatures and sublimation temperatures. In the case where a plurality of substances are mixed and evaporated from one evaporation source, a larger amount of substances with lower temperatures might be scattered, which might gradually change the composition of substances inside the evaporation source. When the composition of the sample inside the evaporation source is changed, the composition of a film is changed by each repetition of evaporation; as a result, characteristics of the EL device are changed.

In view of the above, the present inventors have studied a composition for an EL device in which different substances are mixed in advance and which does not cause change in characteristics of the EL device even when evaporation is repeated with use of the composition. As a result, the inventors found that a composition for an EL device in which a difference in the 5% weight loss temperature under a pressure lower than or equal to 0.1 Pa between contained substances is less than or equal to 50° C. is less likely to cause composition change even when evaporation is repeated and that an EL device manufactured with use of the composition is less likely to change its characteristics largely.

That is, one embodiment of the present invention is a composition for an EL device, including at least two kinds of organic compounds. A difference in the 5% weight loss temperature between the at least two kinds of organic compounds measured by thermogravimetry under a pressure of 0.1 Pa or lower is less than or equal to 50° C.

The 5% weight loss temperature can be obtained from the relation between weight and temperature (thermogravimetric measurement) by performing thermogravimetry-differential thermal analysis (TG-DTA). Note that considering that the evaporation is performed at a pressure of 0.1 Pa or lower, the measurement is preferably performed under an atmosphere of lower than or equal to 0.1 Pa. In the case where the pressure for the evaporation is determined in advance, it is preferable to use a value measured under the pressure.

With use of a sample formed with a composition in which a difference in the 5% weight loss temperature measured in such a manner between mixed materials is less than or equal to 50° C., the composition change is small even when evaporation is repeated; thus, EL devices with favorable characteristics can be stably manufactured. Note that the difference in the 5% weight loss temperature is preferably less than or equal to 40° C., further preferably less than or equal to 30° C., still further preferably less than or equal to 20° C.

In the case where the composition for an EL device of one embodiment of the present invention is composed of two kinds of substances, a first organic compound and a second organic compound, it is preferable that the first organic compound have an electron-transport property and the second organic compound have a hole-transport property. In this case, the composition for an EL device is useful as a composition for forming the light-emitting layer 113 in an EL device. In the case where the first organic compound and the second organic compound are a combination that forms an exciplex, the composition for an EL device is more useful as the composition for forming the light-emitting layer 113. The mixture ratio of the first organic compound to the second organic compound is preferably 1:9 to 9:1, and further preferably 2:8 to 8:2 in a weight ratio.

When the first organic compound is a material having a hole-transport property and the second organic compound is a substance exhibiting an electron-accepting property to the first organic compound, the composition for an EL device is useful as a composition for forming the hole-injection layer 111. When the first organic compound is a material having an electron-transport property and the second organic compound is a substance exhibiting an electron-donating property to the first organic compound, the composition for an EL device is useful as a composition for forming the electron-transport layer 114.

Note that in the case where the first organic compound has an electron-transport property and the second organic compound has a hole-transport property, it is effective that the first organic compound has a benzofurodiazine skeleton or a benzothiodiazine skeleton in order to manufacture a more stable EL device. In that case, the first organic compound is preferably any of a naphthofuropyrazine skeleton, a phenanthrofuropyrazine skeleton, a naphthothiopyrazine skeleton, and a phenanthrothiopyrazine skeleton, and is further preferably an organic compound represented by General Formula (G1) below. In that case, the composition for an EL device is useful as a composition for forming the light-emitting layer 113 in an EL device.

[Chemical Formula 5]

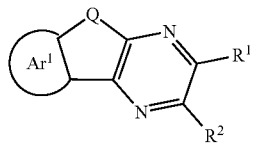

(G1)

In General Formula (G1) above, Q represents oxygen or sulfur. Furthermore, $Ar^1$ represents a substituted or unsubstituted condensed aromatic ring. One of $R^1$ and $R^2$ represents hydrogen and the other represents a group having a hole-transport-property skeleton and 1 to 100 carbon atoms in total. As examples of the hole-transport-property skeleton, a π-electron rich heteroaromatic ring skeleton, such as a pyrrole skeleton, a furan skeleton, a thiophene skeleton, or a carbazole skeleton, a condensed aromatic hydrocarbon ring skeleton, and an aromatic amine skeleton can be given.

Another embodiment of the present invention is the composition for an EL device with the above structure in which the first organic compound is represented by Structural Formula (100) below.

[Chemical Formula 6]

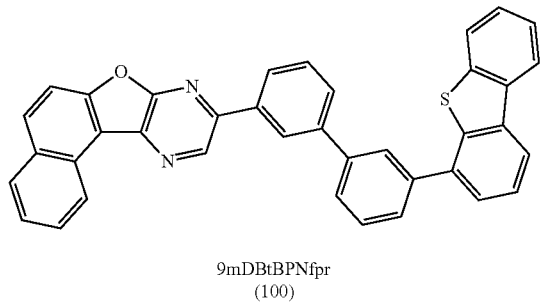

9mDBtBPNfpr
(100)

In the case where the first organic compound has an electron-transport property and the second organic compound has a hole-transport property, the first organic compound preferably has a benzofuropyrimidine skeleton or a benzothiopyrimidine skeleton in order to manufacture a more stable EL device, and further preferably, the first organic compound is an organic compound represented by General Formula (G2) below.

[Chemical Formula 7]

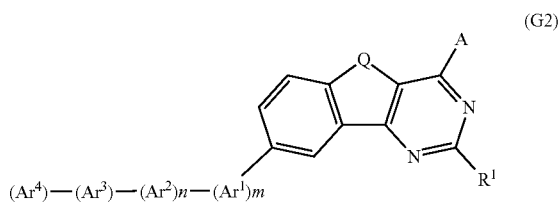

(G2)

In the formula, Q represents oxygen or sulfur. Each of $Ar^1$, $Ar^2$, $Ar^3$, and $Ar^4$ independently represents a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is greater than or equal to 6 and less than or equal to 25. In addition, each of m and n independently represents 0 or 1. Moreover, A represents a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms. Note that in General Formula (G2) above, m and n preferably represent 0.

Another embodiment of the present invention is the composition for an EL device with the above structure in which the first organic compound is represented by Structural Formula (200) or Structural Formula (201) below.

[Chemical Formula 8]

(200)

8BP-4mDBtPBfpm

(201)

8(βN2)-4mDBtPBfpm

In the case where the first organic compound has an electron-transport property and the second organic compound has a hole-transport property, the second organic compound preferably has an aromatic amine skeleton, in which case a high hole-transport property and favorable stability are obtained. The second organic compound preferably has a triarylamine skeleton or a carbazole skeleton or the both of them.

Note that in the case where the second organic compound is an organic compound having both a triarylamine skeleton and a carbazole skeleton, an organic compound in which a nitrogen atom in the triarylamine skeleton and the carbazole skeleton are bonded through a phenylene group is preferred because of its stability and favorable reliability. Similarly, in the case where the second organic compound is the organic compound having both a triarylamine skeleton and a carbazole skeleton, the carbazole skeleton is preferably bonded to the amine at the 2-position to the 4-position or the 9-position in terms of reliability.

In the case where the second organic compound is an organic compound having a carbazole skeleton, the second organic compound is preferably an organic compound having a bicarbazole skeleton because of its favorable hole-transport property and high stability. In that case, the bicarbazole skeleton preferably has a structure in which two carbazolyl groups are bonded to each other at any of the 2-position to the 4-position.

Even when the composition for an EL device of one embodiment of the present invention with the above structure is evaporated successively, the composition itself or the composition of a formed film does not largely change. Therefore, an EL device manufactured using the composition for an EL device can exhibit favorable and stable characteristics.

Since a plurality of organic compounds can be evaporated from one evaporation source, EL devices with favorable characteristics can be manufactured without extra or additional capital investment. That is, EL devices with favorable characteristics can be manufactured at low cost.

Embodiment 2

In this embodiment, a specific embodiment of an EL device that can be manufactured using the composition for an EL device described in Embodiment 1 will be described. FIG. 1 illustrates the EL device that can be manufactured using the composition for an EL device described in Embodiment 1. The EL device illustrated in FIG. TA includes an anode 101, a cathode 102, and an EL layer 103.

The EL layer 103 in FIG. 1 includes functional layers such as the light-emitting layer 113, and may also include a hole-injection layer 111, a hole-transport layer 112, an electron-transport layer 114, an electron-injection layer 115, and the like in addition to the light-emitting layer. The light-emitting layer 113 includes a light-emitting material, and light is emitted from the light-emitting material in the EL device described in this embodiment. The light-emitting layer 113 may include a host material and other materials.

Next, examples of specific structures and materials of the aforementioned EL device will be described.

The anode 101 is preferably formed using any of metals, alloys, and conductive compounds with a high work function (specifically, higher than or equal to 4.0 eV), mixtures thereof, and the like. Specific examples include indium oxide-tin oxide (ITO: Indium Tin Oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 to 20 wt % of zinc oxide to indium oxide. Furthermore, indium oxide containing tungsten oxide and zinc oxide (IWZO) can be deposited by a sputtering method using a target in which tungsten oxide and zinc oxide are added to indium oxide at 0.5 to 5 wt % and 0.1 to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the anode 101 in the EL layer 103, an electrode material can be selected regardless of its work function.

Although the EL layer 103 preferably has a stacked structure, there is no particular limitation on the stacked structure, and various layer structures such as a hole-injection layer, a hole-transport layer, a light-emitting layer, an electron-transport layer, an electron-injection layer, a carrier-blocking layer, an exciton-blocking layer, and a charge-generation layer can be employed. Two kinds of structures are described in this embodiment: the structure illustrated in FIG. 1A, which includes the electron-transport layer 114 and the electron-injection layer 115 in addition to the hole-injection layer 111, the hole-transport layer 112, and the light-emitting layer 113; and the structure illustrated in FIG. 1B, which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The hole-injection layer 111 can be formed using a substance having an electron-accepting property. As examples of the substance having an electron-accepting property, molybdenum oxide, vanadium oxide, ruthenium oxide, tungsten oxide, and manganese oxide can be given. Among these, molybdenum oxide is an especially preferable substance because it is stable in the air, has a low hygroscopic property, and is easy to handle.

Other than the above-mentioned substances, organic compounds having an electron-withdrawing group (a halogen group or a cyano group) can be given. A [3]radialene derivative having an electron-withdrawing group (in particular, a cyano group or a halogen group such as a fluoro group) is an organic compound that can be suitably used as the substance having an electron-accepting property because it has a very high electron-accepting property. Examples of such organic compounds include 7,7,8,8-tetracyano-2,3,5,6-tetrafluoroquinodimethane (abbreviation: F4-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), α,α', α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile]. As an organic compound having an electron-accepting property, a compound in which an electron-withdrawing group is bonded to a condensed aromatic ring having a plurality of heteroatoms, such as HAT-CN, is preferred because it is thermally stable.

Alternatively, it is possible to use any of the following materials: phthalocyanine-based complex compounds such as phthalocyanine (abbreviation: H$_2$Pc) and copper phthalocyanine (abbreviation: CuPc); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N-diphenyl-(1,1'-biphenyl)-4,4'-diamine (abbreviation: DNTPD); and the like. Alternatively, it is also possible to use a high molecular compound, such as poly(3,4-ethylenedioxythiophene)/poly(styrenesulfonic acid) (PEDOT/PSS), or the like.

These substances having an electron-accepting property can extract electrons from an adjacent hole-transport layer (or hole-transport material) when an electric field is applied, and inject holes to (generate holes in) the adjacent hole-transport layer (or hole-transport material) by the extraction of electrons.

Alternatively, a composite material in which a substance having a hole-transport property contains a substance having an electron-accepting property can be used for the hole-injection layer 111. By using the composite material in which a substance having a hole-transport property contains a substance having an electron-accepting property, a material used to form an electrode can be selected regardless of its work function. In other words, besides a material having a high work function, a material having a low work function can also be used for the anode 101. As the substance having an electron-accepting property, the above-described substances having an electron-accepting can be used.

As the substance having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance having a hole-transport property used for the composite material preferably has a hole mobility of $10^{-6}$ cm$^2$/Vs or higher. Organic compounds which can be used as the substance having a hole-transport property in the composite material are specifically given below.

Examples of the aromatic amine compounds that can be used for the composite material include N,N'-di(p-tolyl)-N,N-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and 1,1-bis-(4-bis(4-methyl-phenyl)-amino-phenyl)-cyclohexane (abbreviation: TAPC). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N-[4-(4-diphenylamino)phenyl]phenyl-N-phenylamino}phenyl)methacrylamide] (abbreviation: PTPDMA), and poly[N,N-bis(4-butylphenyl)-N,N'-bis(phenyl)benzidine] (abbreviation: Poly-TPD).

The hole-transport layer 112 contains a material having a hole-transport property. The material having a hole-transport property preferably has a hole mobility of $1\times10^{-6}$ cm$^2$/Vs or more.

Examples of the material having a hole-transport property include compounds having an aromatic amine skeleton such as 4,4'-bis[N-(1-naphthyl)-N-phenylamino]biphenyl (abbreviation: NPB), N,N'-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property that is used in the composite material for the hole-injection layer 111 can also be suitably used as the material included in the hole-transport layer 112.

The light-emitting layer 113 is a layer containing a host material and a light-emitting material. The light-emitting material may be fluorescent substances, phosphorescent substances, substances exhibiting thermally activated delayed fluorescence (TADF), or other light-emitting materials. Furthermore, the light-emitting layer 113 may be a single layer or be formed of a plurality of layers including different light-emitting materials.

Examples of a fluorescent substance that can be used as a light-emitting material in the light-emitting layer 113 are as follows. Fluorescent substances other than those given below can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N'-bis[4-(9-phenyl-9H-fluoren-9-yl)phenyl]pyrene-1,6-diamine (abbreviation: 1,6FLPAPm), N,N'-bis(3-methylphenyl)-N,N'-bis[3-(9-phenyl-9H-fluoren-9-yl)phenyl]pyrene-1,6-diamine (abbreviation: 1,6mMemFLPAPm), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N,N-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N,N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[i/]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[i/]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and N,N'-diphenyl-N,N-(1,6-pyren-diyl)bis[(6-phenylbenzo[b]naphtho[1,2-d]furan)-8-amine] (abbreviation:1,6BnfAPrn-03). Condensed aromatic diamine compounds typified by pyrenediamine compounds such as 1,6FLPAPm, 1,6mMemFLPAPm, and 1,6BnfAPrn-03 are particularly preferable because of their high hole-trapping properties, high emission efficiency, and high reliability.

Examples of a phosphorescent substance that can be used as a light-emitting material in the light-emitting layer 113 are as follows.

The examples are as follows: an organometallic iridium complex having a 4H-triazole skeleton, such as tris{2-[5-(2-methylphenyl)-4-(2,6-dimethylphenyl)-4H-1,2,4-triazol-3-yl-xN2]phenyl-xC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium (III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptzl-mp)$_3$]) and tris(1-methyl-5-phenyl-3-propyl-1H-1,2,4-triazolato)iridium (III) (abbreviation: [Ir(Prptzl-Me)$_3$]); an organometallic iridium complex having an imidazole skeleton, such as fac-tris[1-(2,6-diisopropylphenyl)-2-phenyl-TH-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C2']iridium (III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF$_3$ppy)$_2$(pic)]), and bis[2-(4',6'-difluorophenyl)pyridinato-N,$C^{2'}$]iridium(III) acetylacetonate (abbreviation: FIr(acac)). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato] iridium(III) (abbreviation: [Ir(5mdppm)$_2$(dibm)]), bis[4,6-bis(3-methylphenyl)pyrimidinato](dipivaloylmethanato) iridium(III) (abbreviation: [Ir(5mdppm)$_2$(dpm)]), and bis[4,6-di(naphthalen-1-yl)pyrimidinato(dipivaloylmethanato) iridium(III) (abbreviation: [Ir(dlnpm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: PtOEP); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato(monophenanthroline)europium(III) (abbreviation: [Eu(TTA)$_3$(Phen)]). These compounds emit red phosphorescence and have an emission peak at 600 nm to 700 nm. Furthermore, the organometallic iridium complexes having a pyrazine skeleton can provide red light emission with favorable chromaticity.

Besides the above-described phosphorescent compounds, other known phosphorescent materials may be selected and used.

Examples of the TADF material that can be used in the light-emitting layer 113 include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.

[Chemical Formula 9]

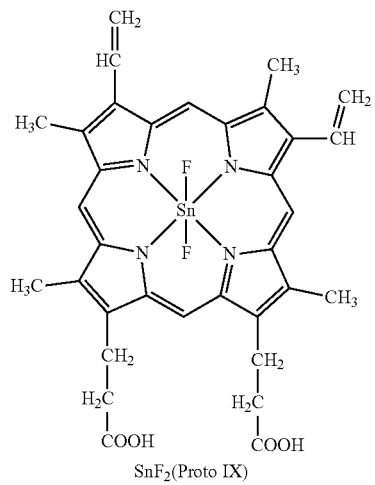

SnF$_2$(Proto IX)

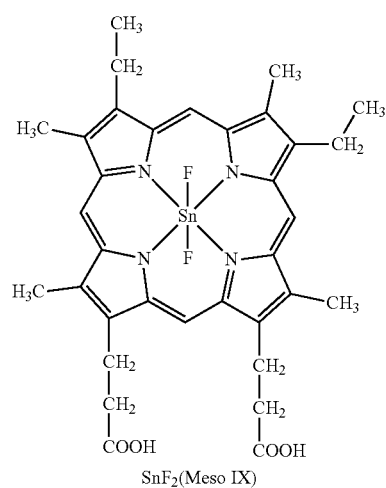

SnF$_2$(Meso IX)

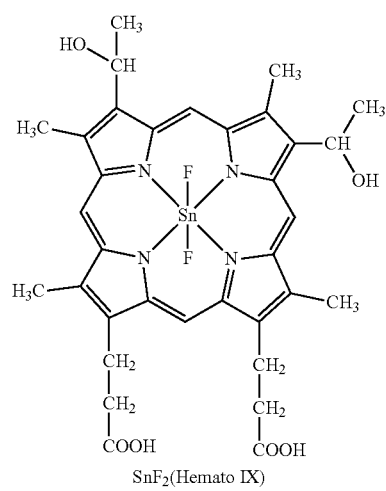

SnF$_2$(Hemato IX)

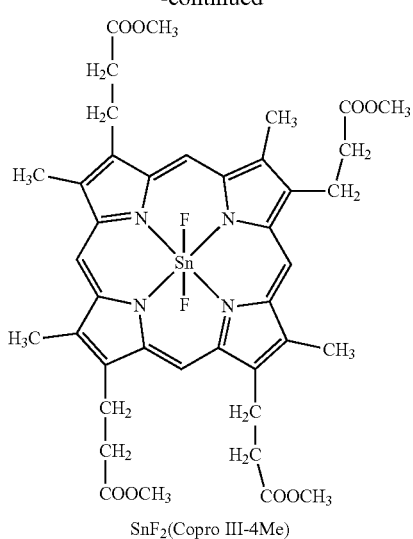

SnF₂(Copro III-4Me)

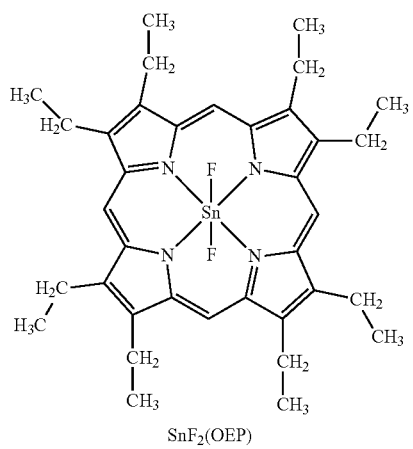

SnF₂(OEP)

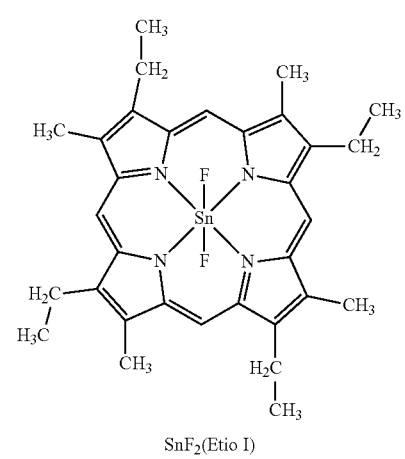

SnF₂(Etio I)

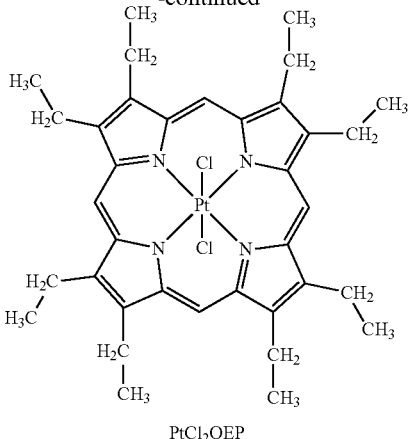

PtCl₂OEP

Alternatively, a heterocyclic compound having one of both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. The heterocyclic compound is preferable because of having both a high electron-transport property and a high hole-transport property owing to a π-electron rich heteroaromatic ring and a π-electron deficient heteroaromatic ring. Among skeletons having a π-electron deficient heteroaromatic ring, a pyridine skeleton, a diazine skeleton (a pyrimidine skeleton, a pyrazine skeleton, or a pyridazine skeleton) and a triazine skeleton are particularly preferable because of their high stability and reliability. In particular, a benzofuropyrimidine skeleton, a benzothienopyrimidine skeleton, a benzofuropyrazine skeleton, and a benzothienopyrazine skeleton are preferable because of their high acceptor property and reliability. Among skeletons having a π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. Note that a dibenzofuran skeleton and a dibenzothiophene skeleton are preferable as the furan skeleton and the thiophene skeleton, respectively. As the pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which a π-electron rich heteroaromatic ring and a π-electron deficient heteroaromatic ring are directly bonded to each other is particularly preferable because the electron-donating property of the π-electron rich heteroaromatic ring and the electron-accepting property of the π-electron deficient heteroaromatic ring are both increased and the energy difference between the $S_1$ level and the $T_1$ level becomes small, so that thermally activated delayed fluorescence can be obtained efficiently. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group such as benzonitrile or a cyano group such as cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 10]

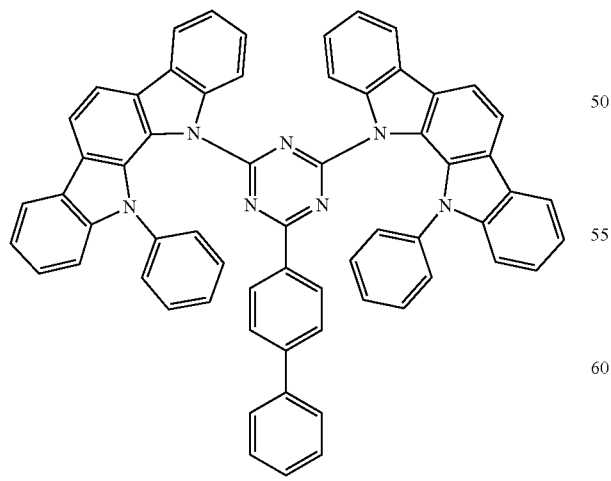

PIC-TRZ

-continued

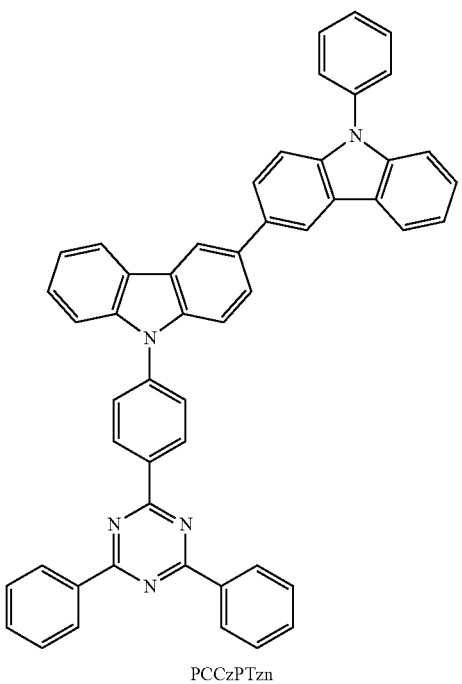

PCCzPTzn

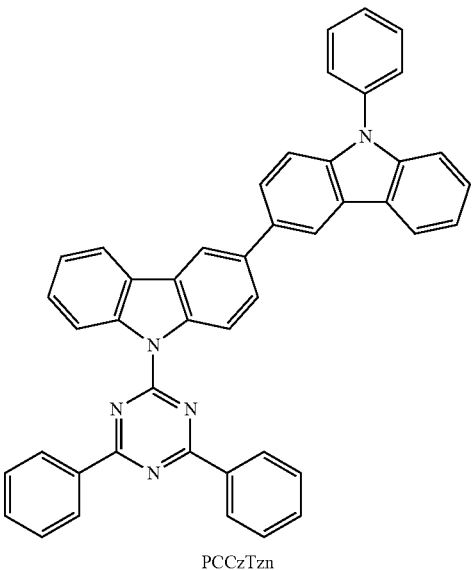

PCCzTzn

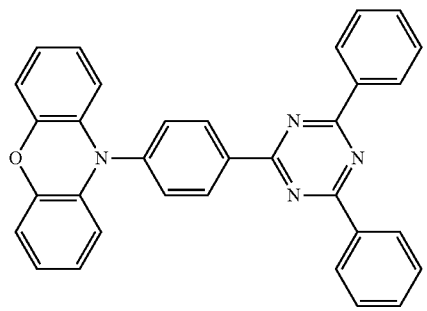

PXZ-TRZ

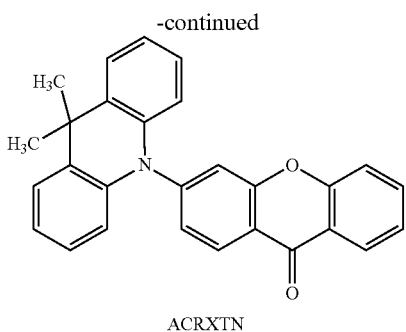

ACRXTN

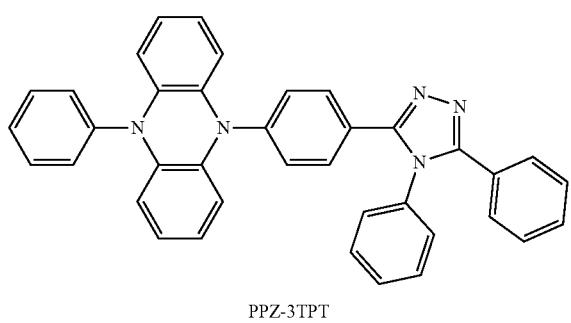

PPZ-3TPT

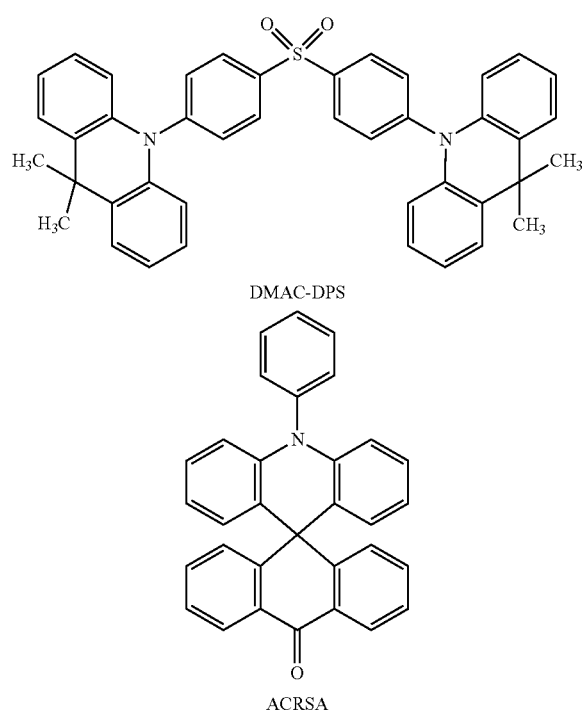

DMAC-DPS

ACRSA

Note that the TADF material is a material that has a small difference between the S1 level and the T1 level and has a function of converting triplet excitation energy into singlet excitation energy by reverse intersystem crossing. Thus, it is possible to upconverttriplet excitation energy into singlet excitation energy (reverse intersystem crossing) using a little thermal energy and to efficiently generate a singlet excited state. In addition, the triplet excitation energy can be converted into luminescence.

An exciplex (also referred to as Exciplex) whose excited state is formed by two kinds of substances has an extremely small difference between the S1 level and the T1 level and functions as a TADF material that can convert triplet excitation energy into singlet excitation energy.

Note that a phosphorescent spectrum observed at low temperatures (e.g., 77 K to 10 K) is used for an index of the T1 level. When the level of energy with a wavelength at which the line obtained by extrapolating a tangent to the fluorescent spectrum at a tail on the short wavelength side and the X axis intersect with each other is the S1 level and the level of energy with a wavelength of the line obtained by extrapolating a tangent to the phosphorescent spectrum at a tail on the short wavelength side is the T1 level, the difference between S1 and T1 of the TADF material is preferably smaller than or equal to 0.3 eV, further preferably smaller than or equal to 0.2 eV.

When the TADF material is used as an emission center material, the S1 level of the host material is preferably higher than that of the TADF material. In addition, the T1 level of the host material is preferably higher than that of the TADF material.

As the host material in the light-emitting layer, various carrier-transport materials, such as a material having an electron-transport property, a material having a hole-transport property, and the above-described TADF material, can be used.

As the material having a hole-transport property, the substances described above as the material having a hole-transport property included in the hole-transport layer 112 can be suitably used, and in particular, an organic compound having an aromatic amine skeleton is preferred because of its high hole-transport property and favorable stability. Among organic compounds having an aromatic amine skeleton, an organic compound having a triarylamine skeleton or a carbazole skeleton or the both is preferred.

Note that in the case where the material having a hole-transport property is the organic compound having both a triarylamine skeleton and a carbazole skeleton, an organic compound in which a nitrogen atom in the triarylamine skeleton and the carbazole skeleton are bonded through a phenylene group is preferred because of its stability and favorable reliability. Similarly, in the case where the material having a hole-transport property is the organic compound having both a triarylamine skeleton and a carbazole skeleton, the carbazole skeleton is preferably bonded to the amine at the 2-position to the 4-position or the 9-position in terms of reliability.

In the case where the material having a hole-transport property is an organic compound having a carbazole skeleton, an organic compound having a bicarbazole skeleton is preferred because of its favorable hole-transport property and high stability. In that case, the bicarbazole skeleton preferably has a structure in which two carbazolyl groups are bonded to each other at any of the 2-position to the 4-position.

As examples of materials having a hole-transport property with such a structure, the following substances can be given.

[Chemical Formula 11]
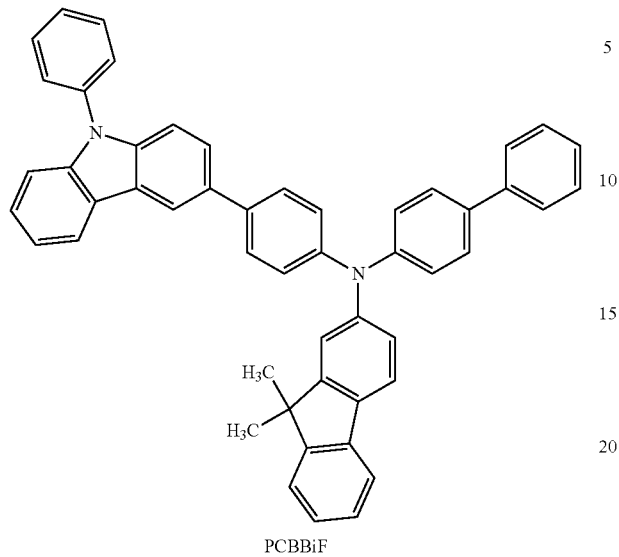
PCBBiF
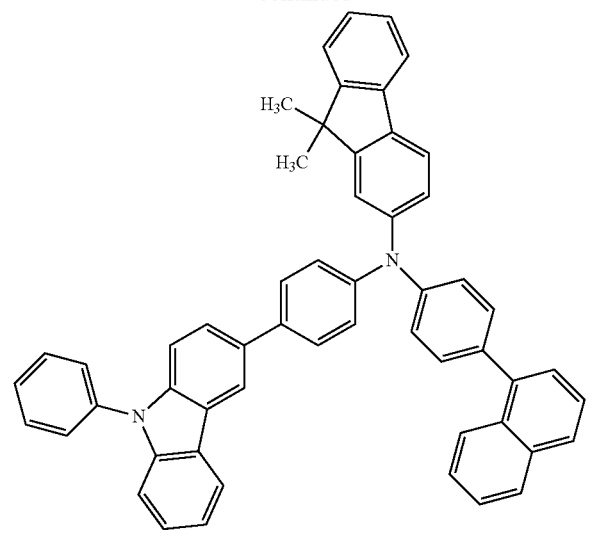
PCBNBF
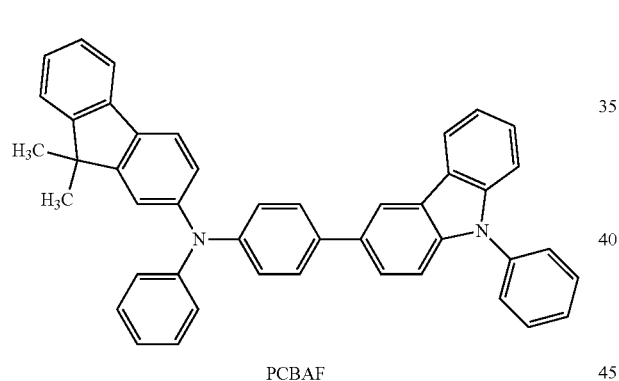
PCBAF
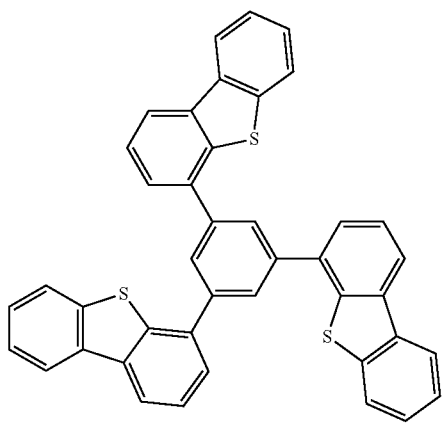
DBT3P-II
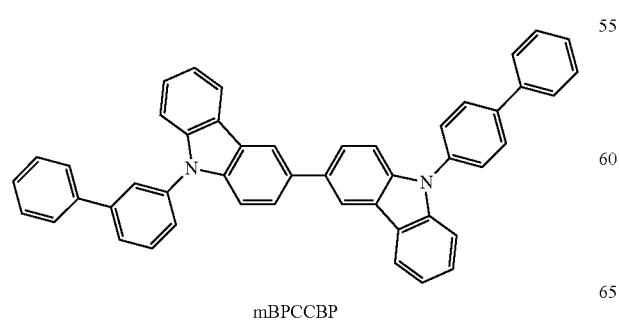
mBPCCBP
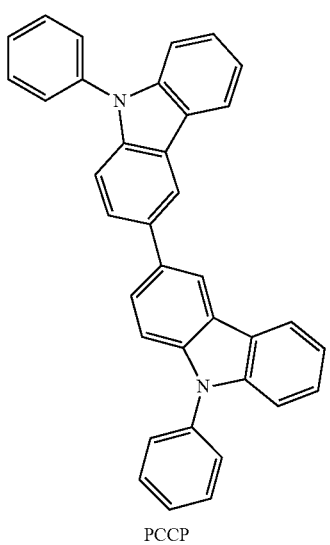
PCCP

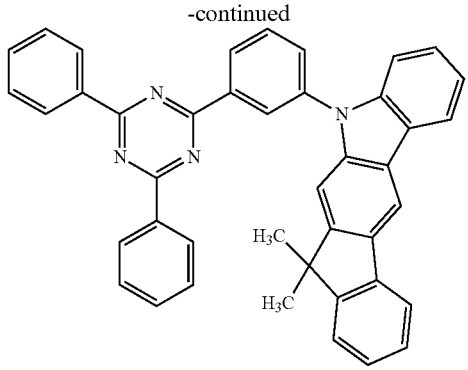

mINc(II)PTzn

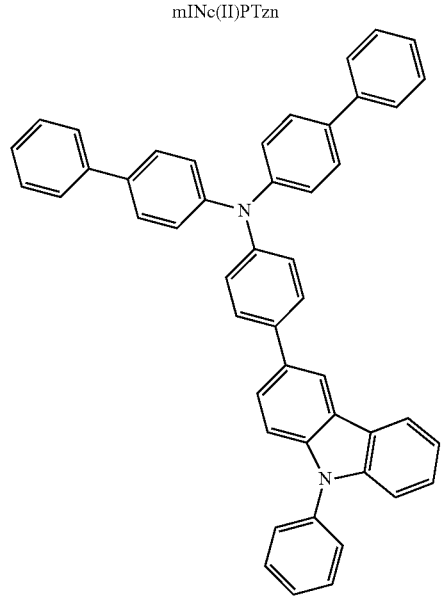

PCBBiIBP

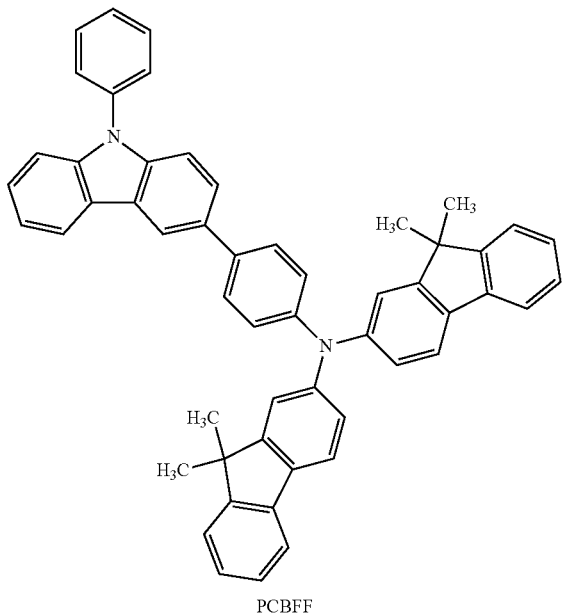

PCBFF

Examples of the material having an electron-transport property include a metal complex such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-TH-benzimidazole) (abbreviation: TPBI), and 2-[3-(dibenzothiophen-4-yl)phenyl]-1-phenyl-1H-benzimidazole (abbreviation: mDBTBIm-II); a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and a heterocyclic compound having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above, the heterocyclic compound having a diazine skeleton and the heterocyclic compound having a pyridine skeleton are preferred because of having high reliability. In particular, the heterocyclic compound having a diazine (pyrimidine or pyrazine) skeleton has a high electron-transport property and contributes to a reduction in driving voltage.

As the material having an electron-transport property, an organic compound having a benzofurodiazine skeleton or a benzothiodiazine skeleton is particularly preferred; especially, the organic compound represented by General Formula (G1) below is preferred.

[Chemical Formula 12]

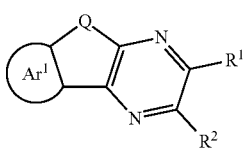

(G1)

In General Formula (G1) above, Q represents oxygen or sulfur. Furthermore, Ar$^1$ represents a substituted or unsubstituted condensed aromatic ring. One of R$^1$ and R$^2$ represents hydrogen and the other represents a group having a hole-transport-property skeleton and 1 to 100 carbon atoms in total. As examples of the hole-transport-property skeleton, a π-electron rich heteroaromatic ring skeleton, such as a pyrrole skeleton, a furan skeleton, a thiophene skeleton, or a carbazole skeleton, a condensed aromatic hydrocarbon ring skeleton, and an aromatic amine skeleton can be given.

In particular, an organic compound represented by Structural Formula (100) below is preferred.

[Chemical Formula 13]

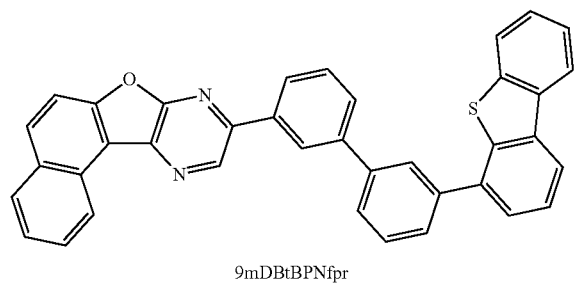

9mDBtBPNfpr

As the material having an electron-transport property, an organic compound having a benzofuropyrimidine skeleton or a benzothiopyrimidine skeleton is also preferred; especially, the organic compound represented by General Formula (G2) below is preferred.

[Chemical Formula 14]

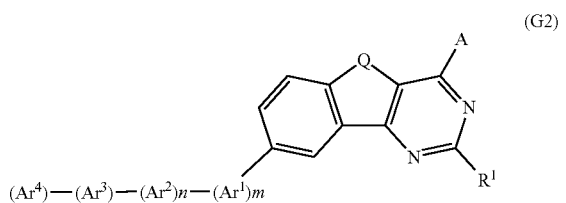

In the formula, Q represents oxygen or sulfur. Each of $Ar^1$, $Ar^2$, $Ar^3$, and $Ar^4$ independently represents a substituted or unsubstituted aromatic hydrocarbon ring, a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group, and the number of carbon atoms included in the aromatic hydrocarbon ring is greater than or equal to 6 and less than or equal to 25. In addition, each of m and n independently represents 0 or 1. Moreover, A represents a group having 12 to 100 carbon atoms in total and includes one or more of a benzene ring, a naphthalene ring, a fluorene ring, a phenanthrene ring, a triphenylene ring, a heteroaromatic ring including a dibenzothiophene ring, a heteroaromatic ring including a dibenzofuran ring, a heteroaromatic ring including a carbazole ring, a benzimidazole ring, and a triphenylamine structure. Furthermore, $R^1$ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms. Note that in General Formula (G2) above, m and n preferably represent 0.

As examples of the organic compound having a benzofurodiazine skeleton or a benzothiodiazine skeleton or the organic compound having a benzofuropyrimidine skeleton or a benzothiopyrimidine skeleton which can be suitably used as the material having an electron-transport property, the following substances can be given.

[Chemical Formula 15]

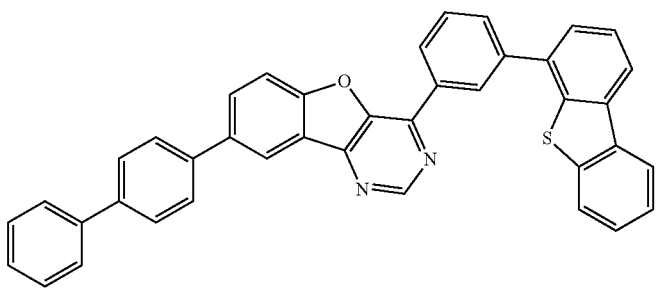

8BP-4mDBtPBfpm

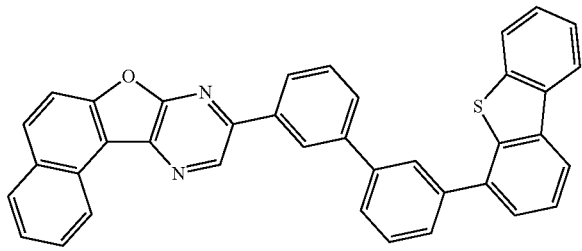

9mDBtBPNfpr

-continued
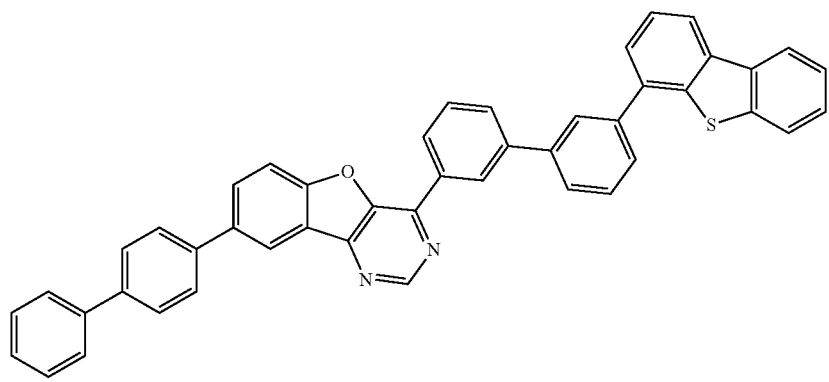
8BP-4mDBtBPBfpm
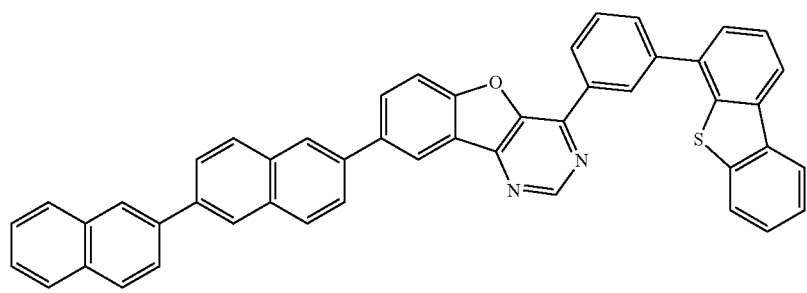
8(βN2)-4mDBtPBfpm
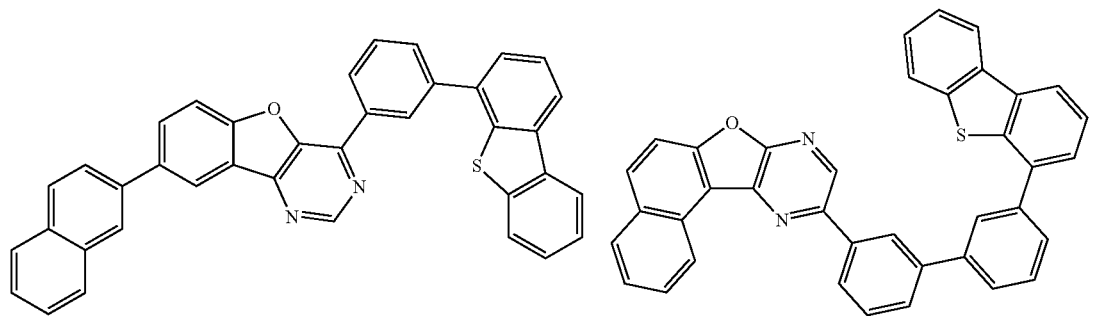
8βN-4mDBtPBfpm          10mDBtBPNfpr
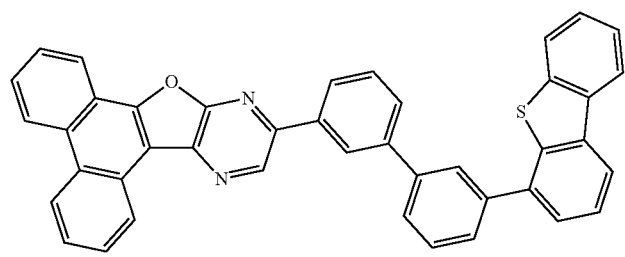
11mDBtBPPnfpr Among the above-described organic compounds, an organic compound represented by Structural Formula (200) or (201) below is particularly preferred.

[Chemical Formula 16]

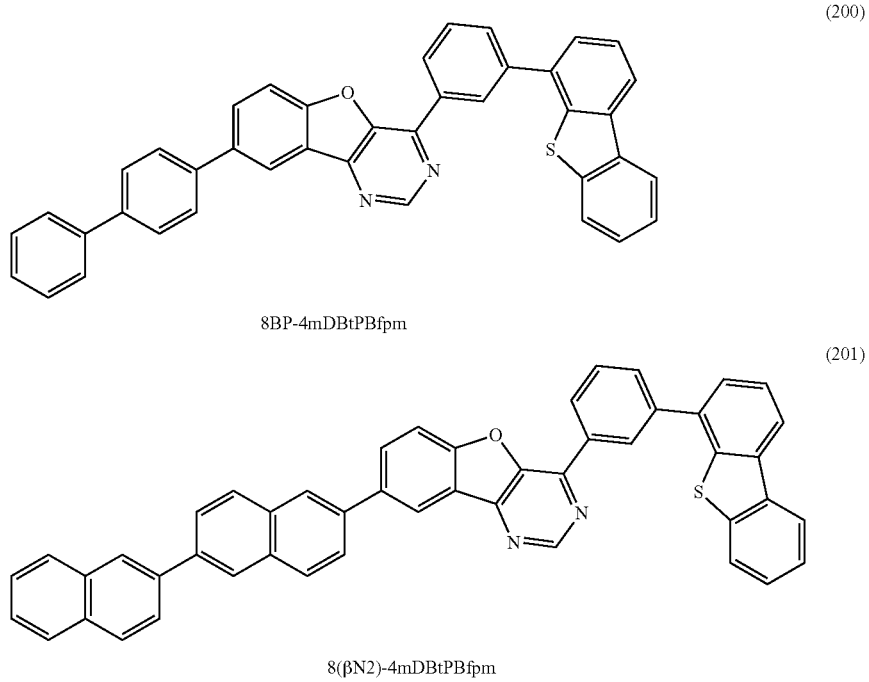

In the case where a fluorescent substance is used as the light-emitting material, a material having an anthracene skeleton is favorably used as the host material. The use of a substance having an anthracene skeleton as the host material for the fluorescent substance makes it possible to obtain a light-emitting layer with high emission efficiency and high durability. Most of materials having an anthracene skeleton have a deep HOMO level; therefore, one embodiment of the present invention can be suitably used. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferred as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). In particular, CzPA, cgDBCzPA, 2mBnfPPA, and PCzPA are preferably selected because they exhibit excellent characteristics.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed of these mixed materials. These mixed materials are preferably selected so as to form an exciplex that exhibits light emission whose wavelength overlaps with the wavelength on a lowest-energy-side absorption band of the light-emitting material, in which case energy can be transferred smoothly and light emission can be obtained efficiently. The use of such a structure is preferred because the driving voltage can also be reduced.

Since the light-emitting layer 113 often has a structure in which a plurality of substances exist in the same layer, the composition for an EL device of one embodiment of the present invention can be suitably used for forming the light-emitting layer 113. The composition for an EL device of one embodiment of the present invention can be obtained by selecting two or more kinds among the above-described materials such that a difference in the 5% weight loss temperature between the two or more kinds of organic compounds measured by thermogravimetry under a pressure of 0.1 Pa or lower is 50° C. or lower and by mixing them at a given ratio. Even when the composition for an EL device is evaporated successively, the composition itself or the composition of a formed film does not largely change. Therefore, an EL device manufactured using the composition for an EL device can exhibit favorable and stable characteristics.

Since a plurality of organic compounds can be evaporated from one evaporation source, EL devices with favorable characteristics can be manufactured without extra or additional capital investment. That is, EL devices with favorable characteristics can be manufactured at low cost.

The electron-transport layer 114 contains a substance having an electron-transport property. As the substance having an electron-transport property, it is possible to use any of the above-listed substances having electron-transport properties that can be used as the host material.

A layer containing an alkali metal, an alkaline earth metal, or a compound thereof such as lithium fluoride (LiF), cesium fluoride (CsF), or calcium fluoride ($CaF_2$) may be provided as the electron-injection layer 115 between the electron-transport layer 114 and the cathode 102. An electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer that contains a substance having an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, an EL device including the layer can have favorable external quantum efficiency.

Figure 1B:
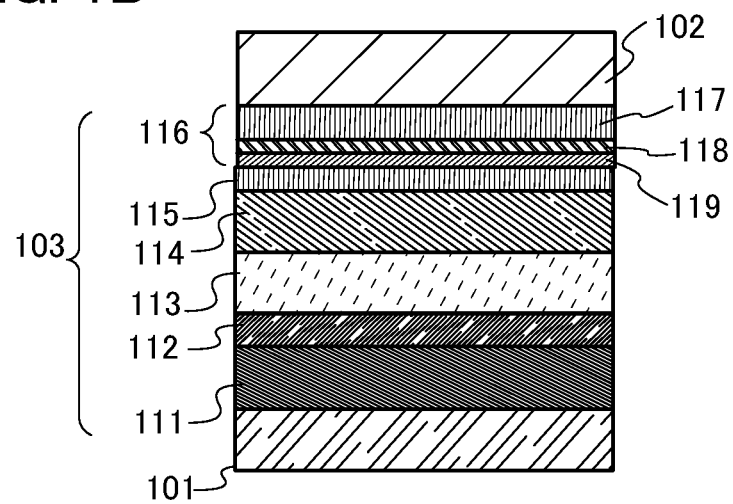

Instead of the electron-injection layer 115, the charge-generation layer 116 may be provided (FIG. 1B). The charge-generation layer 116 refers to a layer capable of injecting holes into the cathode and electrons into a layer in contact with the anode side when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the cathode 102; thus, the EL device operates.

Note that the charge-generation layer 116 preferably includes one or both of an electron-relay layer 118 and an electron-injection buffer layer 119 in addition to the p-type layer 117.

The electron-relay layer 118 contains at least a substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the substance having an electron-accepting property in the p-type layer 117 and the LUMO level of a substance contained in a layer of the electron-transport layer 114 that is in contact with the charge-generation layer 116. The specific LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property, such as an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)), can be used for the electron-injection buffer layer 119.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

As a substance for forming the cathode 102, a metal, an alloy, an electrically conductive compound, or a mixture thereof each having a low work function (specifically, lower than or equal to 3.8 eV) or the like can be used. Specific examples of such a cathode material are elements belonging to Group 1 or Group 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the cathode 102 and the electron-transport layer 114, for the cathode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry process or a wet process. For example, a vacuum evaporation method, a gravure printing method, an offset printing method, a screen printing method, an ink-jet method, a spin coating method, or the like may be used. Note that in the case where a plurality of substances are made exist in one layer by an evaporation method, the use of the composition for an EL device of one embodiment of the present invention enables fabrication of EL devices with favorable and stable characteristics. Furthermore, increases in capital investment and time and effort for maintenance are inhibited, which is advantageous in cost.

Different methods may be used to form each of the electrodes or layers described above.

The structure of the layers provided between the anode 101 and the cathode 102 is not limited to the above-described structure. Preferably, a light-emitting region where holes and electrons recombine is positioned away from the anode 101 and the cathode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of an EL device with a structure where a plurality of light-emitting units are stacked (also referred to as a stacked-type device or a tandem device) will be described with reference to FIG. 1C. This EL device is an EL device including a plurality of light-emitting units between an anode and a cathode. One light-emitting unit has substantially the same structure as that of the EL layer 103, which is shown in FIG. 1A. In other words, the EL device shown in FIG. 1C is an EL device including a plurality of light-emitting units, and the EL device shown in FIG. 1A or FIG. 1B is an EL device including one light-emitting unit.

Figure 1C:
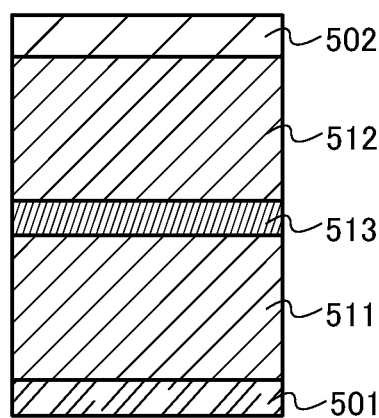

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the anode 101 and the cathode 102 in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1C, the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The EL device having two light-emitting units is described with reference to FIG. 1C; however, the above structure can also be applied to an EL device in which three or more light-emitting units are stacked. With a plurality of light-emitting units partitioned by the charge-generation layer 513 between a pair of electrodes as in the EL device of this embodiment, it is possible to provide a long-life EL device which can emit light with high luminance at a low current density. A light-emitting apparatus which can be driven at a low voltage and has low power consumption can be achieved.

When the emission colors of the light-emitting units are different, light emission of a desired color can be obtained from the EL device as a whole. For example, in an EL device having two light-emitting units, the emission colors of the first light-emitting unit may be red and green and the emission color of the second light-emitting unit may be blue, so that the EL device can emit white light as the whole.

Embodiment 3

In this embodiment, a light-emitting apparatus using the EL device described in Embodiment 2 will be described.

Figure 2A:
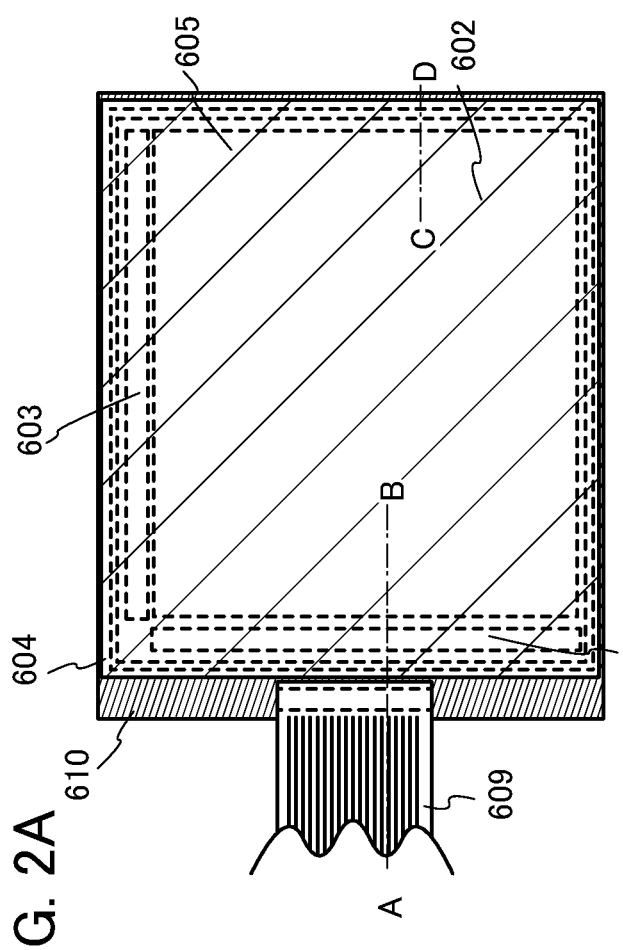
FIG. 2A and FIG. 2B are conceptual diagrams of an active matrix light-emitting apparatus.
Figure 2B:
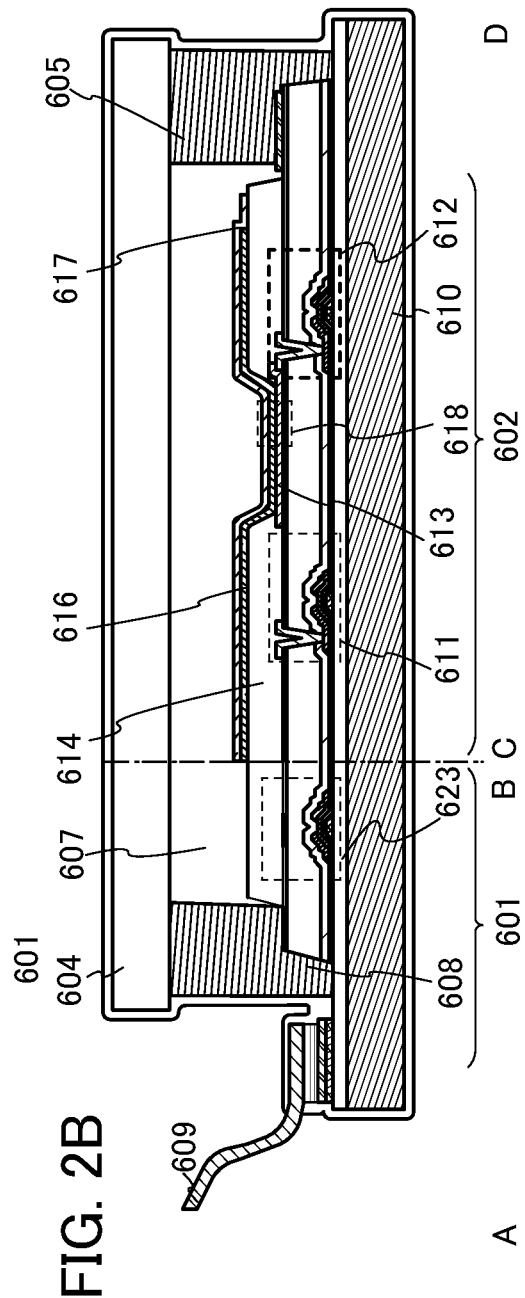

In this embodiment, a light-emitting apparatus fabricated using the EL device described in Embodiment 2 will be described with reference to FIG. 2. Note that FIG. 2A is a top view showing the light-emitting apparatus, and FIG. 2B is a cross-sectional view taken along the lines A-B and C-D in FIG. 2A. This light-emitting apparatus includes a driver circuit portion (source line driver circuit) 601, a pixel portion 602, and a driver circuit portion (gate line driver circuit) 603, which are for controlling light emission of an EL device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 2B. The driver circuit portion and the pixel portion are formed over an element substrate 610; here, the source line driver circuit 601, which is the driver circuit portion, and one pixel in the pixel portion 602 are shown.

The element substrate 610 may be fabricated using a substrate containing glass, quartz, an organic resin, a metal, an alloy, a semiconductor, or the like, or a plastic substrate formed of FRP (Fiber Reinforced Plastics), PVF (polyvinyl fluoride), polyester, an acrylic resin, or the like.

There is no particular limitation on the structure of transistors used in pixels and driver circuits. For example, an inverted staggered transistor or a staggered transistor may be used. Furthermore, top-gate transistors or bottom-gate transistors may be used. There is no particular limitation on a semiconductor material used for the transistors, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor and a semiconductor having crystallinity (a microcrystalline semiconductor, a polycrystalline semiconductor, a single crystal semiconductor, or a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M is a metal such as Al, Ti, Ga, Ge, Y, Zr, Sn, La, Ce, or Hf).

An oxide semiconductor that can be used in one embodiment of the present invention is described below.

Oxide semiconductors can be classified into a single crystal oxide semiconductor and a non-single-crystal oxide semiconductor. Examples of the non-single-crystal oxide semiconductor include a CAAC-OS (c-axis aligned crystalline oxide semiconductor), a polycrystalline oxide semiconductor, an nc-OS (nano crystalline oxide semiconductor), an amorphous-like oxide semiconductor (a-like OS), and an amorphous oxide semiconductor.

The CAAC-OS has c-axis alignment, a plurality of nanocrystals are connected in the a-b plane direction, and its crystal structure has distortion. Note that the distortion refers to a portion where the direction of a lattice arrangement changes between a region with a regular lattice arrangement and another region with a regular lattice arrangement in a region where the plurality of nanocrystals are connected.

The nanocrystal is basically a hexagon but is not always a regular hexagon and is a non-regular hexagon in some cases. Furthermore, a pentagonal or heptagonal lattice arrangement, for example, is included in the distortion in some cases. Note that it is difficult to observe a clear crystal grain boundary (also referred to as grain boundary) even in the vicinity of distortion in the CAAC-OS. That is, formation of a crystal grain boundary is found to be inhibited by the distortion of a lattice arrangement. This is because the CAAC-OS can tolerate distortion owing to a low density of arrangement of oxygen atoms in the a-b plane direction, an interatomic bond length changed by substitution of a metal element, and the like.

The CAAC-OS tends to have a layered crystal structure (also referred to as a layered structure) in which a layer containing indium and oxygen (hereinafter, an In layer) and a layer containing the element M, zinc, and oxygen (hereinafter, an (M,Zn) layer) are stacked. Note that indium and the element M can be replaced with each other, and when the element M in the (M,Zn) layer is replaced with indium, the layer can also be referred to as an (In,M,Zn)layer. Furthermore, when indium in the In layer is replaced with the element M, the layer can be referred to as an (In,M) layer.

The CAAC-OS is an oxide semiconductor with high crystallinity. On the other hand, a clear crystal grain boundary cannot be observed in the CAAC-OS; thus, it can be said that a reduction in electron mobility due to the crystal grain boundary is less likely to occur. Entry of impurities, formation of defects, or the like might decrease the crystallinity of an oxide semiconductor; thus, it can be said that the CAAC-OS is an oxide semiconductor that has small amounts of impurities and defects (e.g., oxygen vacancies (also referred to as Vo)). Thus, an oxide semiconductor including the CAAC-OS is physically stable. Therefore, the oxide semiconductor including the CAAC-OS is resistant to heat and has high reliability.

In the nc-OS, a microscopic region (e.g., a region with a size greater than or equal to 1 nm and less than or equal to 10 nm, in particular, a region with a size greater than or equal to 1 nm and less than or equal to 3 nm) has a periodic atomic arrangement. Furthermore, there is no regularity of crystal orientation between different nanocrystals in the nc-OS. Thus, the orientation in the whole film is not observed. Accordingly, the nc-OS cannot be distinguished from an a-like OS or an amorphous oxide semiconductor by some analysis methods.

Note that indium-gallium-zinc oxide (hereinafter referred to as IGZO) that is a kind of oxide semiconductor containing indium, gallium, and zinc has a stable structure in some cases by being formed of the above-described nanocrystals. In particular, crystals of IGZO tend not to grow in the air and thus, a stable structure is obtained when IGZO is formed of smaller crystals (e.g., the above-described nanocrystals) rather than larger crystals (here, crystals with a size of several millimeters or several centimeters).

The a-like OS is an oxide semiconductor having a structure between those of the nc-OS and the amorphous oxide semiconductor. The a-like OS includes a void or a low-density region. That is, the a-like OS has low crystallinity compared with the nc-OS and the CAAC-OS.

An oxide semiconductor has various structures with different properties. Two or more of the amorphous oxide semiconductor, the polycrystalline oxide semiconductor, the a-like OS, the nc-OS, and the CAAC-OS may be included in an oxide semiconductor described here.

As an oxide semiconductor other than the above, a CAC (Cloud-Aligned Composite)-OS may be used.

A CAC-OS has a conducting function in part of the material and has an insulating function in another part of the material; as a whole, the CAC-OS has a function of a semiconductor. Note that in the case where the CAC-OS is used in a semiconductor layer of a transistor, the conducting function is a function that allows electrons (or holes) serving as carriers to flow, and the insulating function is a function that does not allow electrons serving as carriers to flow. By the complementary action of the conducting function and the insulating function, a switching function (On/Off function) can be given to the CAC-OS. In the CAC-OS, separation of the functions can maximize each function.

In addition, the CAC-OS includes conductive regions and insulating regions. The conductive regions have the above-described conducting function, and the insulating regions have the above-described insulating function. Furthermore, in some cases, the conductive regions and the insulating regions in the material are separated at the nanoparticle level. Furthermore, in some cases, the conductive regions and the insulating regions are unevenly distributed in the material. Furthermore, in some cases, the conductive regions are observed to be coupled in a cloud-like manner with their boundaries blurred.

In the CAC-OS, the conductive regions and the insulating regions each have a size greater than or equal to 0.5 nm and less than or equal to 10 nm, preferably greater than or equal to 0.5 nm and less than or equal to 3 nm, and are dispersed in the material, in some cases.

The CAC-OS is composed of components having different band gaps. For example, the CAC-OS is composed of a component having a wide gap due to the insulating region and a component having a narrow gap due to the conductive region. In the case of the structure, when carriers flow, carriers mainly flow in the component having a narrow gap. Furthermore, the component having a narrow gap complements the component having a wide gap, and carriers also flow in the component having a wide gap in conjunction with the component having a narrow gap. Therefore, in the case where the above-described CAC-OS is used in a channel formation region of a transistor, the transistor in the on state can achieve high current driving capability, that is, high on-state current and high field-effect mobility.

In other words, the CAC-OS can also be referred to as a matrix composite or a metal matrix composite.

The use of the aforementioned oxide semiconductor material for the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic apparatus with significantly reduced power consumption can be achieved.

For stable characteristics of the transistor, a base film is preferably provided. The base film can be formed to be a single layer or a stacked layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and an anode 613 electrically connected to a drain of the current control FET 612; however, without being limited thereto, a pixel portion in which three or more FETs and a capacitor are combined may be employed.

Note that an insulator 614 is formed to cover an end portion of the anode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where positive photosensitive acrylic is used as a material for the insulator 614, only the upper end portion of the insulator 614 preferably has a curved surface with a curvature radius (0.2 µm to 3 µm). For the insulator 614, either a negative photosensitive resin or a positive photosensitive resin can be used.

An EL layer 616 and a cathode 617 are formed over the anode 613. Here, as a material used for the anode 613 functioning as an anode, a material with a high work function is desirably used. For example, a single-layer film of an ITO film, an indium tin oxide film containing silicon, an indium oxide film containing zinc oxide at 2 to 20 wt %, a titanium nitride film, a chromium film, a tungsten film, a Zn film, a Pt film, or the like, a stacked layer of a titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. Alternatively, a material included in the EL layer 616 may be a low molecular compound or a high molecular compound (including an oligomer or a dendrimer).

As a material used for the cathode 617 functioning as a cathode, which is formed over the EL layer 616, a material with a low work function (e.g., Al, Mg, Li, Ca, or an alloy or a compound thereof (MgAg, MgIn, AlLi, or the like)) is preferably used. Note that in the case where light generated in the EL layer 616 passes through the cathode 617, it is preferable to use, for the cathode 617, a stacked layer of a thin metal film and a transparent conductive film (e.g., ITO, indium oxide containing zinc oxide at 2 to 20 wt %, indium tin oxide containing silicon, or zinc oxide (ZnO)).

Note that an EL device 618 is formed with the anode 613, the EL layer 616, and the cathode 617. The EL device 618 is the EL device described in Embodiment 2. A plurality of EL devices are formed in the pixel portion, and the light-emitting apparatus of this embodiment may include both the EL device described in Embodiment 2 and an EL device having a different structure.

The sealing substrate 604 and the element substrate 610 are attached to each other using the sealant 605, achieving a structure in which the EL device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The sealing substrate in which a recessed portion is formed and a desiccant is provided therein is preferred because deterioration due to the influence of moisture can be inhibited.

Note that an epoxy-based resin or glass frit is preferably used for the sealant 605. Furthermore, these materials are preferably materials that transmit moisture or oxygen as little as possible. For the sealing substrate 604, in addition to a glass substrate and a quartz substrate, a plastic substrate formed of FRP (Fiber Reinforced Plastics), PVF (polyvinyl fluoride), polyester, an acrylic resin, or the like can be used.

Although not shown in FIG. 2, a protective film may be provided over the cathode. As the protective film, an organic resin film or an inorganic insulating film can be formed. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely to transmit an impurity such as water can be used. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, or indium oxide; or a material containing aluminum nitride, hafnium nitride, silicon nitride, tantalum nitride, titanium nitride, niobium nitride, molybdenum nitride, zirconium nitride, or gallium nitride; a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

For example, by an ALD method, a uniform protective film with few defects can be formed even on a surface with a complex uneven shape or upper, side, and lower surfaces of a touch panel.

The light-emitting apparatus fabricated using the EL device described in Embodiment 2 can be obtained in the above manner.

The light-emitting apparatus in this embodiment uses the EL device described in Embodiment 2 and thus has favorable characteristics. Specifically, since the EL device described in Embodiment 2 has favorable emission efficiency, the light-emitting apparatus can achieve low power consumption.

FIG. 3 shows examples of a light-emitting apparatus which achieves full color display by formation of an EL device exhibiting white light emission and provision of coloring layers (color filters) and the like. FIG. 3A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, anodes 1024W, 1024R, 1024G, and 1024B of the EL devices, a partition 1025, an EL layer 1028, a cathode 1029 of the EL devices, a sealing substrate 1031, a sealant 1032, and the like.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, there is a light-emitting layer from which light is extracted to the outside without passing through the coloring layers and a light-emitting layer from which light is extracted to the outside after passing through the coloring layers of the respective colors. The light that does not pass through the coloring layers is white, and the light that passes through the coloring layers is red, green, and blue, so that an image can be expressed with the pixels of four colors.

FIG. 3B shows an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
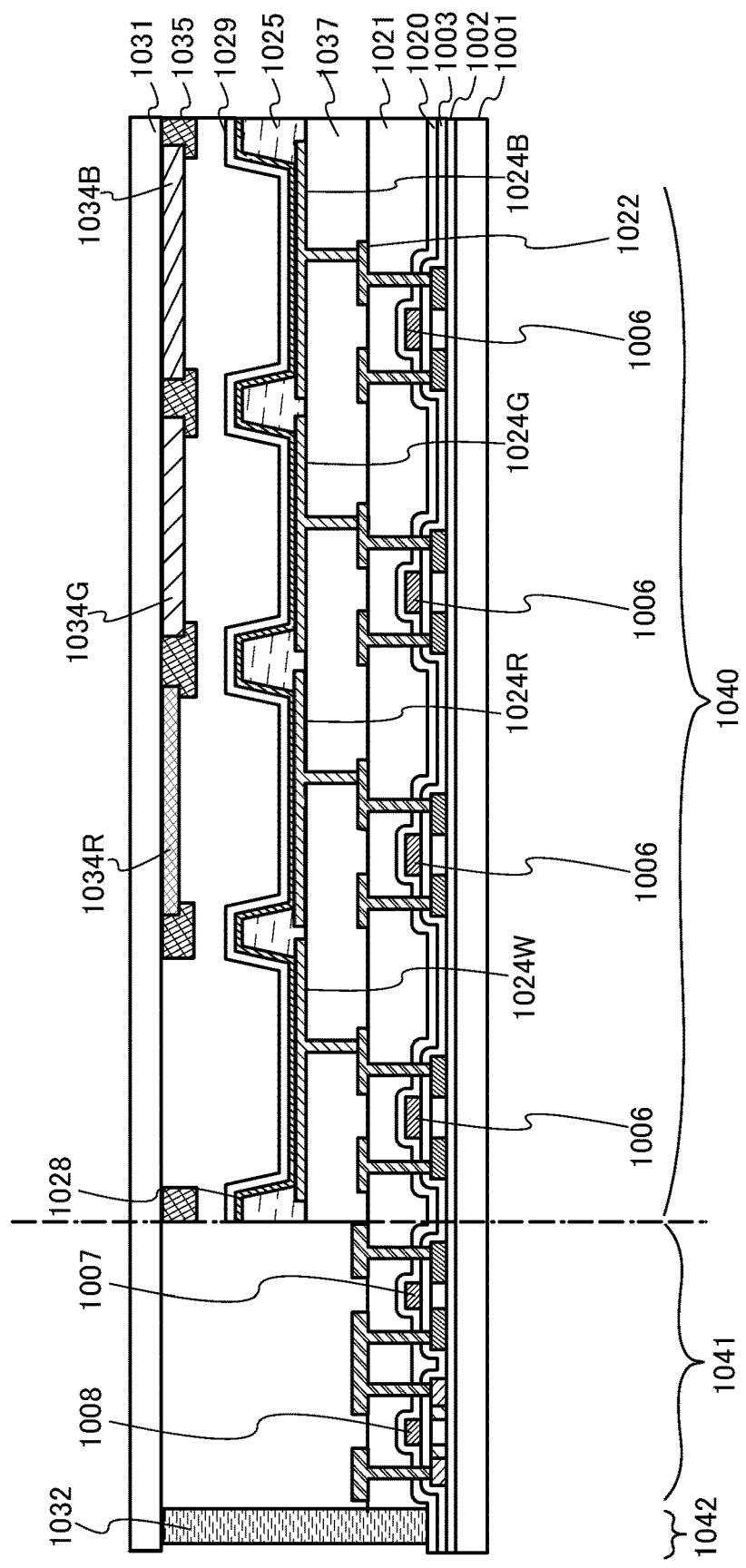
FIG. 4 is a conceptual diagram of an active matrix light-emitting apparatus.

The above-described light-emitting apparatus is a light-emitting apparatus having a structure in which light is extracted to the substrate 1001 side where the FETs are formed (a bottom-emission type), but may be a light-emitting apparatus having a structure in which light emission is extracted to the sealing substrate 1031 side (a top-emission type). FIG. 4 shows a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the EL device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The anodes 1024W, 1024R, 1024G, and 1024B of the EL devices may each be a cathode though they are anodes here. Furthermore, in the case of the top-emission light-emitting apparatus shown in FIG. 4, the anodes are preferably reflective electrodes. The EL layer 1028 has a structure similar to the structure of the EL layer 103 described in Embodiment 2, with which white light emission can be obtained.

In the top-emission structure as shown in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission light-emitting apparatus, a microcavity structure can be favorably employed. An EL device with a microcavity structure can be obtained with the use of a reflective electrode as the anode and a semi-transmissive and semi-reflective electrode as the cathode. At least an EL layer is provided between the reflective electrode and the semi-transmissive and semi-reflective electrode, and the EL layer includes at least a light-emitting layer functioning as a light-emitting region.

Note that the reflective electrode is a film having a visible light reflectance of 40% to 100%, preferably 70% to 100%, and a resistivity of $1\times10^{-2}$ $\Omega$cm or lower. The semi-transmissive and semi-reflective electrode is a film having a visible light reflectance of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the EL device, by changing the thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and $\lambda$ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer; for example, in combination with the structure of the above-described tandem EL device, a plurality of EL layers each including a single or a plurality of light-emitting layer(s) may be provided in one EL device with a charge-generation layer interposed between the EL layers.

With the microcavity structure, emission intensity with a particular wavelength in the front direction can be increased, whereby power consumption can be reduced. Note that in the case of a light-emitting apparatus which displays images with subpixels of four colors of red, yellow, green, and blue, the light-emitting apparatus can have favorable characteristics because the luminance can be increased owing to yellow light emission and each subpixel can employ a microcavity structure suitable for the wavelength of the corresponding color.

The light-emitting apparatus in this embodiment uses the EL device described in Embodiment 2 and thus has favorable characteristics. Specifically, since the EL device described in Embodiment 2 has favorable emission efficiency, the light-emitting apparatus can achieve low power consumption.

Figure 5A:
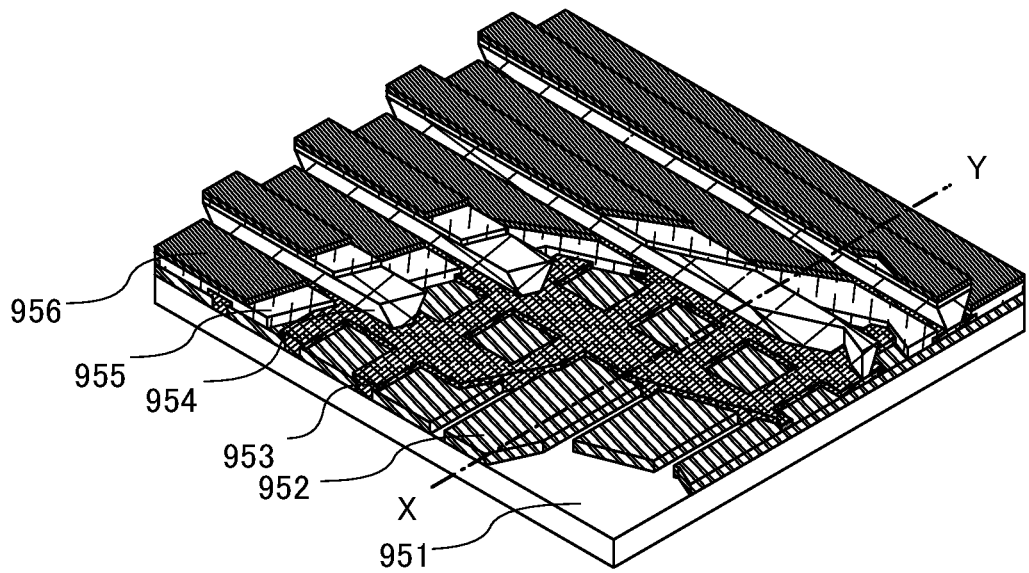
FIG. 5A and FIG. 5B are conceptual diagrams of a passive matrix light-emitting apparatus.
Figure 5B:
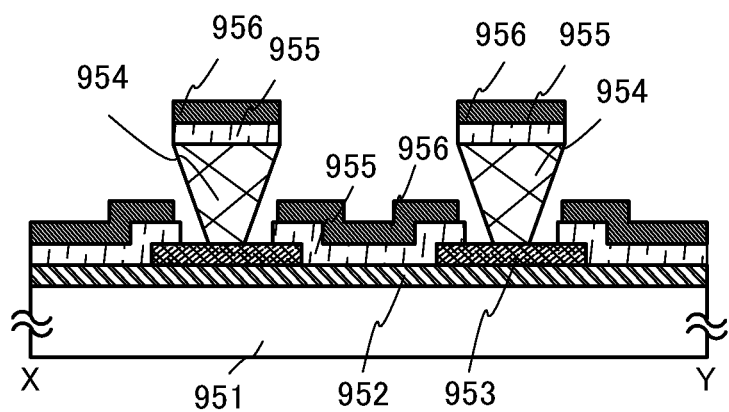

The active matrix light-emitting apparatus is described above, whereas a passive matrix light-emitting apparatus is described below. FIG. 5 illustrates a passive matrix light-emitting apparatus fabricated using the present invention. Note that FIG. 5A is a perspective view showing the light-emitting apparatus, and FIG. 5B is a cross-sectional view taken along the line X-Y in FIG. 5A. In FIG. 5, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). Providing the partition layer 954 in this manner can prevent defects of the EL device due to static charge or the like. The passive-matrix light-emitting apparatus also uses the EL device described in Embodiment 2; thus, the light-emitting apparatus can have favorable reliability or low power consumption.

Since many minute EL devices arranged in a matrix can be controlled in the above-described light-emitting apparatus, the light-emitting apparatus can be suitably used as a display device for expressing images.

This embodiment can be freely combined with any of the other embodiments.

Embodiment 4

Figure 6A:
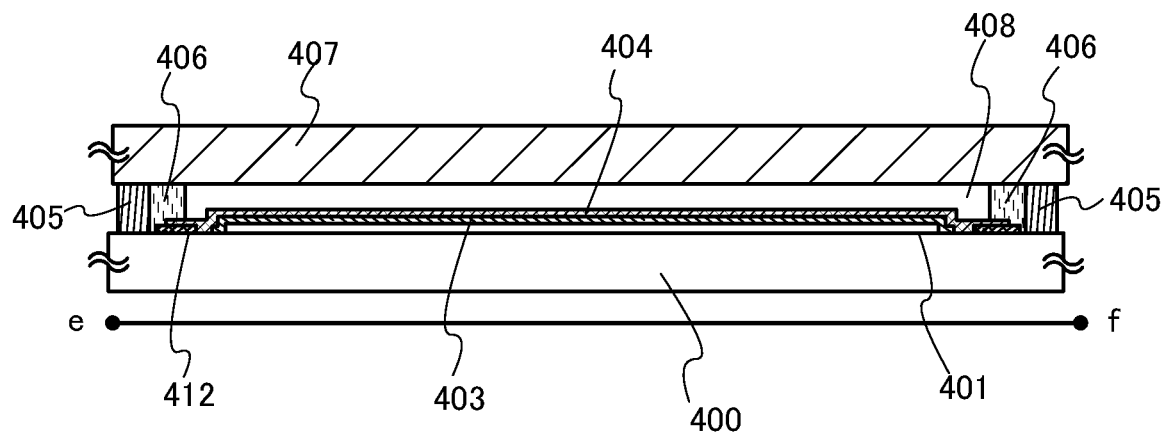
FIG. 6A and FIG. 6B are diagrams illustrating a lighting device.
Figure 6B:
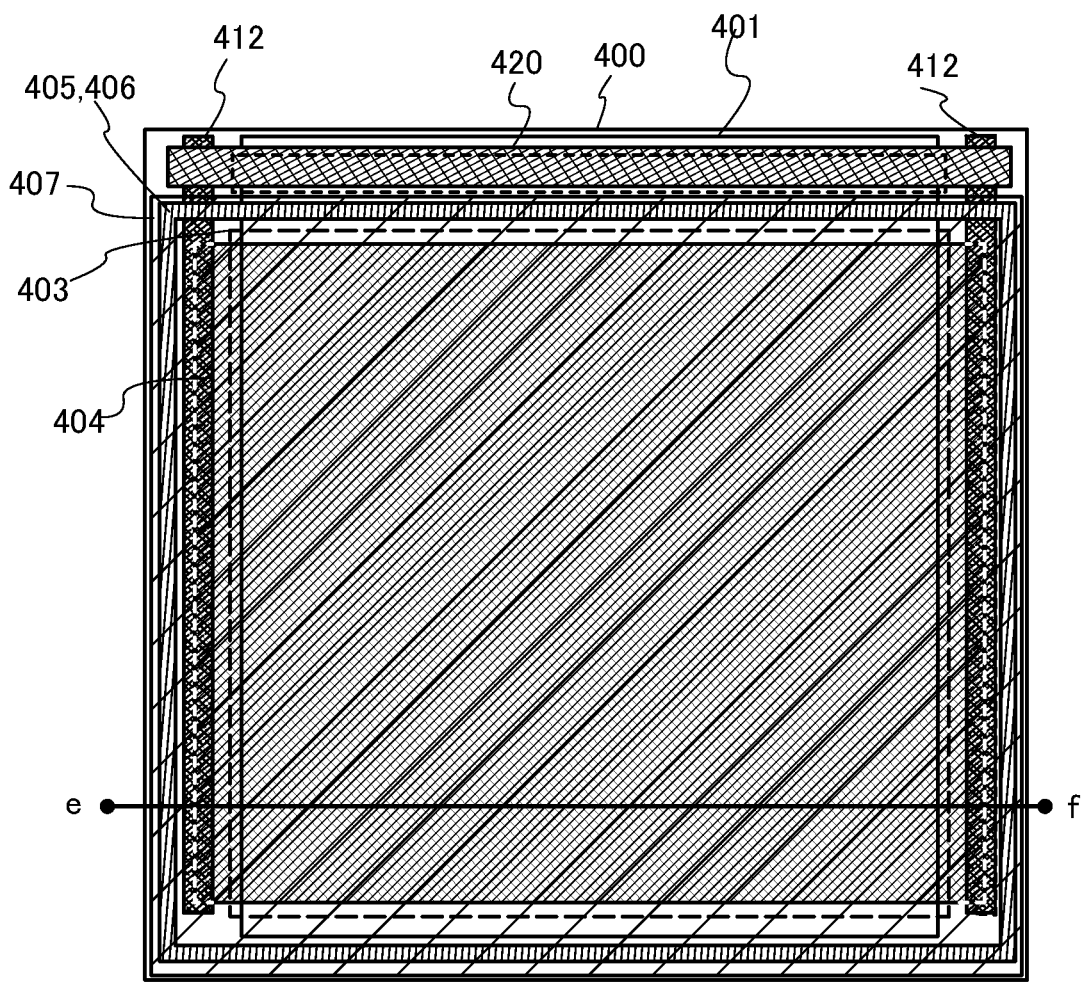

In this embodiment, an example in which the EL device described in Embodiment 2 is used for a lighting device will be described with reference to FIG. 6. FIG. 6B is a top view of the lighting device, and FIG. 6A is a cross-sectional view taken along e-f in FIG. 6B.

In the lighting device in this embodiment, an anode 401 is formed over a substrate 400 which is a support and has a light-transmitting property. The anode 401 corresponds to the anode 101 in Embodiment 2. In the case where light emission is extracted from the anode 401 side, the anode 401 is formed with a material having a light-transmitting property.

A pad 412 for supplying a voltage to a cathode 404 is formed over the substrate 400.

An EL layer 403 is formed over the anode 401. The EL layer 403 has a structure corresponding to that of the EL layer 103 in Embodiment 2, or the structure in which the light-emitting units 511 and 512 are combined with the charge-generation layer 513. Note that for these structures, the corresponding description can be referred to.

The cathode 404 is formed to cover the EL layer 403. The cathode 404 corresponds to the cathode 102 in Embodiment 2. In the case where light-emission is extracted from the anode 401 side, the cathode 404 is formed with a material having high reflectivity. The cathode 404 is supplied with a voltage when connected to the pad 412.

As described above, the lighting device described in this embodiment includes an EL device including the anode 401, the EL layer 403, and the cathode 404. Since the EL device is an EL device with high emission efficiency, the lighting device in this embodiment can be a lighting device with low power consumption.

The substrate 400 over which the EL device having the above structure is formed is fixed to a sealing substrate 407 with sealants 405 and 406 and sealing is performed, whereby the lighting device is completed. It is possible to use only either the sealant 405 or 406. In addition, the inner sealant 406 (not illustrated in FIG. 6B) can be mixed with a desiccant, which enables moisture to be adsorbed, resulting in improved reliability.

When parts of the pad 412 and the anode 401 are provided to extend to the outside of the sealants 405 and 406, those can serve as external input terminals. An IC chip 420 mounted with a converter or the like may be provided over the external input terminals.

The lighting device described in this embodiment uses the EL device described in Embodiment 2 as an EL device; thus, the light-emitting apparatus can have low power consumption.

Embodiment 5

In this embodiment, examples of electronic devices each partly including the EL device described in Embodiment 2 will be described. The EL device described in Embodiment 2 is an EL device having high emission efficiency and low power consumption. Thus, the electronic devices described in this embodiment can be electronic devices including light-emitting portions with reduced power consumption.

Examples of electronic devices to which the EL device is applied include a television devices (also referred to as TV or television receivers), monitors for computers and the like, cameras such as digital cameras and digital video cameras, digital photo frames, mobile phones (also referred to as portable telephones or portable telephone devices), portable game machines, portable information terminals, audio playback devices, and large game machines such as pin-ball machines. Specific examples of these electronic devices are shown below.

Figure 7A:
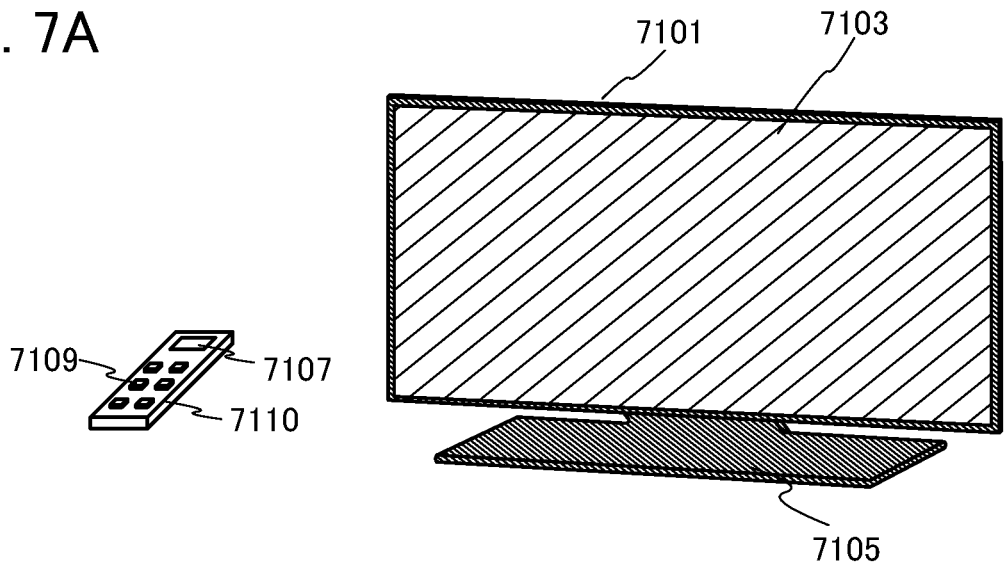
Figure 7A:
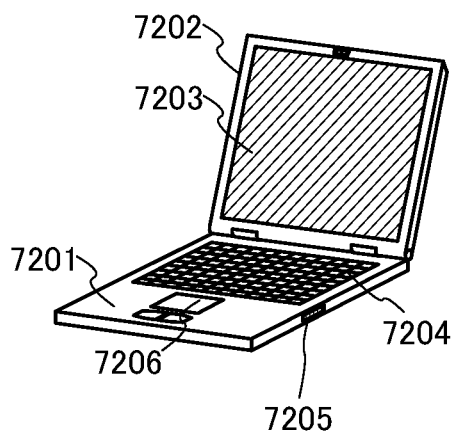
Figure 7A:
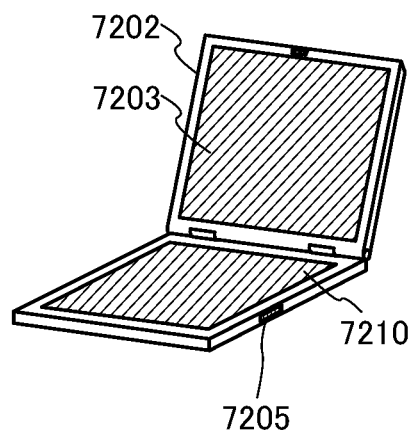

FIG. 7A illustrates an example of a television device. In the television device, a display portion 7103 is incorporated in a housing 7101. Here, a structure in which the housing 7101 is supported by a stand 7105 is shown. Images can be displayed on the display portion 7103, and the EL devices described in Embodiment 2 are arranged in a matrix in the display portion 7103.

The television device can be operated with an operation switch of the housing 7101 or a separate remote controller 7110. With operation keys 7109 of the remote controller 7110, channels and volume can be controlled and images displayed on the display portion 7103 can be controlled. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 7B1 is a computer which includes a main body 7201, a housing 7202, a display portion 7203, a keyboard 7204, an external connection port 7205, a pointing device 7206, and the like. Note that this computer is fabricated using the EL devices described in Embodiment 2 arranged in a matrix in the display portion 7203. The computer in FIG. 7B1 may be such a mode as illustrated in FIG. 7B2. The computer in FIG. 7B2 is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

Figure 7C:
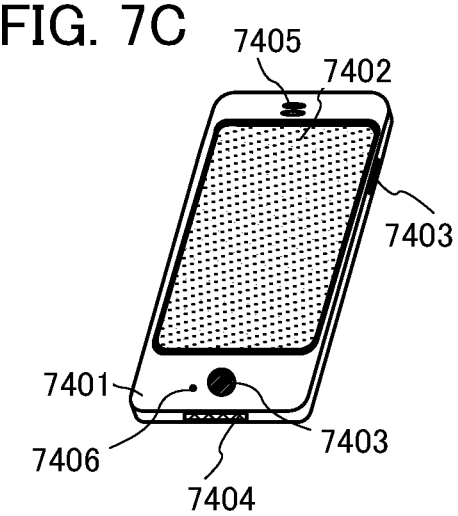

FIG. 7C illustrates an example of a portable terminal. A mobile phone includes operation buttons 7403, an external connection port 7404, a speaker 7405, a microphone 7406, and the like in addition to a display portion 7402 incorporated in a housing 7401. Note that a mobile phone includes the display portion 7402 which is fabricated by arranging the EL devices described in Embodiment 2 in a matrix.

The portable terminal illustrated in FIG. 7C may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Note that the structures described in this embodiment can be combined with the structures described in Embodiment 2 to Embodiment 4 as appropriate.

As described above, the application range of the light-emitting apparatus including the EL device described in Embodiment 2 is wide so that this light-emitting apparatus can be applied to electronic devices in a variety of fields. With the use of the EL device described in Embodiment 2, an electronic device with low power consumption can be obtained.

Figure 8A:
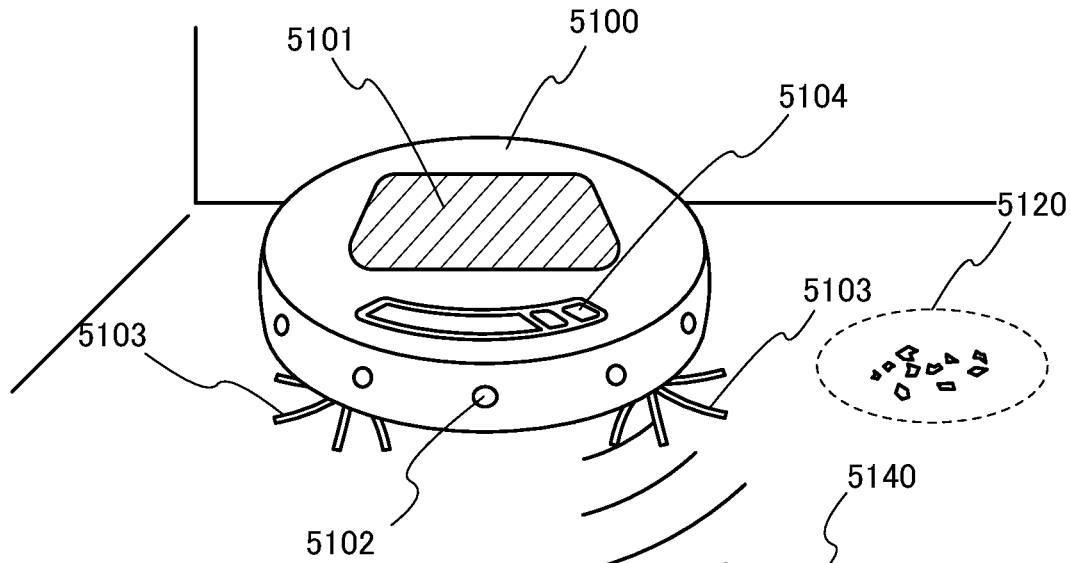
FIG. 8A to FIG. 8C are diagrams illustrating electronic devices.

FIG. 8A is a schematic view illustrating an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device such as a smartphone.

The light-emitting apparatus described in Embodiment 3 can be used for the display 5101.

Figure 8B:
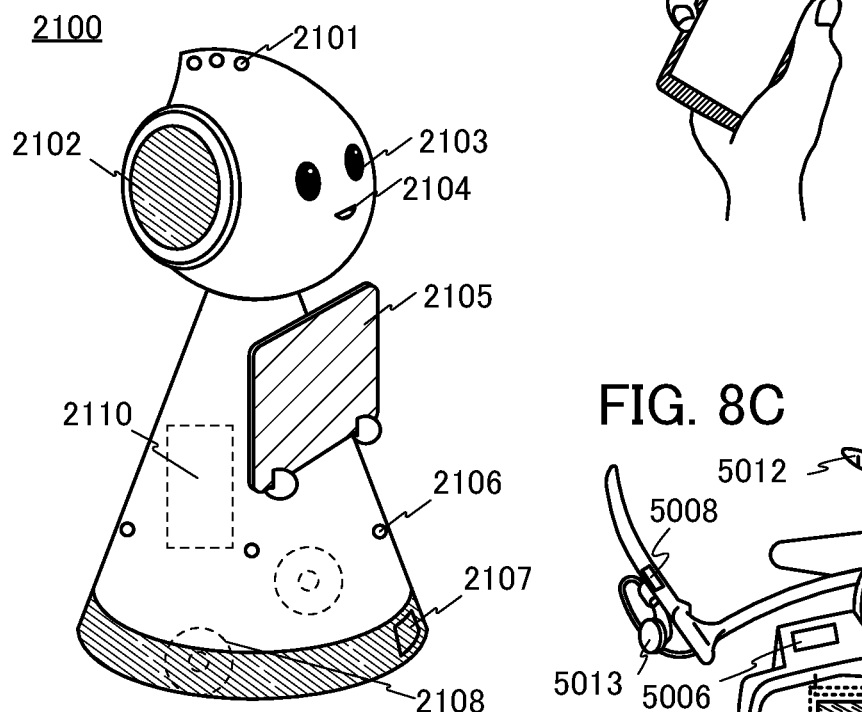

A robot 2100 illustrated in FIG. 8B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus described in Embodiment 3 can be used for the display 2105.

Figure 8C:
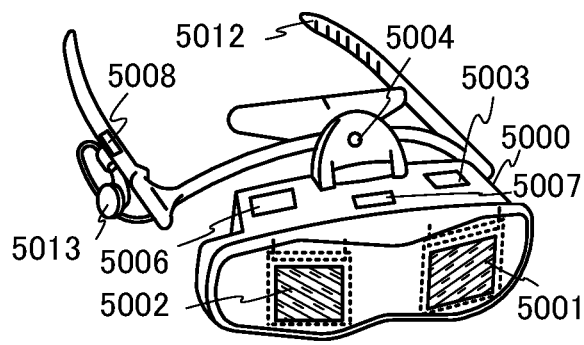

FIG. 8C shows an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a display portion 5002, a support 5012, and an earphone 5013.

The light-emitting apparatus described in Embodiment 3 can be used for the display portion 5001 and the second display portion 5002.

Figure 9:
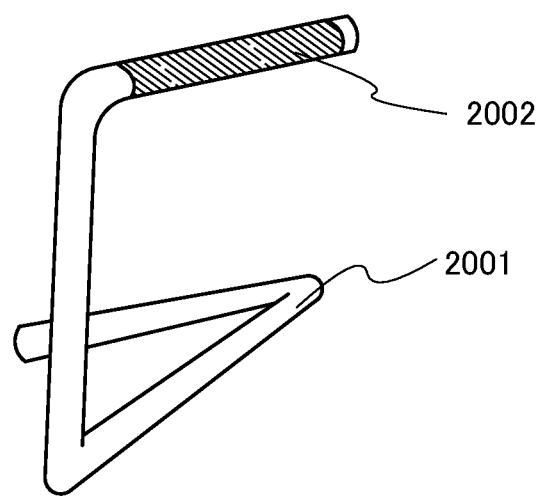
FIG. 9 is a diagram illustrating a lighting device.

FIG. 9 illustrates an example in which the EL device described in Embodiment 2 is used for a table lamp which is a lighting device. The table lamp illustrated in FIG. 9 includes a housing 2001 and a light source 2002, and the lighting device described in Embodiment 3 may be used for the light source 2002.

Figure 10:
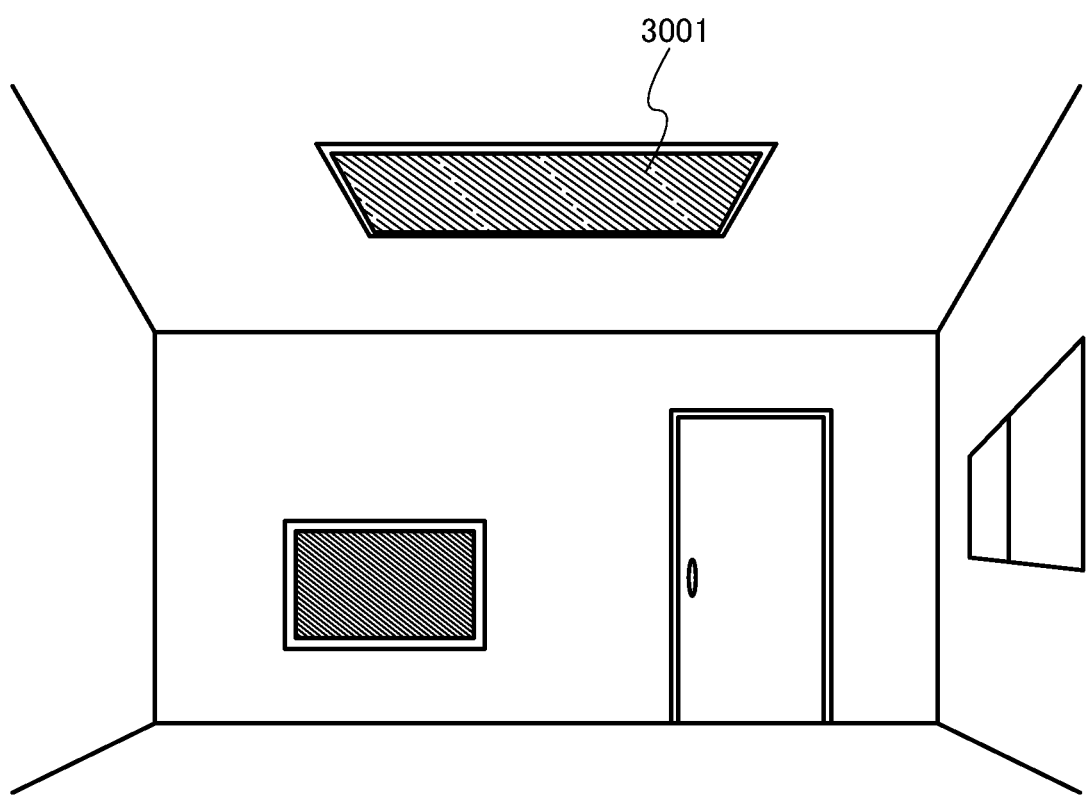
FIG. 10 is a diagram illustrating a lighting device.

FIG. 10 illustrates an example in which the EL device described in Embodiment 2 is used for an indoor lighting device 3001. Since the EL device described in Embodiment 2 is an EL device having high emission efficiency, the lighting device can have low power consumption. Furthermore, the EL device described in Embodiment 2 can have a larger area, and thus can be used for a large-area lighting device. Furthermore, the EL device described in Embodiment 2 is thin, and thus can be used for a lighting device having a reduced thickness.

Figure 11:
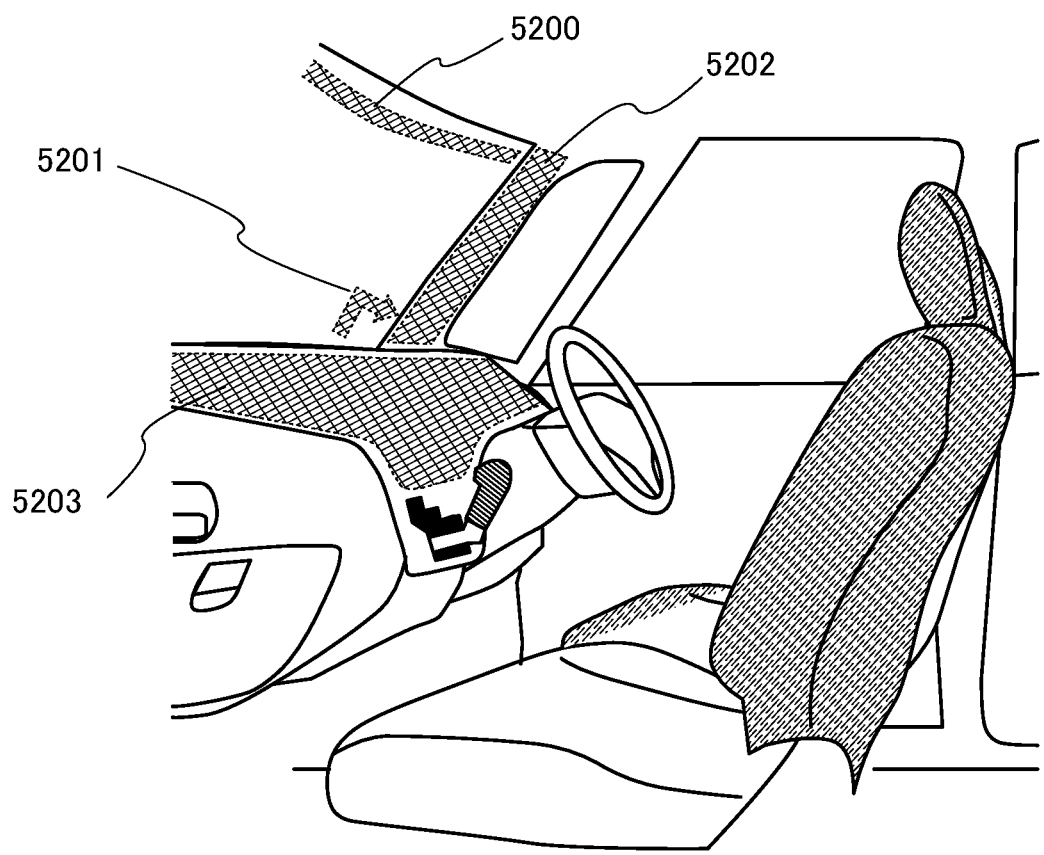
FIG. 11 is a diagram illustrating in-vehicle display devices and lighting devices.

The EL device described in Embodiment 2 can also be incorporated in an automobile windshield or an automobile dashboard. FIG. 11 illustrates one mode in which the EL device described in Embodiment 2 is used for a windshield and a dashboard of an automobile. A display region 5200 to a display region 5203 are a display region provided using the EL device described in Embodiment 2.

The display region 5200 and the display region 5201 are display devices provided in the automobile windshield, in which the EL devices described in Embodiment 2 are incorporated. When the EL devices described in Embodiment 2 are fabricated using electrodes having light-transmitting properties as an anode and a cathode, what is called see-through display devices, through which the opposite side can be seen, can be obtained. See-through display devices can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the EL devices described in Embodiment 2 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be displayed on the display region 5200 to the display region 5202. The display region 5200 to the display region 5203 can also be used as lighting devices.

Figure 12A:
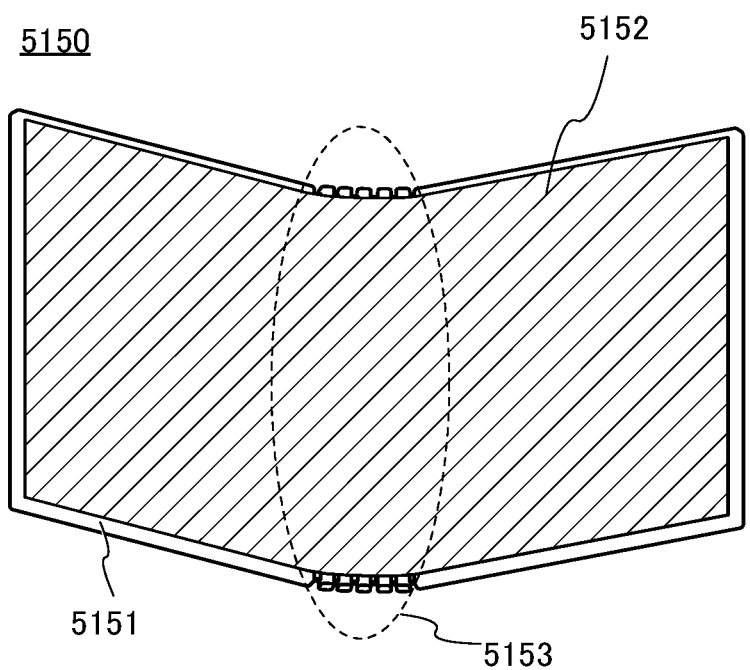
FIG. 12A and FIG. 12B are diagrams illustrating an electronic device.
Figure 12B:
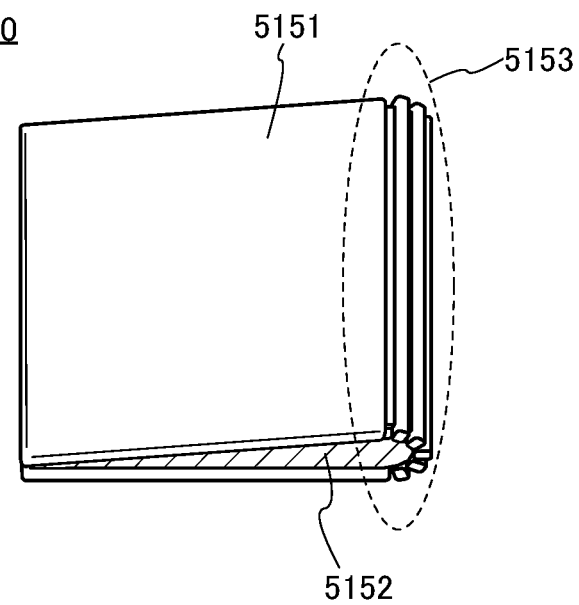

FIGS. 12A and 12B illustrate a foldable portable information terminal 5150. The foldable portable information terminal 5150 includes a housing 5151, a display region 5152, and a bend portion 5153. FIG. 12A illustrates the portable information terminal 5150 that is opened. FIG. 12B illustrates the portable information terminal 5150 that is folded. The portable information terminal 5150 is compact in size and has excellent portability when folded, despite its large display region 5152.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 3 mm or more.

Note that the display region 5152 may be a touch panel (an input/output device) including a touch sensor (an input device). The light-emitting apparatus described in Embodiment 3 can be used for the display region 5152.

Figure 13A:
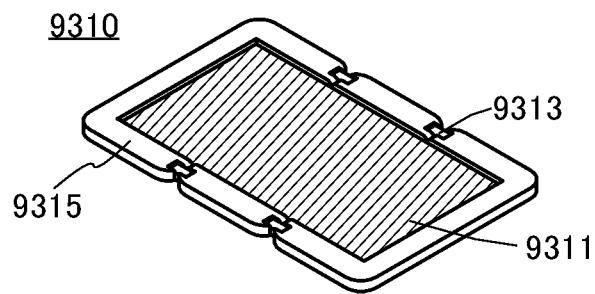
FIG. 13A to FIG. 13C are diagrams illustrating an electronic device.
Figure 13B:
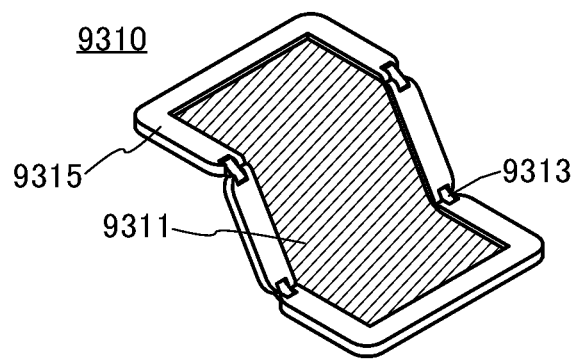
Figure 13C:
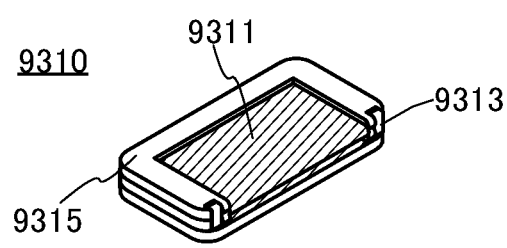

FIGS. 13A to 13C illustrate a foldable portable information terminal 9310. FIG. 13A illustrates the portable information terminal 9310 that is opened. FIG. 13B illustrates the portable information terminal 9310 which is in the state of being changed from one of an opened state and a folded state to the other. FIG. 13C illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus described in Embodiment 3 can be used for the display panel 9311.

Example 1

In this example, an EL device 1 and an EL device 2 which were fabricated using the composition for an EL device of one embodiment of the present invention described in Embodiments and an EL device 3 which was fabricated using a comparative composition for an EL device will be described. Structural Formulae of organic compounds used in this example are shown below.

[Chemical Formula 17]

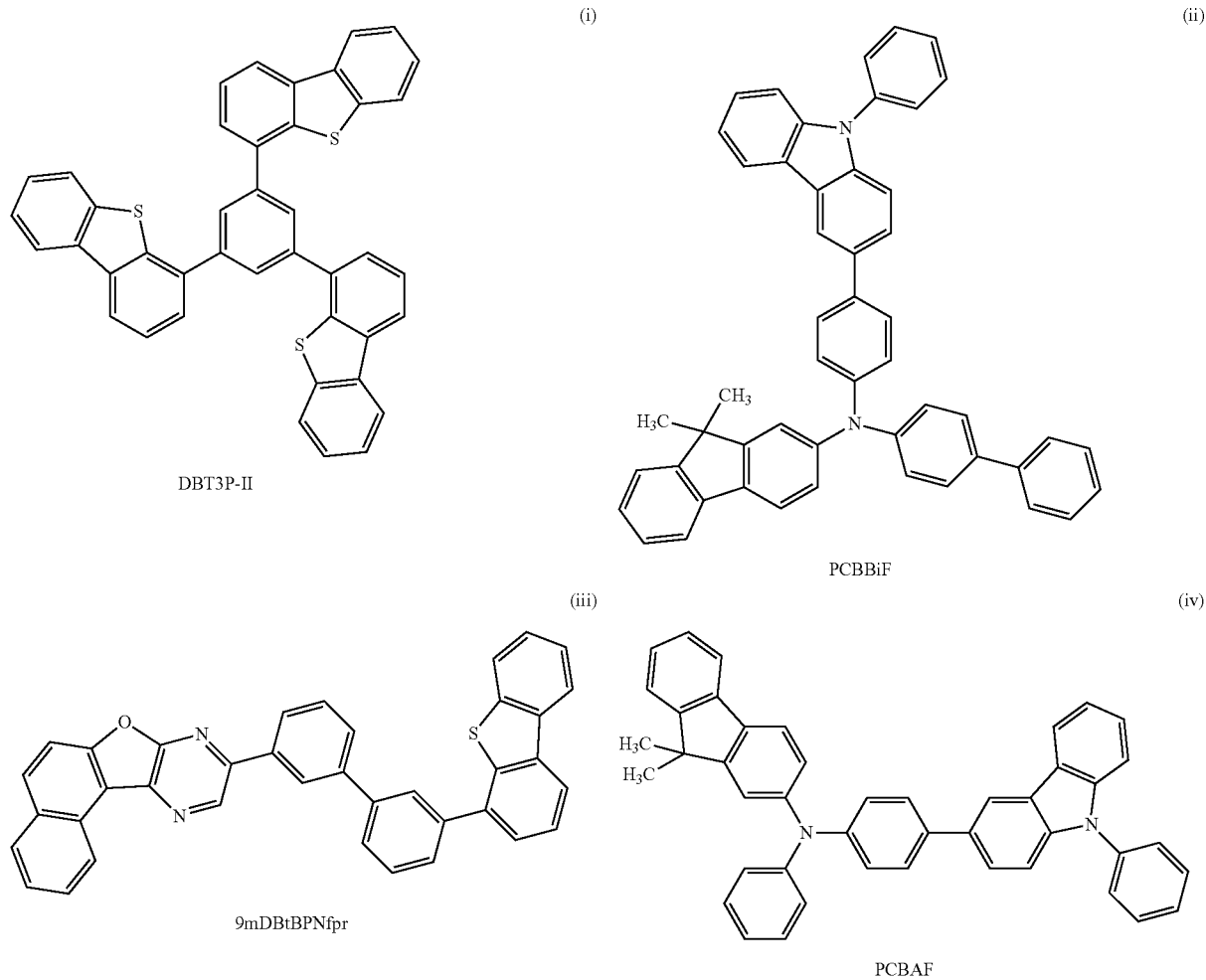

(vi)
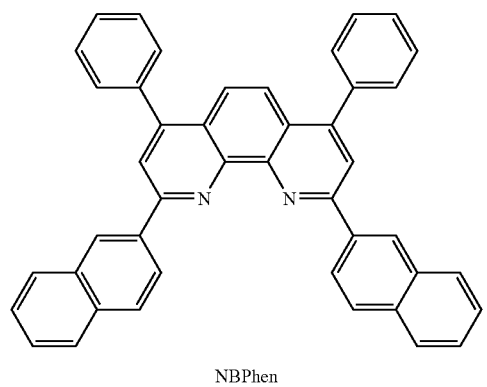
NBPhen
(v)
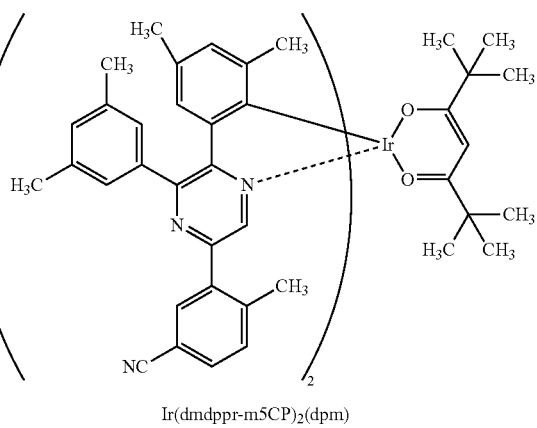
Ir(dmdppr-m5CP)₂(dpm)
(vii)
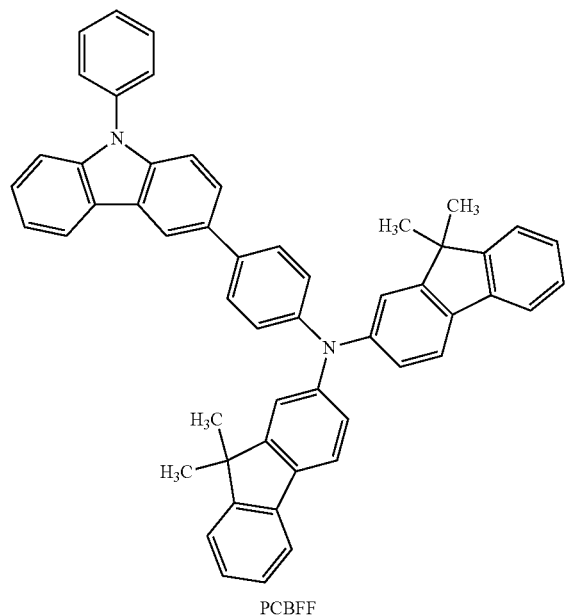
PCBFF
[Chemical Formula 18]
(i)
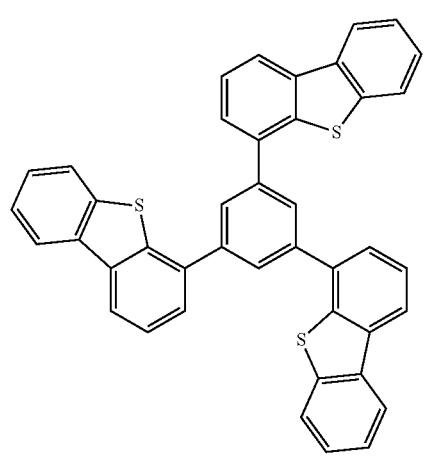
DBT3P-II -continued
(ix)
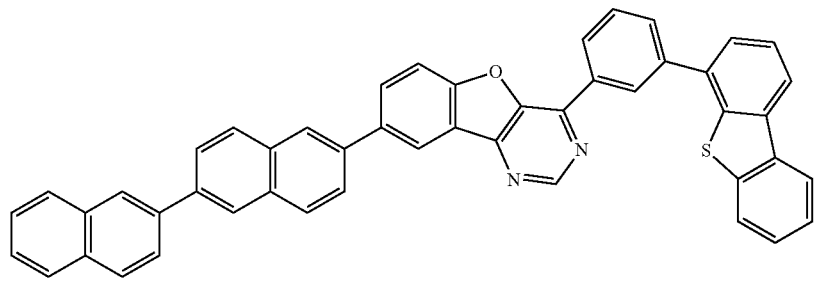
8(βN2)-4mDBtPBfpm
(viii)
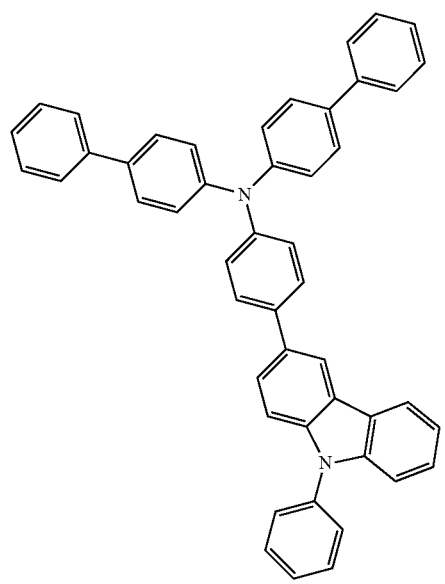
PCBBiBP
(x)
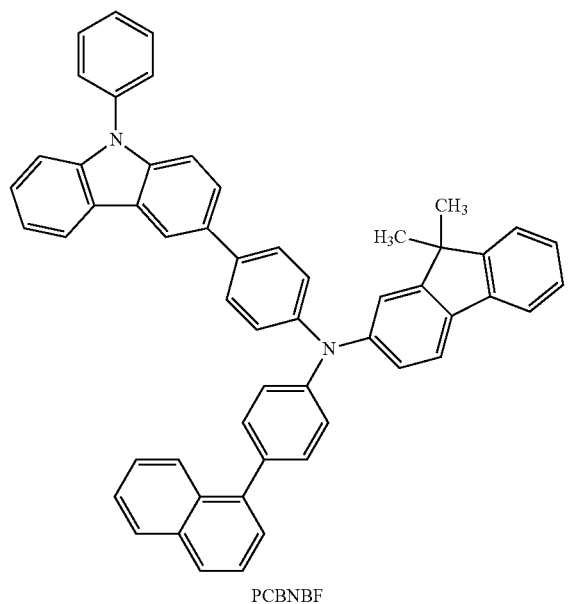
PCBNBF
(xi)
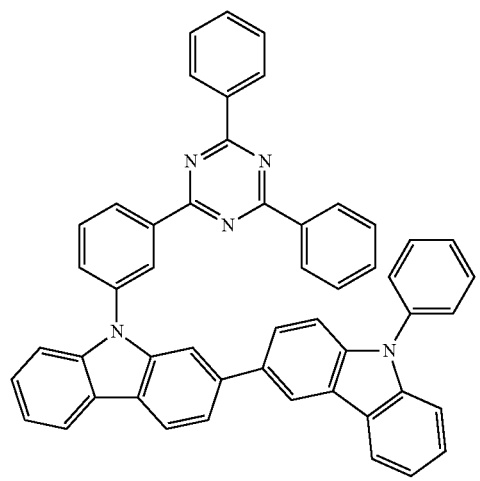
mPCCzPTzn-02
(v)
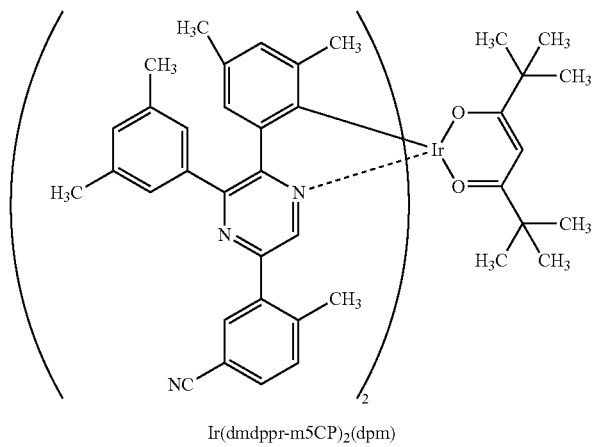
Ir(dmdppr-m5CP)$_2$(dpm)

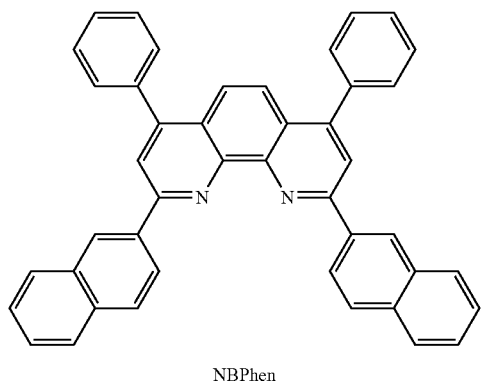

NBPhen (Method of Fabricating EL Device 1)

First, indium tin oxide containing silicon oxide (ITSO) was deposited on a glass substrate by a sputtering method to form the anode 101. Note that the film thickness was 70 nm and the area of the electrode was 2 mm×2 mm.

Next, in pretreatment for forming the EL device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate on which the anode 101 was formed was fixed to a substrate holder provided in the vacuum evaporation apparatus such that the surface on which the anode 101 was formed faced downward. On the anode 101, 4,4',4"-(benzene-1,3,5-triyl)tri(dibenzothiophene) (abbreviation: DBT3P-II) represented by Structural Formula (i) shown above and molybdenum(VI) oxide were deposited by co-evaporation to a thickness of 75 nm at a weight ratio of 2:1 (=DBT3P-II: molybdenum oxide) by an evaporation method using resistance heating, whereby the hole-injection layer 111 was formed.

Next, over the hole-injection layer 111, N-(1,1'-biphenyl-4-yl)-N-[4-(9-phenyl-9H-carbazol-3-yl)phenyl]-9,9-dimethyl-9H-fluoren-2-amine (abbreviation: PCBBiF) represented by Structural Formula (ii) was deposited by evaporation to a thickness of 20 nm; whereby the hole-transport layer 112 was formed.

Next, a composition in which 9-[(3'-dibenzothiophen-4-yl)biphenyl-3-yl]naphtho[1',2':4,5]furo[2,3-b]pyrazine (abbreviation: 9mDBtBPNfpr) represented by Structural Formula (iii) above and 9,9-dimethyl-N-phenyl-N-[4-(9-phenyl-9H-carbazol-3-yl)phenyl]fluoren-2-amine (abbreviation: PCBAF) represented by Structural Formula (iv) above are mixed in advance such that the weight ratio of 9mDBtBPNfpr to PCBAF was 0.8:0.2 and bis{4,6-dimethyl-2-[5-(5-cyano-2-methylphenyl)-3-(3,5-dimethylphenyl)-2-pyrazinyl-cN]phenyl-xC}(2,2,6,6-tetramethyl-3,5-heptanedionato-κ2O,O')iridium(III) (abbreviation: [Ir(dmdppr-m5CP)$_2$(dpm)]) represented by Structural Formula (v) above were deposited by co-evaporation to a thickness of 40 nm such that the weight ratio of [the composition in which 9mDBtBPNfpr and PCBAF are mixed] to [Ir(dmdppr-m5CP)$_2$(dpm)] was 1:0.1, whereby the light-emitting layer 113 was formed. Note that in the case of forming the light-emitting layer 113, 9mDBtBPNfpr and PCBAF were evaporated from the same evaporation source as a sample of the composition in which 9mDBtBPNfpr and PCBAF were mixed in advance.

After that, on the light-emitting layer 113, 9mDBtBPNfpr was deposited by evaporation to a thickness of 30 nm, and 2,9-bis(naphthalen-2-yl)-4,7-diphenyl-1,10-phenanthroline (abbreviation: NBPhen) represented by Structural Formula (vi) above was deposited by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the cathode 102, whereby the EL device 1 was fabricated.

As the EL devices 1, eight devices having the same stacked structure, i.e., n=1 to n=8, were fabricated in such a manner that evaporation for the light-emitting layer was successively performed without changing the sample in the evaporation source.

(Method of Fabricating EL Device 2)

The EL device 2 was fabricated in a manner similar to that for the EL device 1 except that PCBAF in the light-emitting layer of the EL device 1 was replaced with N-[4-(9-phenyl-9H-carbazol-3-yl)phenyl]-bis(9,9-dimethyl-9H-fluoren-2-yl)amine (abbreviation: PCBFF) represented by Structural Formula (vii) above. Note that in the case of forming the light-emitting layer 113, 9mDBtBPNfpr and PCBFF were evaporated from the same evaporation source as a sample of the composition in which 9mDBtBPNfpr and PCBFF were mixed in advance such that the weight ratio of 9mDBtBPNfpr to PCBFF was 0.8:0.2.

As the EL devices 2, eight devices having the same stacked structure, i.e., n=1 to n=8, were fabricated in such a manner that evaporation for the light-emitting layer was successively performed without changing the sample in the evaporation source.

(Method of Fabricating EL Device 3)

The EL device 3 was fabricated in a manner similar to that for the EL device 1 except that PCBBiF in the hole-transport layer 112 of the EL device 1 was replaced with 4,4'-diphenyl-4"-(9-phenyl-9H-carbazol-3-yl)triphenylamine (abbreviation: PCBBi1BP) represented by Structural Formula (viii) above; the light-emitting layer 113 was formed in the following manner: a composition in which 8-(2,2'-binaphthyl-6-yl)-4-[3-(dibenzothiophen-4-yl)phenyl-[1]

benzofuro[3,2-d]pyrimidine (abbreviation: 8(βN2)-4mDBtPBfpm) represented by Structural Formula (ix) above and 9,9-dimethyl-N-[4-(1-naphthyl)phenyl]-N-[4-(9-phenyl-9H-carbazol-3-yl)phenyl]-9H-fluoren-2-amine (abbreviation: PCBNBF) represented by Structural Formula (x) above were mixed in advance such that the weight ratio of 8(βN2)-4mDBtPBfpm to PCBNBF was 0.7:0.3 and [Ir(dmdppr-m5CP)$_2$(dpm)]) were deposited by co-evaporation to a thickness of 40 nm such that the weight ratio of [the composition in which 8(βN2)-4mDBtPBfpm and PCBNBF are mixed] to [Ir(dmdppr-m5CP)$_2$(dpm)] was 1:0.1; and 9mDBtBPNfpr in the electron-transport layer 114 was replaced with 9-[3-(4,6-diphenyl-1,3,5-triazin-2-yl)phenyl]-9'-phenyl-2,3'-bi-9H-carbazole (abbreviation: mPCCzPTzn-02) represented by Structural Formula (xi) above. Note that in the case of forming the light-emitting layer 113, 8(βN2)-4mDBtPBfpm and PCBNBF were evaporated from the same evaporation source as a sample of the composition in which 8(βN2)-4mDBtPBfpm and PCBNBF were mixed in advance.

As the EL devices 3, five devices having the same stacked structure, i.e., n=1 to n=5, were fabricated in such a manner that evaporation for the light-emitting layer was successively performed without changing the sample in the evaporation source.

The device structures of the EL device 1 to the EL device 3 are listed in the following table.

TABLE 1

| | Hole-injection layer 75 nm | Hole-transport layer 20 nm | Light-emitting layer 40 nm | Electron-transport layer | | Electron-injection layer 1 nm |
| --- | --- | --- | --- | --- | --- | --- |
| | | | | 1 30 nm | 2 15 nm | |
| EL device 1 | DBT3P-II: MoOx (2:1) | PCBBiF | *1 | 9mDBtBPNfpr | NBPhen | LiF |
| EL device 2 | | | *2 | | | |
| EL device 3 | | PCBBi1BP | *3 | mPCCzPTzn-02 | | |

*1 9mDBtBPNfpr:PCBAF: [Ir(dmdppr-m5CP)$_2$(dpm)] (0.8:0.2:0.10)
*2 9mDBtBPNfpr:PCBFF: [Ir(dmdppr-m5CP)$_2$(dpm)] (0.8:0.2:0.10)
*3 8(βN2)-4mDBtPBfpm:PCBNBF: [Ir(dmdppr-m5CP)$_2$(dpm)] (0.7:0.3:0.10)

Here, Table 2 shows measurement results of 5% weight loss temperatures in a vacuum (approximately $1 \times 10^{-2}$ Pa) of two kinds of organic compounds for each device used as a composition mixed in advance when the light-emitting layers 113 of the EL device 1 to the EL device 3 were formed by evaporation. The 5% weight loss temperature was obtained from the relation between weight and temperature (thermogravimetric measurement) by performing thermogravimetry-differential thermal analysis (TG-DTA). The measurement was performed using a high vacuum differential type differential thermal balance (TG-DTA2410SA, produced by Bruker AXS K.K.).

TABLE 2

| | | 5 % weight loss temperature (° C.) | Difference (° C.) |
| --- | --- | --- | --- |
| EL device 1 | 9mDBtBPNfpr | 297 | 43 |
| | PCBAF | 254 | |
| EL device 2 | 9mDBtBPNfpr | 297 | 21 |
| | PCBFF | 276 | |
| EL device 3 | 8(βN2)-4mDBtPBfpm | 342 | 66 |
| | PCBNBF | 276 | |

As shown in Table 2, the 5% weight loss temperature of the organic compound included in the sample of the composition mixed in advance was as follows: the EL device 1, 43° C.; the EL device 2, 21° C.; and the EL device 3, 66° C.

These EL devices were subjected to sealing with a glass substrate (a sealant was applied to surround the devices, and at the time of sealing, UV treatment was performed first and heat treatment was performed at 80° C. for an hour) in a glove box containing a nitrogen atmosphere so that the EL devices were not exposed to the air. Then, the initial characteristics and reliability were measured. Note that luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.).

Figure 15:
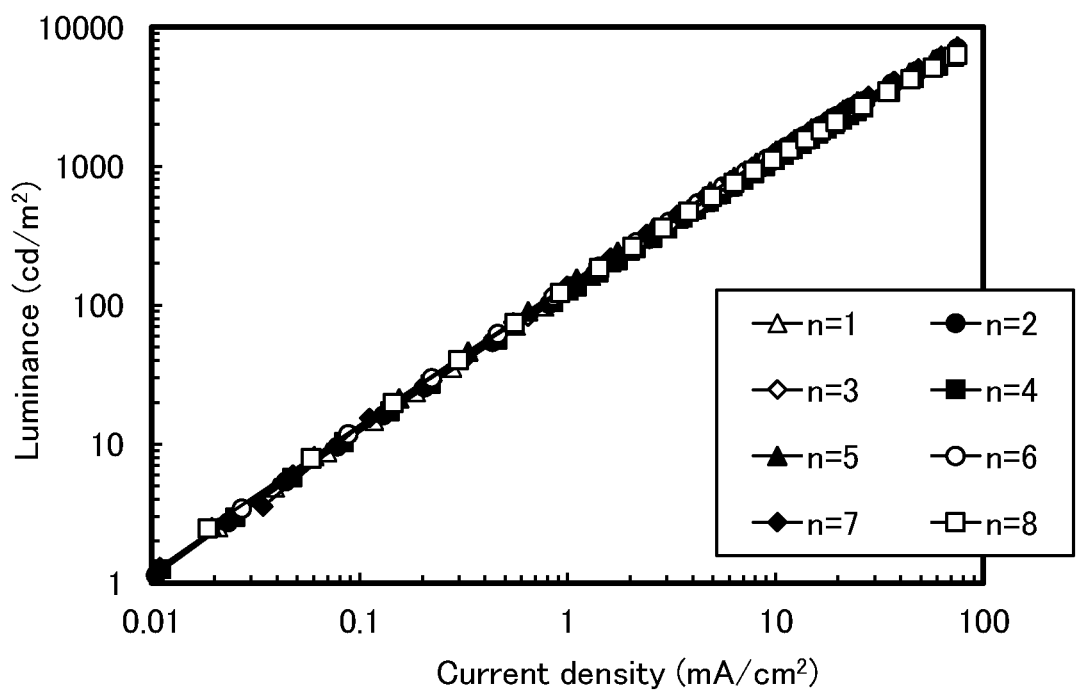
FIG. 15 is a graph showing luminance-current density characteristics of EL devices 1.
Figure 16:
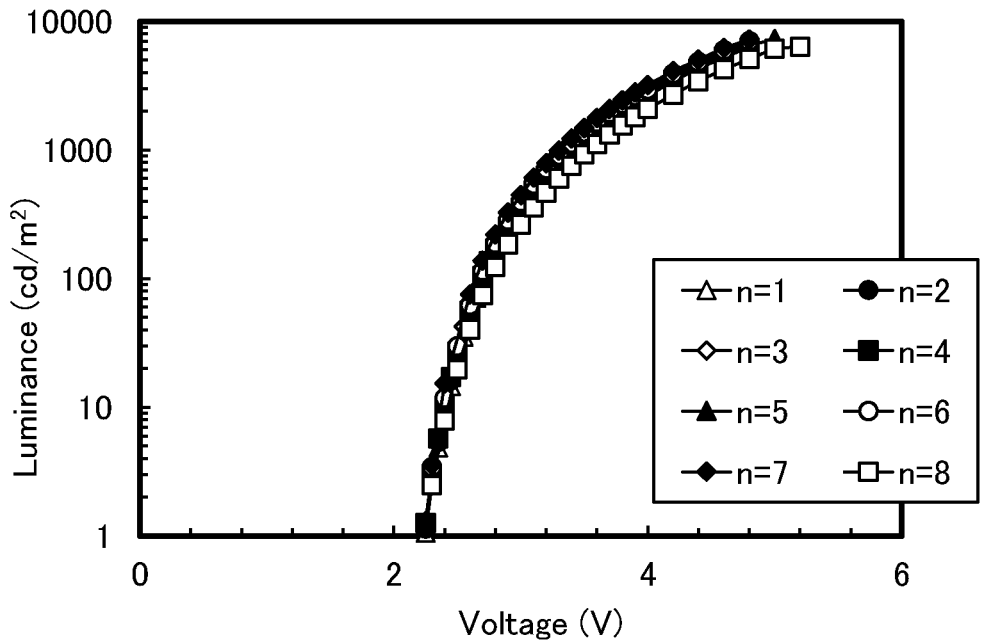
FIG. 16 is a graph showing luminance-voltage characteristics of the EL devices 1.
Figure 17:
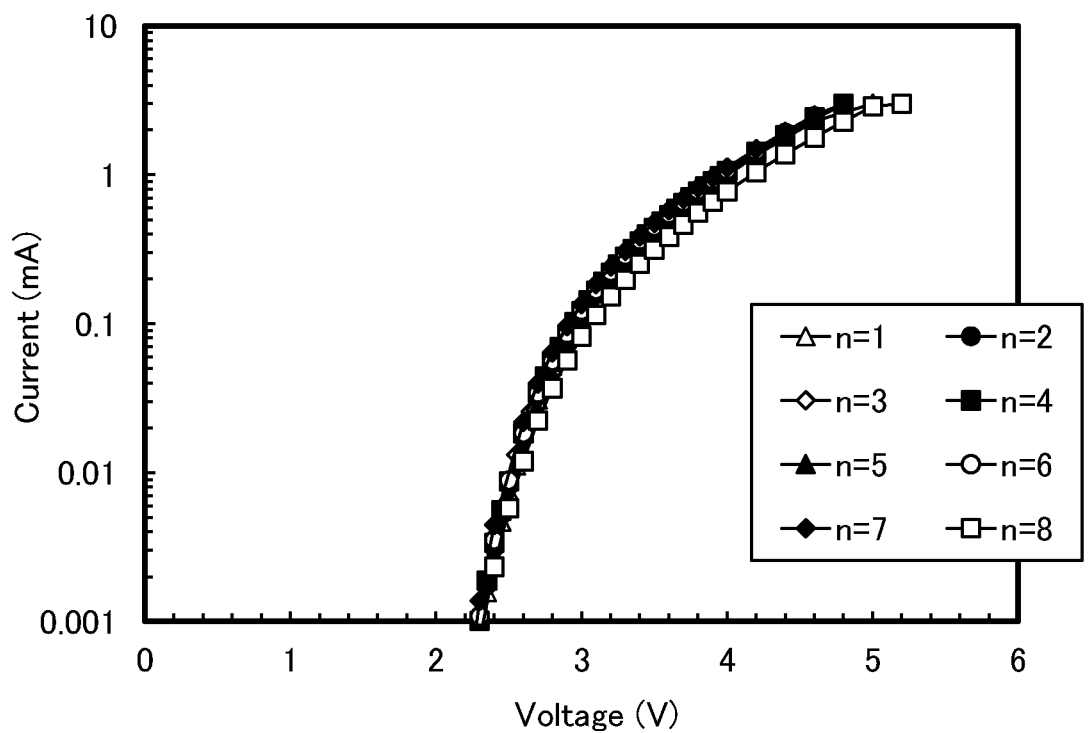
FIG. 17 is a graph showing current-voltage characteristics of the EL devices 1.
Figure 18:
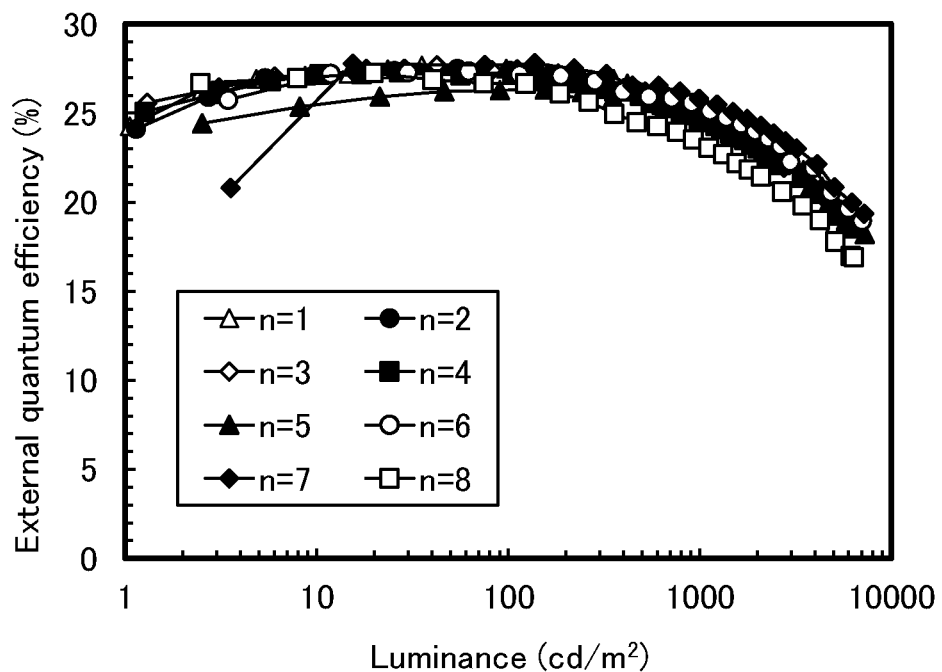
FIG. 18 is a graph showing external quantum efficiency-luminance characteristics of the EL devices 1.
Figure 19:
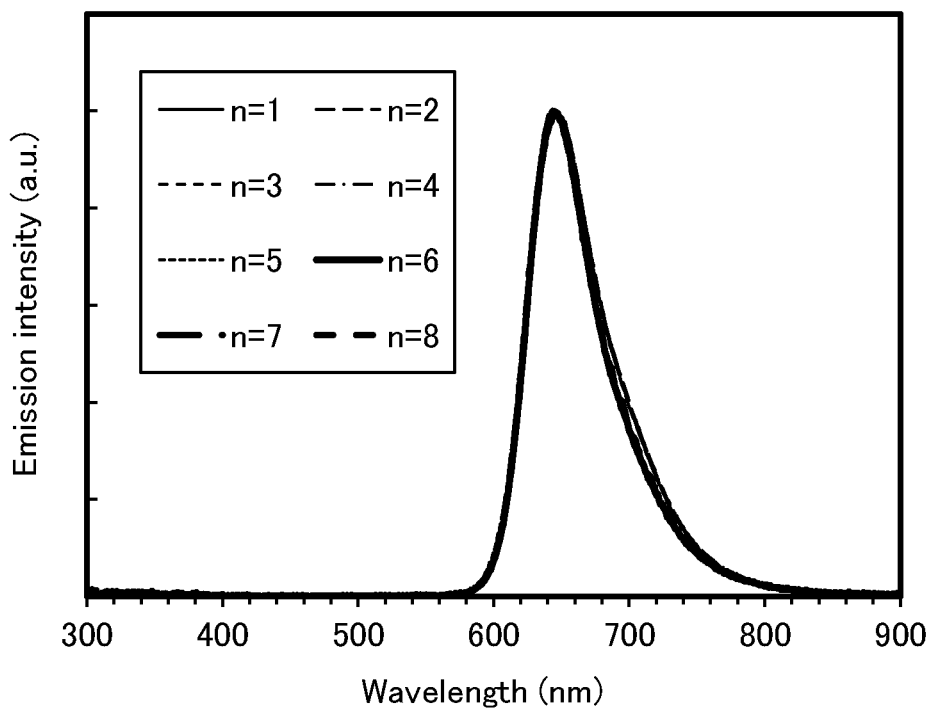
FIG. 19 is a graph showing emission spectra of the EL devices 1.
Figure 20:
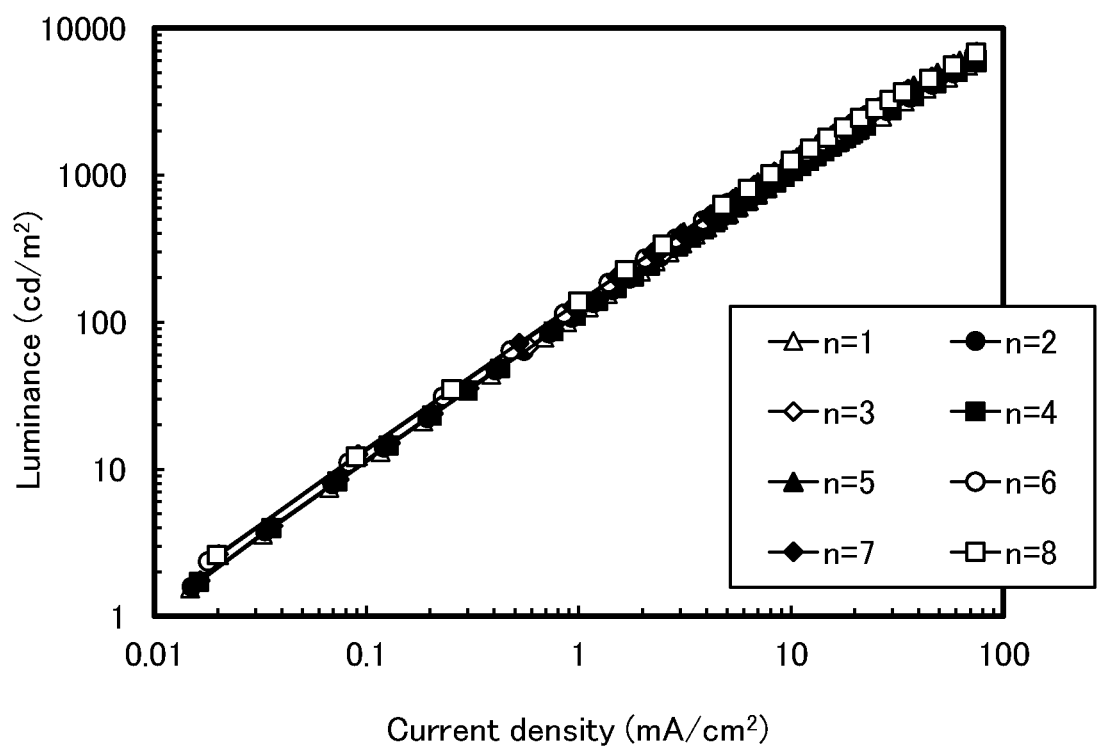
FIG. 20 is a graph showing luminance-current density characteristics of EL devices 2.
Figure 21:
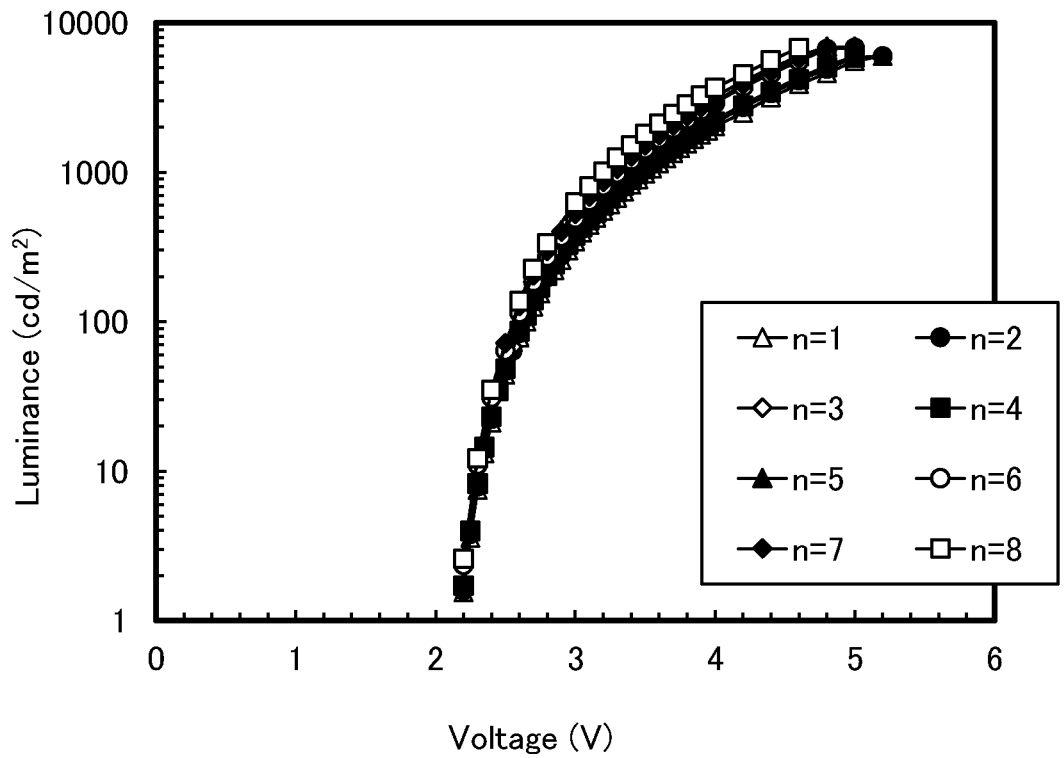
FIG. 21 is a graph showing luminance-voltage characteristics of the EL devices 2.
Figure 22:
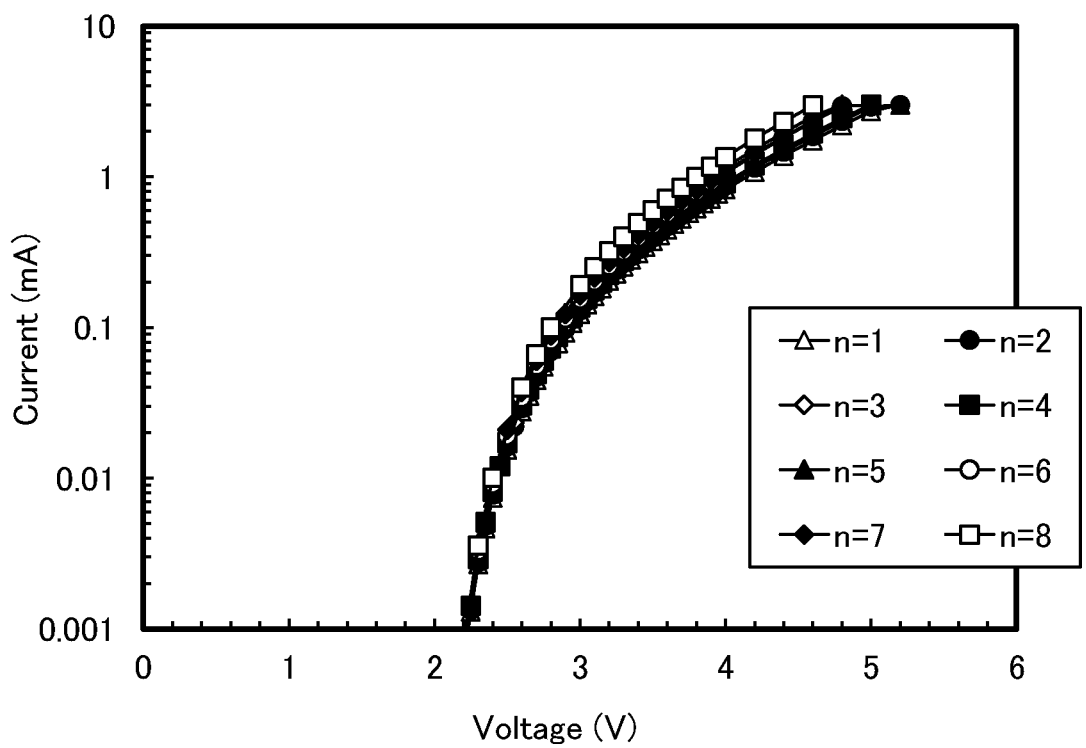
FIG. 22 is a graph showing current-voltage characteristics of the EL devices 2.
Figure 23:
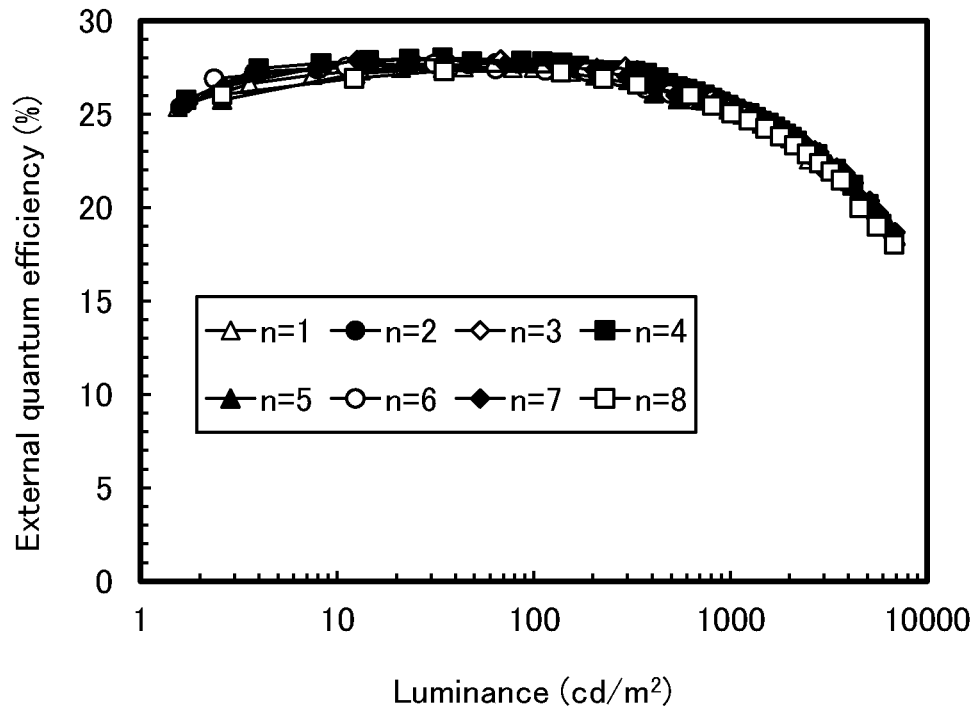
FIG. 23 is a graph showing external quantum efficiency-luminance characteristics of the EL devices 2.
Figure 24:
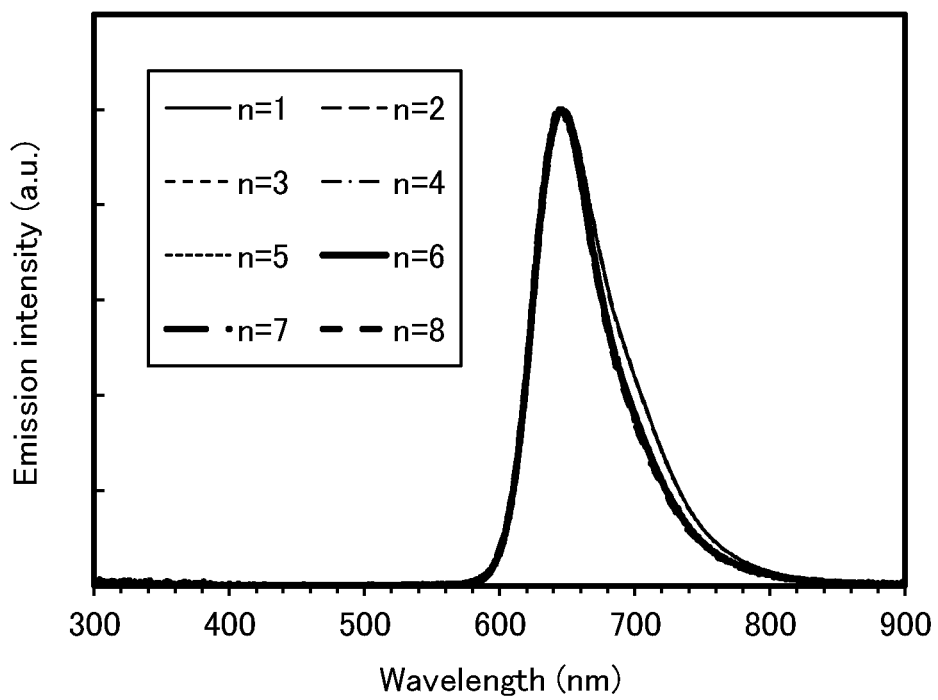
FIG. 24 is a graph showing emission spectra of the EL devices 2.
Figure 25:
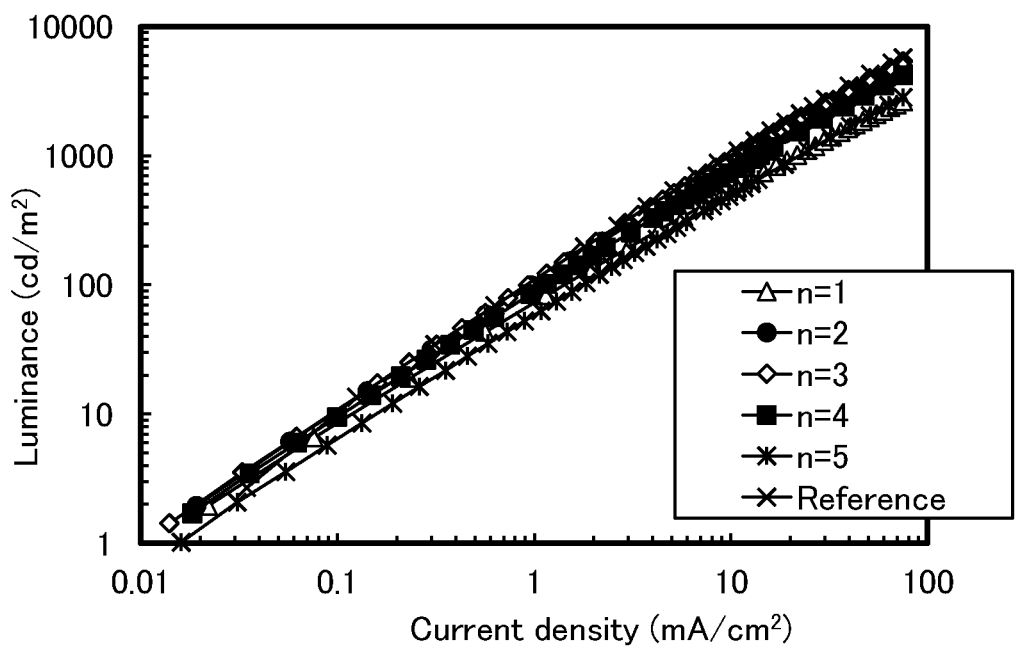
FIG. 25 is a graph showing luminance-current density characteristics of EL devices 3.
Figure 26:
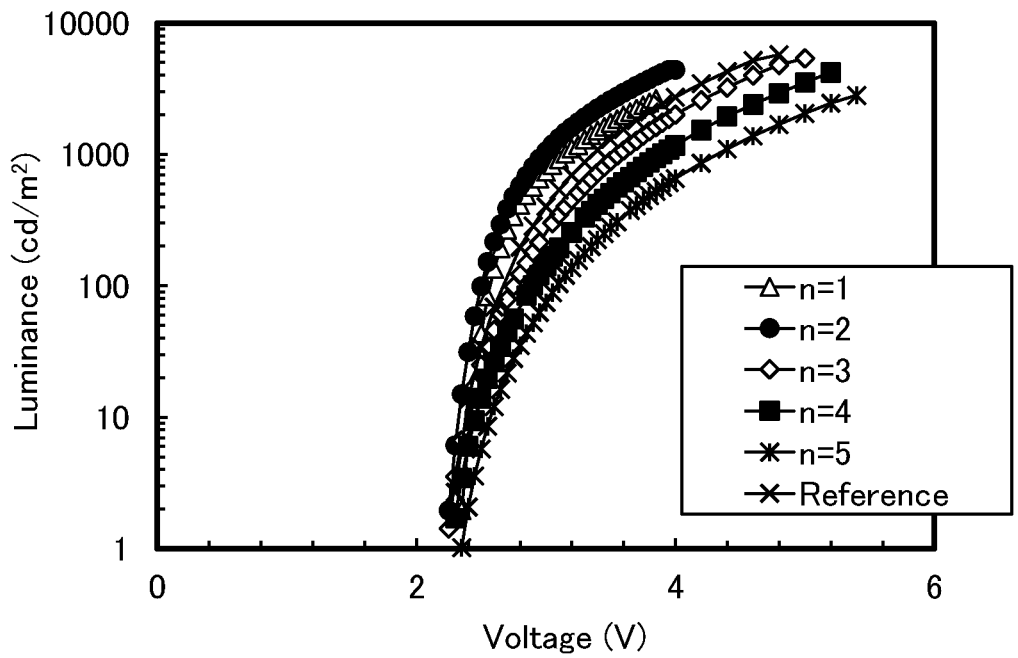
FIG. 26 is a graph showing luminance-voltage characteristics of the EL devices 3.
Figure 27:
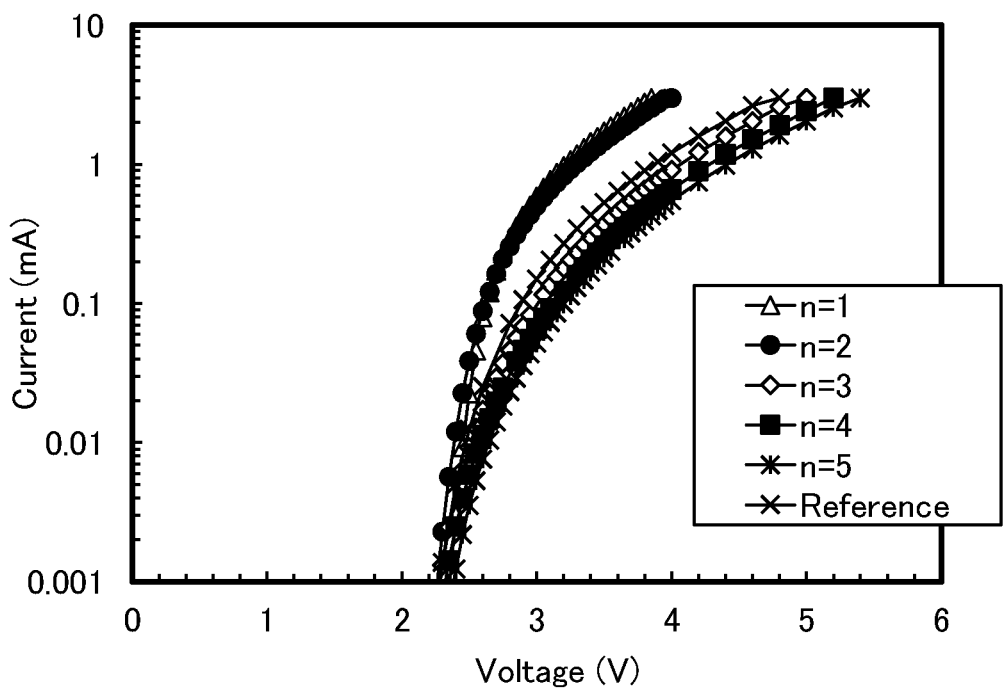
FIG. 27 is a graph showing current-voltage characteristics of the EL devices 3.
Figure 28:
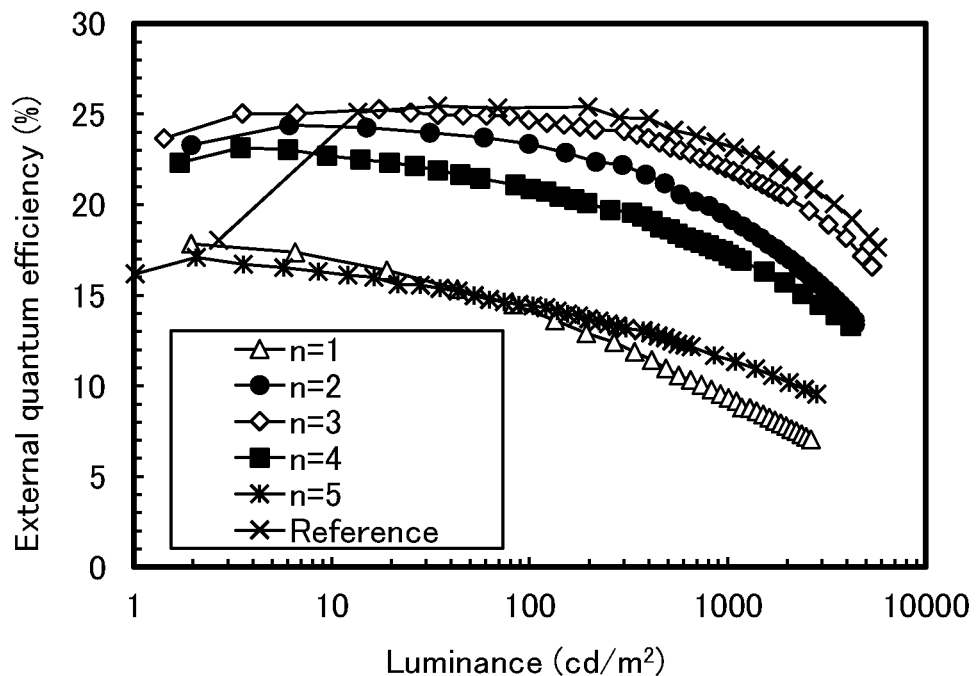
FIG. 28 is a graph showing external quantum efficiency-luminance characteristics of the EL devices 3.
Figure 29:
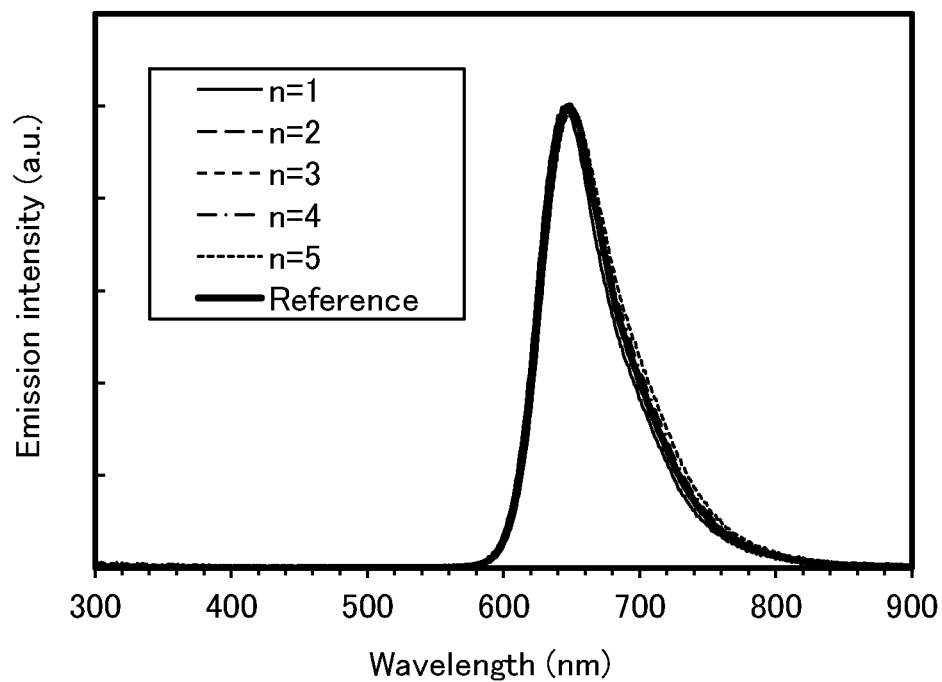
FIG. 29 is a graph showing emission spectra of the EL devices 3.

FIG. 15 shows the luminance-current density characteristics of the EL devices 1, FIG. 16 shows the luminance-voltage characteristics thereof, FIG. 17 shows the current-voltage characteristics thereof, FIG. 18 shows the external quantum efficiency-luminance characteristics thereof, FIG. 19 shows the emission spectra; FIG. 20 shows the luminance-current density characteristics of the EL devices 2, FIG. 21 shows the luminance-voltage characteristics thereof, FIG. 22 shows the current-voltage characteristics thereof, FIG. 23 shows the external quantum efficiency-luminance characteristics thereof, FIG. 24 shows the emission spectra thereof; FIG. 25 shows the luminance-current density characteristics of the EL devices 3, FIG. 26 shows the luminance-voltage characteristics thereof, FIG. 27 shows the current-voltage characteristics thereof, FIG. 28 shows the external quantum efficiency-luminance characteristics thereof, and FIG. 29 shows the emission spectra thereof.

The following table shows the main characteristics of the EL devices at a luminance of approximately 1000 cd/cm$^2$. In addition to the characteristics of the above-described devices, the table also shows the characteristics of reference devices for which evaporation was performed using different evaporation sources.

TABLE 3

| Device | | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|---|
| 1 | n = 1 | 3.4 | 0.35 | 8.6 | 0.71 | 0.29 | 11.5 | 25.1 |
| | n = 2 | 3.4 | 0.35 | 8.7 | 0.71 | 0.29 | 11.3 | 24.8 |
| | n = 3 | 3.4 | 0.32 | 8.1 | 0.71 | 0.29 | 11.7 | 25.2 |
| | n = 4 | 3.4 | 0.36 | 8.9 | 0.71 | 0.29 | 11.1 | 24.6 |
| | n = 5 | 3.4 | 0.32 | 8.1 | 0.70 | 0.30 | 13.1 | 24.6 |
| | n = 6 | 3.3 | 0.29 | 7.2 | 0.71 | 0.29 | 12.6 | 25.6 |
| | n = 7 | 3.3 | 0.31 | 7.7 | 0.71 | 0.29 | 12.9 | 25.8 |
| | n = 8 | 3.5 | 0.31 | 7.8 | 0.71 | 0.29 | 11.8 | 23.5 |
| | Reference | 3.7 | 0.41 | 10.2 | 0.71 | 0.29 | 10.1 | 23.8 |
| 2 | n = 1 | 3.5 | 0.37 | 9.4 | 0.71 | 0.29 | 10.4 | 25.3 |
| | n = 2 | 3.5 | 0.39 | 9.9 | 0.71 | 0.29 | 10.5 | 25.3 |
| | n = 3 | 3.5 | 0.38 | 9.4 | 0.71 | 0.29 | 10.6 | 25.5 |
| | n = 4 | 3.5 | 0.37 | 9.4 | 0.71 | 0.29 | 10.4 | 25.5 |
| | n = 5 | 3.2 | 0.28 | 7.0 | 0.71 | 0.29 | 12.7 | 25.5 |
| | n = 6 | 3.3 | 0.32 | 8.0 | 0.71 | 0.29 | 12.4 | 25.3 |
| | n = 7 | 3.3 | 0.33 | 8.4 | 0.71 | 0.29 | 12.6 | 25.4 |
| | n = 8 | 3.2 | 0.32 | 8.0 | 0.71 | 0.29 | 12.7 | 25.1 |
| | Reference | 3.5 | 0.41 | 10.3 | 0.71 | 0.29 | 10.0 | 23.8 |
| 3 | n = 1 | 3.2 | 0.87 | 21.7 | 0.70 | 0.30 | 4.7 | 9.3 |
| | n = 2 | 3.0 | 0.50 | 12.6 | 0.71 | 0.29 | 8.4 | 19.2 |
| | n = 3 | 3.6 | 0.41 | 10.3 | 0.71 | 0.29 | 9.5 | 22.0 |
| | n = 4 | 3.9 | 0.56 | 14.0 | 0.71 | 0.29 | 7.2 | 17.2 |
| | n = 5 | 4.4 | 0.99 | 24.6 | 0.71 | 0.29 | 4.5 | 11.3 |
| | Reference | 3.4 | 0.43 | 10.8 | 0.71 | 0.29 | 10.0 | 23.1 |

It was found from FIG. 15 to FIG. 29 and Table 3 that the EL devices 1 and the EL devices 2 had comparably favorable initial characteristics. In contrast, the EL devices 3 had large variations in characteristics.

Figure 30:
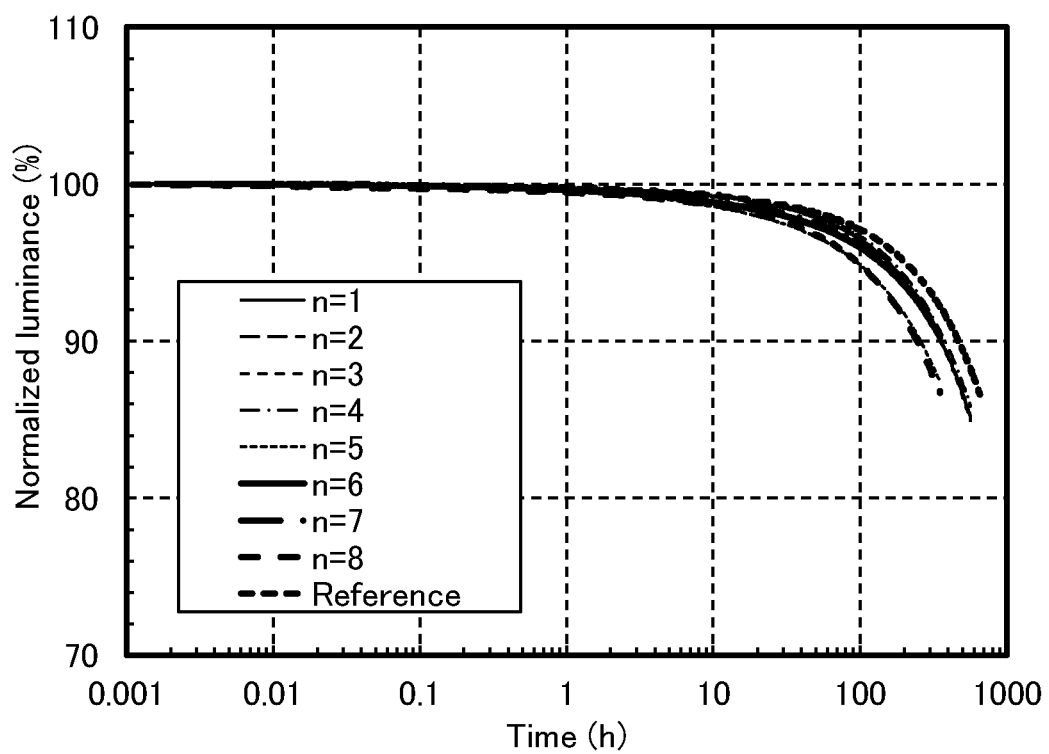
FIG. 30 is a graph showing luminance-time change characteristics of the EL devices 1.
Figure 31:
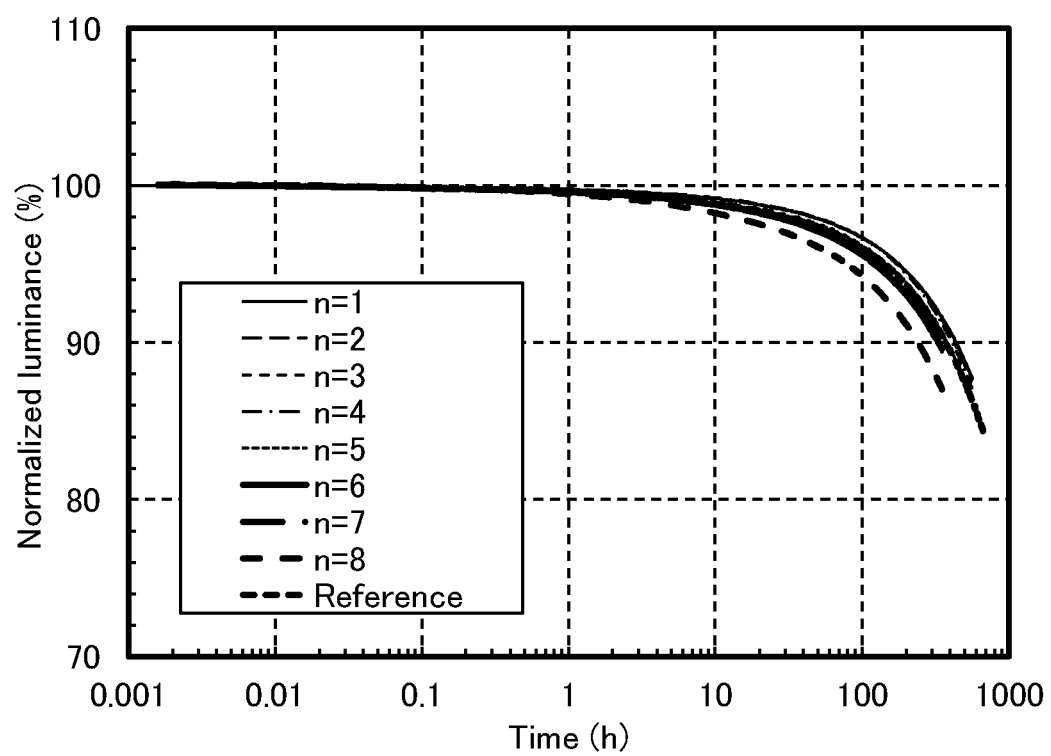
FIG. 31 is a graph showing luminance-time change characteristics of the EL devices 2.
Figure 32:
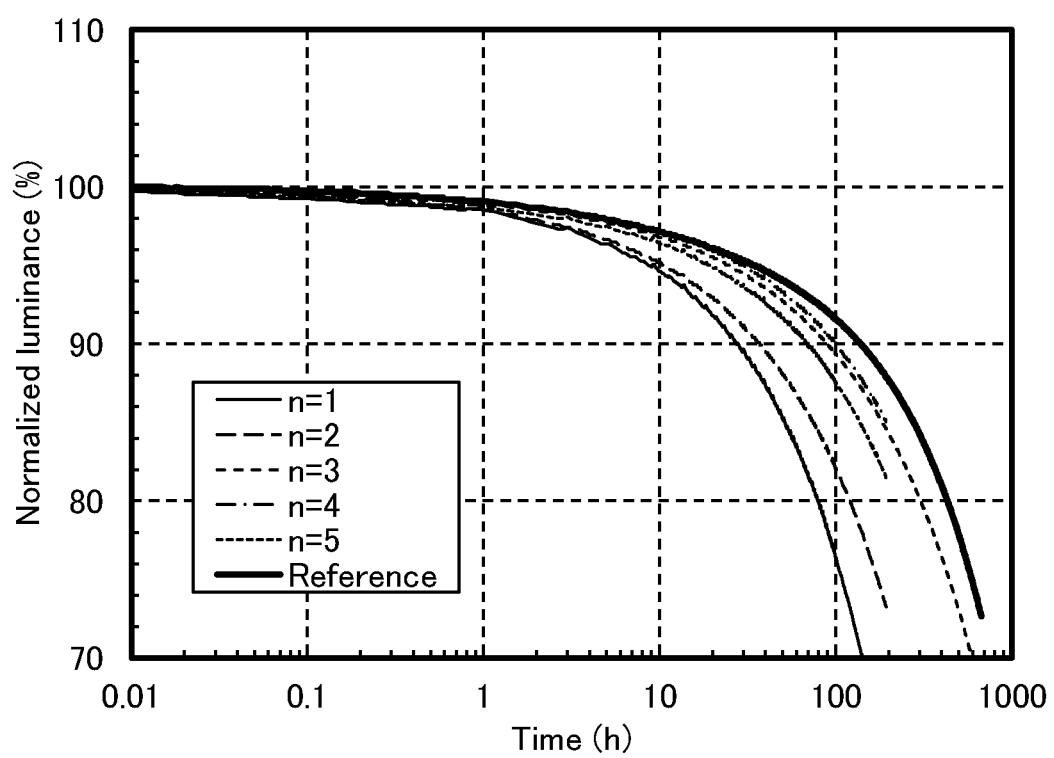
FIG. 32 is a graph showing luminance-time change characteristics of the EL devices 3.
Figure 39:
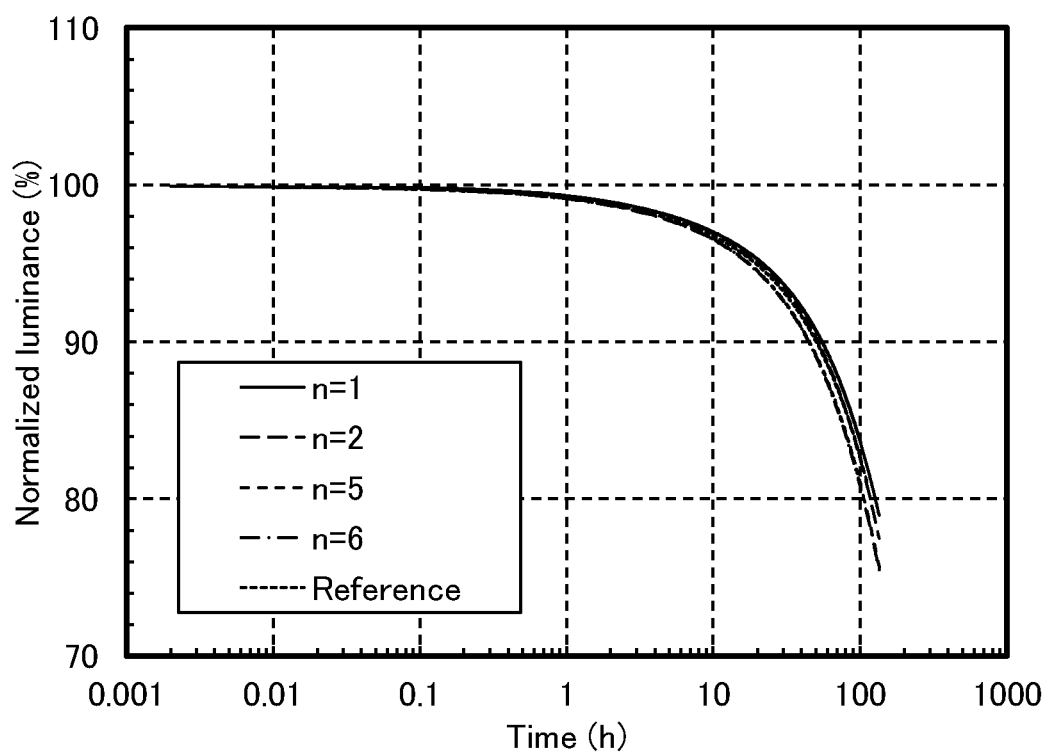
FIG. 39 is a graph showing luminance-time change characteristics of the EL devices 2 at a high temperature.

FIG. 30 to FIG. 32 and FIG. 39 are graphs each showing a change in luminance over driving time at a current density of 75 mA/cm$^2$. FIG. 30 shows the results of the EL devices 1, FIG. 31 and FIG. 39 show the results of the EL devices 2, and FIG. 32 shows the results of the EL devices 3. Note that FIG. 39 is a graph showing the change in luminance over the driving time at a high temperature of 85° C. These results show that the EL devices 1 and the EL devices 2 had comparably favorable lifetimes. In contrast, the EL devices 3 had large variations in lifetime and had unstable device characteristics.

It was found from FIG. 30 to FIG. 32 that the EL devices 1 and the EL devices 2, which were manufactured with use of the compositions of one embodiment of the present invention in each of which the 5% weight loss temperature in high vacuum between the two kinds of materials in the composition serving as an evaporation sample is 50° C. or lower, are EL devices whose deterioration in characteristics due to repeated evaporation is small. In contrast, it was found that the EL devices 3, in which a difference in the 5% weight loss temperature in high vacuum between materials in the composition serving as an evaporation sample is 66° C., are EL devices in which deterioration and variations in characteristics are large.

Here, shown are measurement results of the composition of 9mDBtBPNfpr and PCBFF in the light-emitting layers in the EL devices 2 where n=1 to n=4 among a group of the EL devices 2 which exhibited favorable characteristics. As measurement samples, the EL devices 2 where n=1 to n=4 and a reference device with a size of 2 mm×2 mm dissolved in 40 μl of a mixed solvent (acetonitrile:chloroform=7:3) were used. For measurement of the reference, 0.5 mg of a sample in which 9mDBtBPNfpr and PCBFF were mixed such that the weight ratio of 9mDBtBPNfpr to PCBFF before evaporation was 0.8:0.2 was dissolved in 2 ml of chloroform, and diluted five times with acetonitrile. Furthermore, the samples remained in the evaporation sources after fabrication of the EL devices were also measured as well as the samples before the evaporation.

The measurement was performed with ACQUITY UPLC (registered trademark) manufactured by Waters Corporation. ACQUITY UPLC BEH C8 (2.1×100 mm, 1.7 m) was used as a column, and the column temperature was 40° C. Acetonitrile was used for Mobile Phase A and a 0.1% aqueous solution of formic acid was used for Mobile Phase B. The amount of injection of the sample was 5.0 μL. The results are shown in the table below.

TABLE 4

| Device 2 | 9mDBtBPNfpr (%) | PCBFF (%) |
|---|---|---|
| n = 1 | 80.2 | 19.8 |
| n = 2 | 80.7 | 19.3 |
| n = 3 | 80.2 | 19.7 |
| n = 4 | 80.6 | 19.4 |
| Reference | 79.6 | 20.4 |
| Remains in evaporation source | 79.7 | 20.3 |

The ratio of 9mDBtBPNfpr to PCBFF in the EL device evaporated using the composition for an EL device of one embodiment of the present invention is almost the same as the composition of the composition for an EL device mixed in advance, and the sample reminded in the evaporation source also had a similar composition. Accordingly, it was found that even when the composition for an EL device of one embodiment of the present invention is repeatedly evaporated, a change in composition hardly occurs in an evaporated film. As a result, it was found that large variations in characteristics of the EL devices manufactured using the composition hardly occur.

Example 2

In this example, an EL device 4 fabricated using the composition for an EL device of one embodiment of the present invention described in Embodiments will be described. Structural Formulae of organic compounds used in this example are shown below.

[Chemical Formula 19]

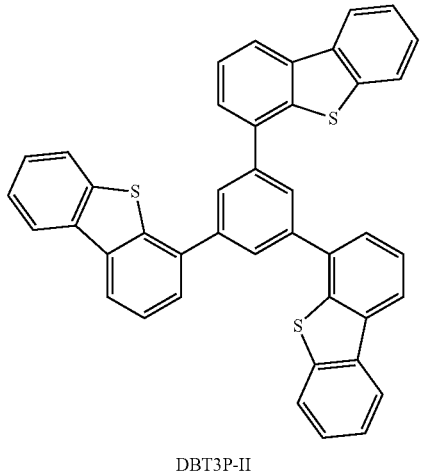

DBT3P-II (i)

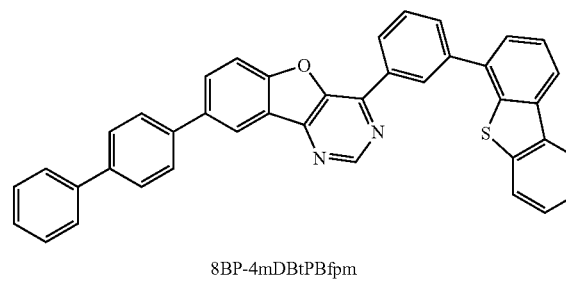

8BP-4mDBtPBfpm (xii)

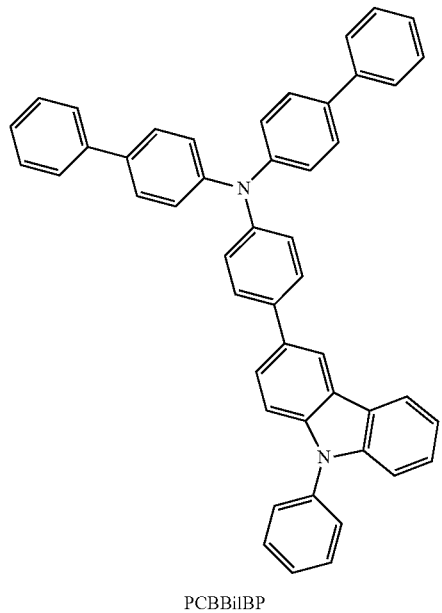

PCBBiIBP (viii)

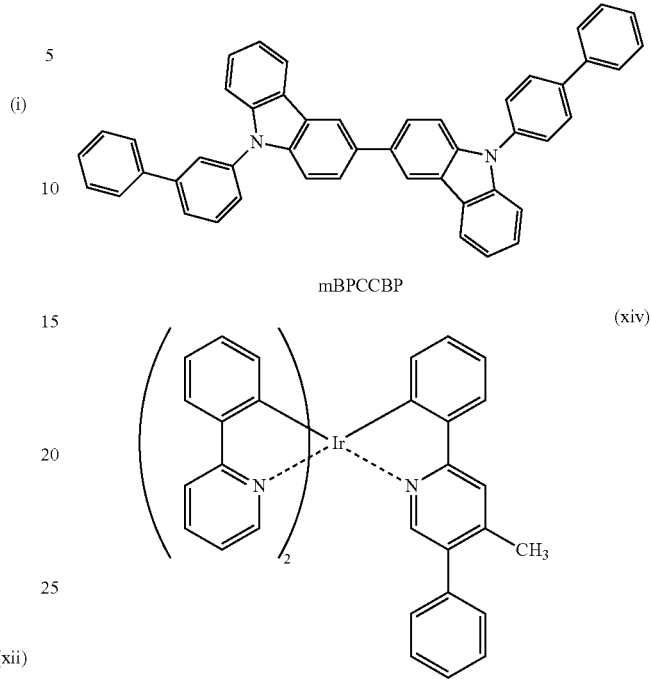

mBPCCBP (xiii)

[Ir(ppy)₂(mdppy)] (xiv)

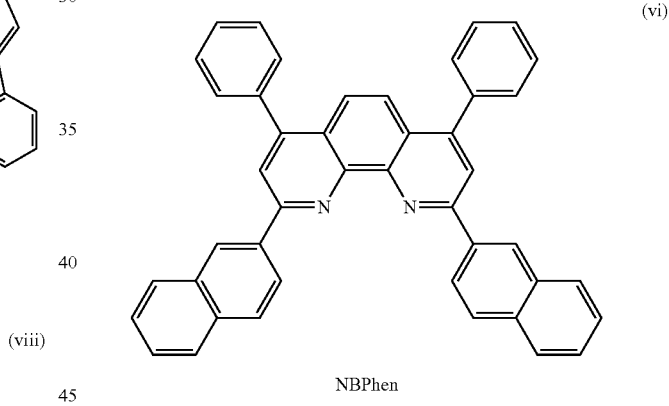

NBPhen (vi)

(Method of fabricating EL Device 4)

First, indium tin oxide containing silicon oxide (ITSO) was deposited on a glass substrate by a sputtering method to form the anode 101. Note that the film thickness was 70 nm and the area of the electrode was 2 mm×2 mm.

Next, in pretreatment for forming the EL device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Then, the substrate on which the anode 101 was formed was fixed to a substrate holder provided in the vacuum evaporation apparatus such that the surface on which the anode 101 was formed faced downward. On the anode 101, 4,4',4''-(benzene-1,3,5-triyl)tri(dibenzothiophene) (abbreviation: DBT3P-II) represented by Structural Formula (i) shown above and molybdenum(VI) oxide were deposited by co-evaporation to a thickness of 45 nm at a weight ratio of 2:1 (=DBT3P-II: molybdenum oxide) by an evaporation method using resistance heating, whereby the hole-injection layer 111 was formed.

Next, over the hole-injection layer 111, 4,4'-diphenyl-4''-(9-phenyl-9H-carbazol-3-yl)triphenylamine (abbreviation: PCBBi1BP) represented by Structural Formula (viii) was deposited by evaporation to a thickness of 20 nm; whereby the hole-transport layer 112 was formed.

Then, a composition in which 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm) represented by Structural Formula (xii) above and 9-(1,1'-biphenyl-3-yl)-9'-(1,1'-biphenyl-4-yl)-9H,9'H-3,3'-bicarbazole (abbreviation: mBPCCBP) represented by Structural Formula (xiii) above are mixed in advance such that the weight ratio of 8BP-4mDBtPBfpm to mBPCCBP was 0.5:0.5 and [2-(4-methyl-5-phenyl-2-pyridinyl-κN)phenyl-xC]bis[2-(2-pyridinyl-κN)phenyl-xC]iridium(III) (abbreviation: [Ir(ppy)$_2$(mdppy)]) represented by Structural Formula (xiv) above were deposited by co-evaporation to a thickness of 40 nm such that the weight ratio of [the composition in which 8BP-4mDBtPBfpm and mBPCCBP are mixed] to [Ir(ppy)$_2$(mdppy)] was 1:0.1, whereby the light-emitting layer 113 was formed. Note that in the case of forming the light-emitting layer 113, 8BP-4mDBtPBfpm and mBPCCBP were evaporated from the same evaporation source as the sample in which 8BP-4mDBtPBfpm and mBPCCBP were mixed in advance.

After that, on the light-emitting layer 113, 8BP-4mDBtPBfpm was deposited by evaporation to a thickness of 20 nm, and 2,9-bis(naphthalen-2-yl)-4,7-diphenyl-1,10-phenanthroline (abbreviation: NBPhen) represented by Structural Formula (vi) above was deposited by evaporation to a thickness of 10 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the cathode 102, whereby the EL device 4 was fabricated.

As the EL devices 4, four devices having the same stacked structure, i.e., n=1 to n=4, were fabricated in such a manner that evaporation for the light-emitting layer was successively performed without changing the sample in the evaporation source.

The device structure of the EL device 4 is listed in the following table.

Here, Table 5 shows measurement results of 5% weight loss temperatures in a vacuum (approximately $1\times10^{-2}$ Pa) of two kinds of organic compounds for a device used as a composition mixed in advance when the light-emitting layer 113 of the EL device 4 was formed by evaporation. The 5% weight loss temperature was obtained from the relation between weight and temperature (thermogravimetric measurement) by performing thermogravimetry-differential thermal analysis (TG-DTA). The measurement was performed using a high vacuum differential type differential thermal balance (TG-DTA2410SA, produced by Bruker AXS K.K.).

TABLE 6

|  |  | 5% weight loss temperature (° C.) | Difference (° C.) |
|---|---|---|---|
| EL device 4 | 8BP-4mDBtPBfpm | 268 | 14 |
|  | mBPCCBP | 282 |  |

As shown in Table 6, a difference in the 5% weight loss temperature between the organic compounds contained in the composition of the sample mixed in advance, which were used for fabricating the EL device 4, was 14° C.

The EL device 4 was subjected to sealing with a glass substrate (a sealant was applied to surround the device, and at the time of sealing, UV treatment was performed first and heat treatment was performed at 80° C. for an hour) in a glove box containing a nitrogen atmosphere so that the EL device was not exposed to the air. Then, the initial characteristics and reliability were measured. Note that the measurement method is similar to that in Example 1.

Figure 33:
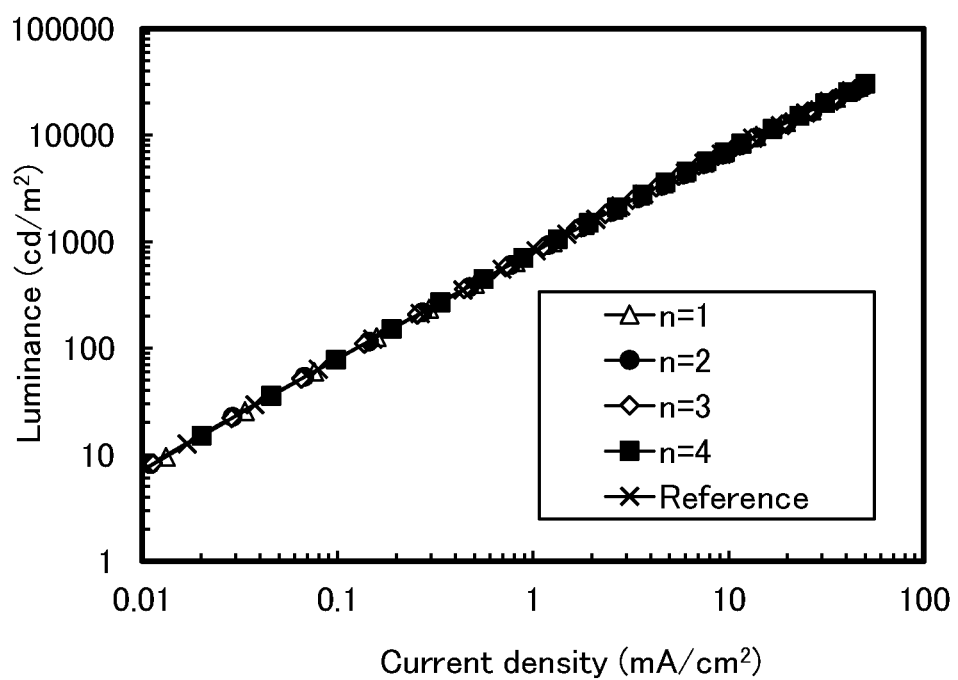
FIG. 33 is a graph showing luminance-current density characteristics of EL devices 4.
Figure 34:
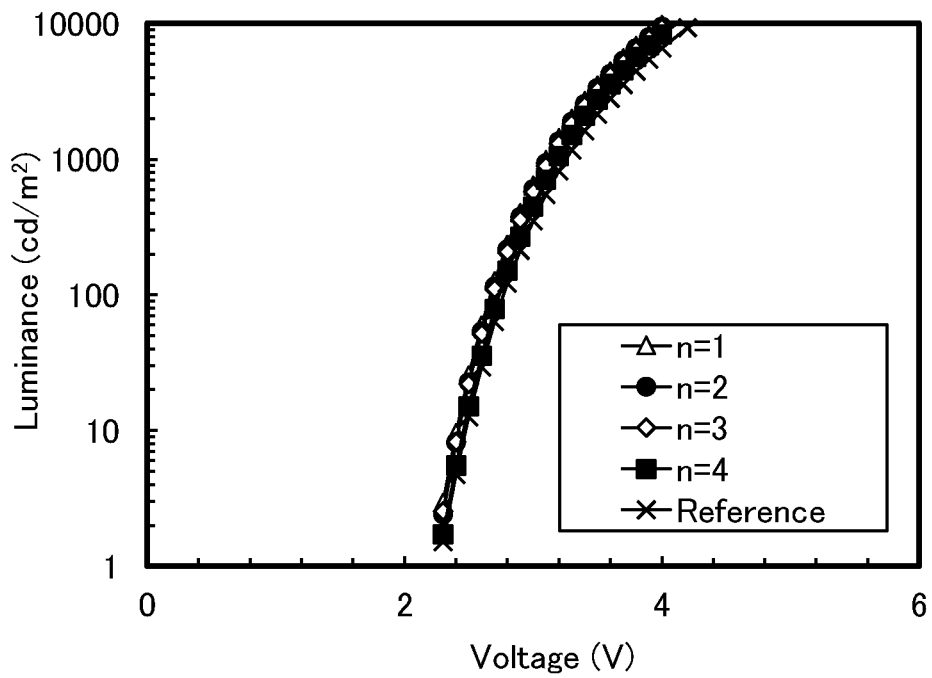
FIG. 34 is a graph showing luminance-voltage characteristics of the EL devices 4.
Figure 35:
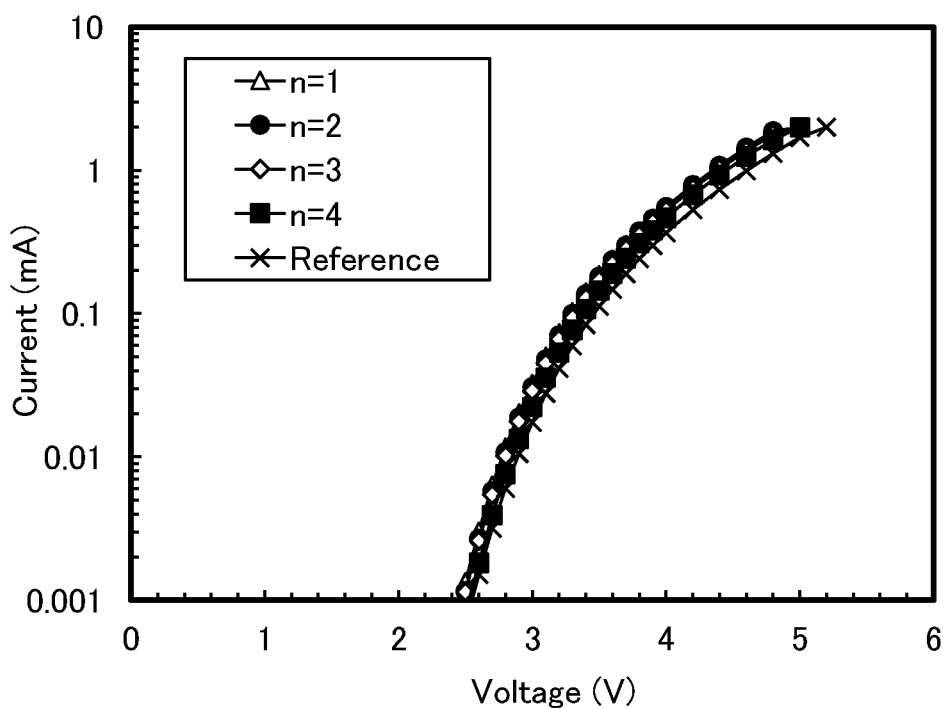
FIG. 35 is a graph showing current-voltage characteristics of the EL devices 4.
Figure 36:
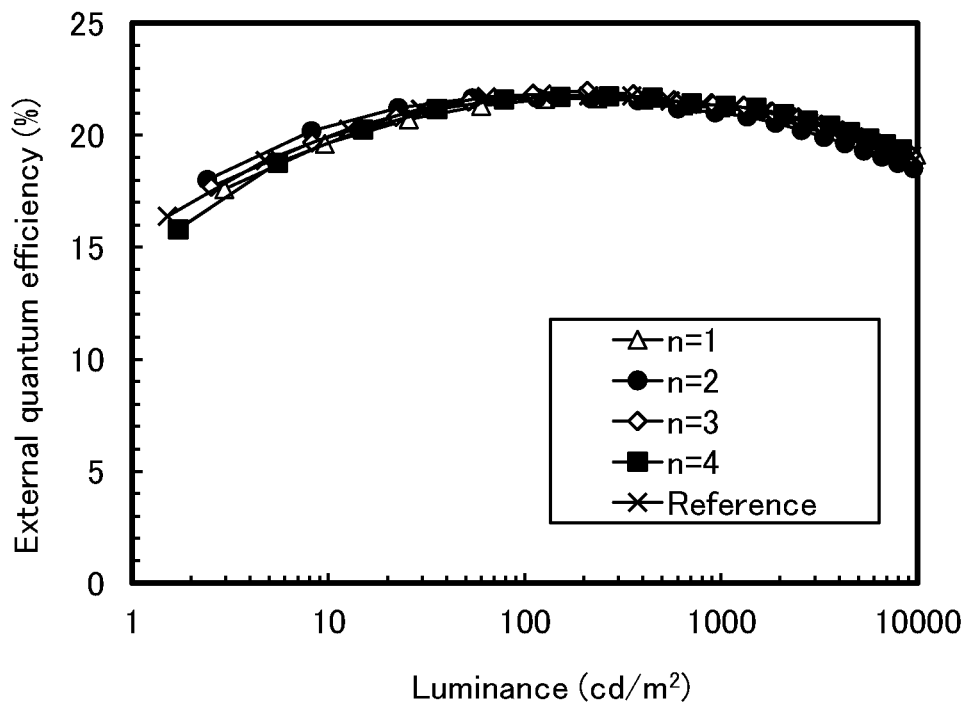
FIG. 36 is a graph showing external quantum efficiency-luminance characteristics of the EL device 4.
Figure 37:
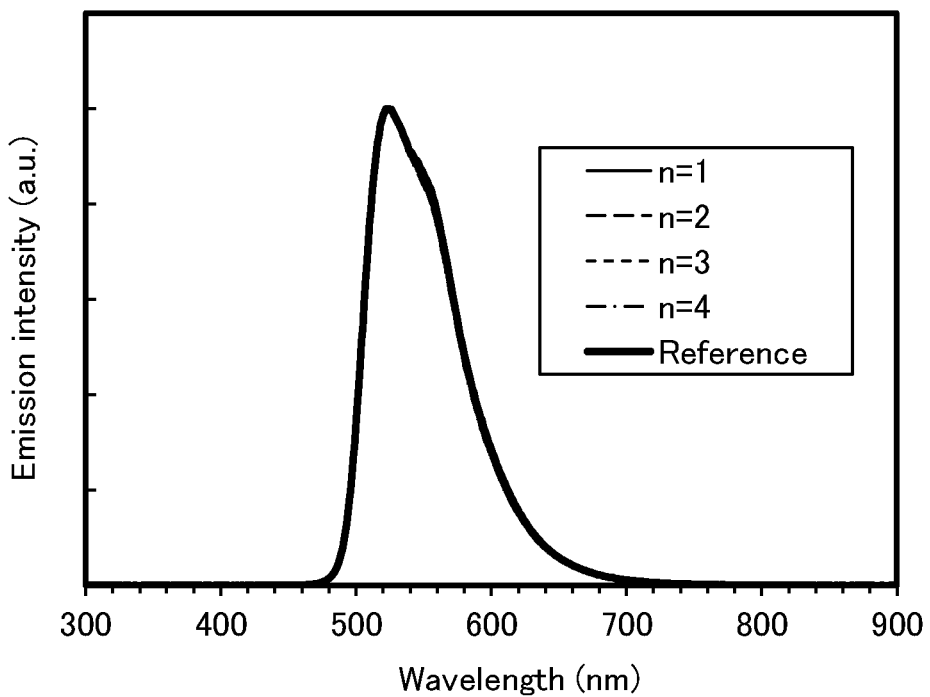
FIG. 37 is a graph showing emission spectra of the EL devices 4.

FIG. 33 shows the luminance-current density characteristics; FIG. 34, the luminance-voltage characteristics; FIG. 35, the current-voltage characteristics; FIG. 36, the external quantum efficiency-luminance characteristics; and FIG. 37, the emission spectra.

The following table shows the main characteristics of the EL device 4 at a luminance of approximately 1000 cd/cm². In addition to the characteristics of the above-described devices, the table also shows the characteristics of a reference device for which evaporation was performed using different evaporation sources.

TABLE 5

|  | Hole-injection layer 45 nm | Hole-transport layer 20 nm | Light-emitting layer 40 nm | Electron-transport layer | | Electron-injection layer 1 nm |
|---|---|---|---|---|---|---|
|  |  |  |  | 1 20 nm | 2 15 nm |  |
| EL device 4 | DBT3P-II: MoOx (2:1) | PCBBi1BP | *4 | 8BP-4mDBtPBfpm | NBPhen | LiF |

*4 8BP-4mDBtPBfpm:mBPCCBP: [Ir(ppy)$_2$(mdppy)] (0.5:0.5:0.10)

TABLE 7

| | Voltage (V) | Current (mA) | Current density (mA/cm²) | Chromaticity x | Chromaticity y | Current efficiency (cd/A) | External quantum efficiency (%) |
|---|---|---|---|---|---|---|---|
| 4 n = 1 | 3.1 | 0.05 | 1.3 | 0.34 | 0.63 | 78.6 | 21.2 |
| n = 2 | 3.1 | 0.05 | 1.2 | 0.34 | 0.63 | 77.8 | 21.0 |
| n = 3 | 3.1 | 0.05 | 1.1 | 0.34 | 0.63 | 79.3 | 21.4 |
| n = 4 | 3.2 | 0.05 | 1.3 | 0.33 | 0.63 | 78.8 | 21.3 |
| Reference | 3.3 | 0.06 | 1.5 | 0.34 | 0.63 | 78.6 | 21.3 |

It was found from FIG. 33 to FIG. 37 and Table 7 that the EL devices 4 had comparably favorable initial characteristics.

Figure 38:
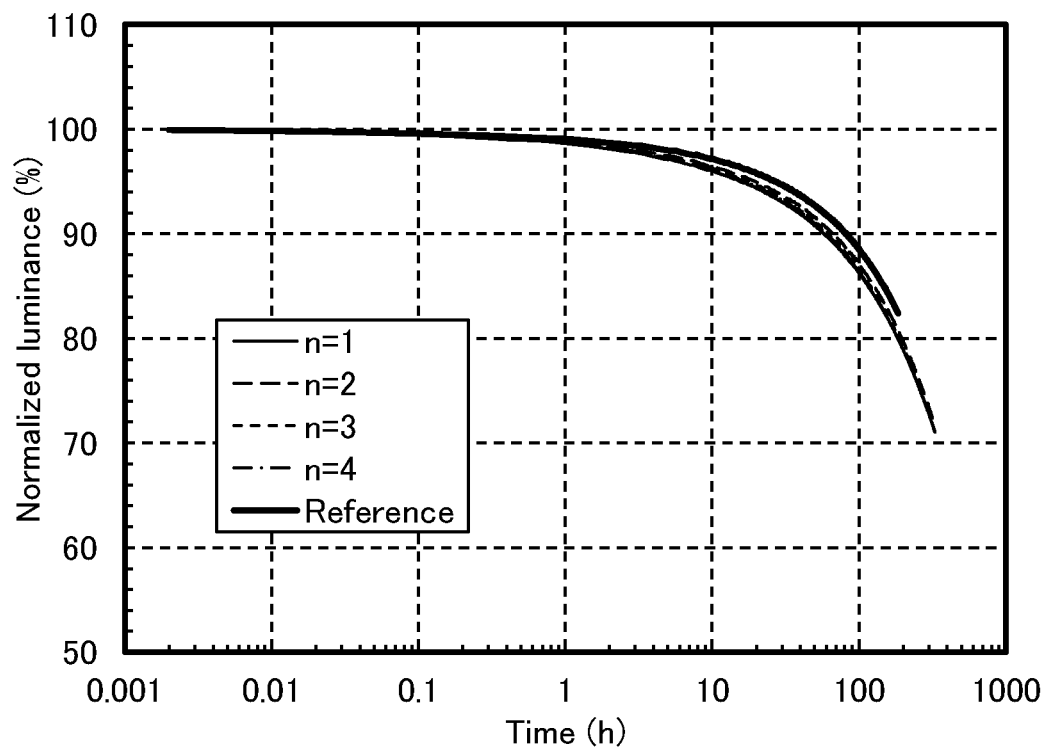
FIG. 38 is a graph showing luminance-time change characteristics of the EL devices 4.

FIG. 38 is a graph showing a change in luminance over driving time at a current density of 50 mA/cm². FIG. 38 shows that the EL devices have comparably favorable lifetimes.

It was found from FIG. 38 that the EL devices 4, which were manufactured with use of the compositions of one embodiment of the present invention in each of which the 5% weight loss temperature in high vacuum between the two kinds of materials in the composition serving as an evaporation sample is 50° C. or lower, are EL devices whose deterioration in characteristics and lifetime due to repeated evaporation is small.

Reference Example

Since 9mDBtBPNfpr, 8(βN2)-4mDBtPBfpm, and 8BP-4mDBtPBfpm used in Examples are undisclosed substances, the synthesis methods thereof will be described.

Synthesis Method of 9mDBtBPNfpr

A synthesis method of 9-[(3'-dibenzothiophen-4-yl)biphenyl-3-yl]naphtho[1',2':4,5]furo[2,3-b]pyrazine (abbreviation: 9mDBtBPNfpr), which is represented by Structural Formula (iii) in Example 1, is described. The structure of 9mDBtBPNfpr is shown below.

[Chemical Formula 20]

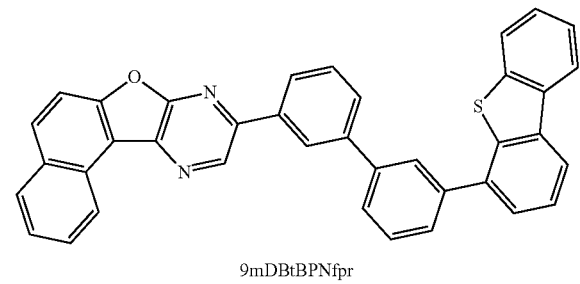

9mDBtBPNfpr

Step 1: Synthesis of 6-chloro-3-(2-methoxynaphthalen-1-yl)pyrazin-2-amine

First, into a three-neck flask equipped with a reflux pipe were put 4.37 g of 3-bromo-6-chloropyrazin-2-amine, 4.23 g of 2-methoxynaphthalene-1-boronic acid, 4.14 g of potassium fluoride, and 75 mL of dehydrated tetrahydrofuran, and the air in the flask was replaced with nitrogen. The mixture in the flask was degassed by being stirred under reduced pressure, 0.57 g of tris(dibenzylideneacetone)dipalladium (0) (abbreviation: Pd₂(dba)₃) and 4.5 mL of tri-tert-butylphosphine (abbreviation: t-Bu₃P) were added thereto, and then stirring was performed at 80° C. for 54 hours for reaction.

After a predetermined time elapsed, the obtained mixture was subjected to suction filtration and the filtrate was concentrated. Then, purification by silica gel column chromatography using a developing solvent of toluene:ethyl acetate=9:1 was performed, whereby a target pyrazine derivative was obtained (yellowish white powder, 2.19 g, in a yield of 36%). The synthesis scheme of Step 1 is shown below.

[Chemical Formula 21]

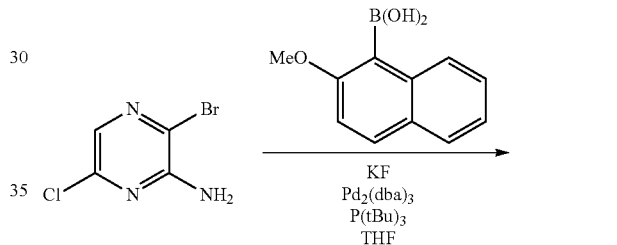

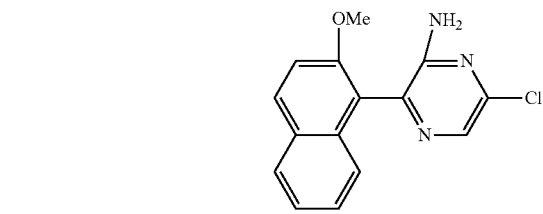

Step 2: Synthesis of 9-chloronaphtho[1',2':4,5]furo[2,3-b]pyrazine

Next, into a three-neck flask were put 2.18 g of 6-chloro-3-(2-methoxynaphthalen-1-yl)pyrazin-2-amine obtained in Step 1, 63 mL of dehydrated tetrahydrofuran, and 84 mL of a glacial acetic acid, and the air in the flask was replaced with nitrogen. After the flask was cooled down to −10° C., 2.8 mL of tert-butyl nitrite was dripped, and stirring was performed at −10° C. for 30 minutes and at 0° C. for 3 hours. After a predetermined time elapsed, 250 mL of water was added to the obtained suspension and suction filtration was performed, whereby a target pyrazine derivative was obtained (yellowish white powder, 1.48 g, in a yield of 77%). The synthesis scheme of Step 2 is shown below.

[Chemical Formula 22]

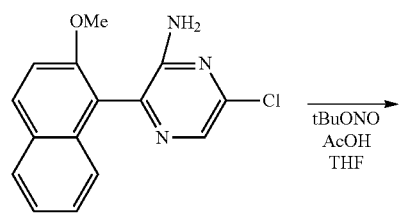

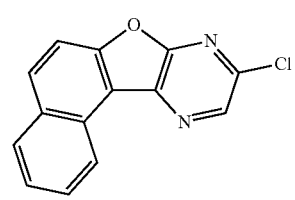

Step 3: Synthesis of 9-[(3'-dibenzothiophene-4-yl)biphenyl-3-yl]naphtho[1',2':4,5]furo[2,3-b]pyrazine (abbreviation: 9mDBtBPNfpr)

Into a three-neck flask were put 1.48 g of 9-chloronaphtho[1',2':4,5]furo[2,3-b]pyrazine obtained in Step 2, 3.41 g of 3'-(4-dibenzothiophene)-1,1'-biphenyl-3-boronic acid, 8.8 mL of a 2M aqueous solution of potassium carbonate, 100 mL of toluene, and 10 mL of ethanol, and the air in the flask was replaced with nitrogen. The mixture in the flask was degassed by being stirred under reduced pressure, 0.84 g of bis(triphenylphosphine)palladium(II) dichloride (abbreviation: $PdCl_2(PPh_3)_2$) was added thereto, and then stirring was performed at 80° C. for 18 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with a mixed solvent of toluene and hexane, whereby a target substance was obtained (a pale yellow solid, 2.66 g, in a yield of 82%).

By a train sublimation method, 2.64 g of the obtained pale yellow solid was purified by sublimation. The conditions of the purification by sublimation were such that the solid was heated under a pressure of 2.6 Pa at 315° C. while the argon gas flowed at a flow rate of 15 mL/min. After the purification by sublimation, 2.34 g of a target pale yellow solid was obtained in a yield of 89%. The synthesis scheme of Step 3 is shown below.

[Chemical Formula 23]

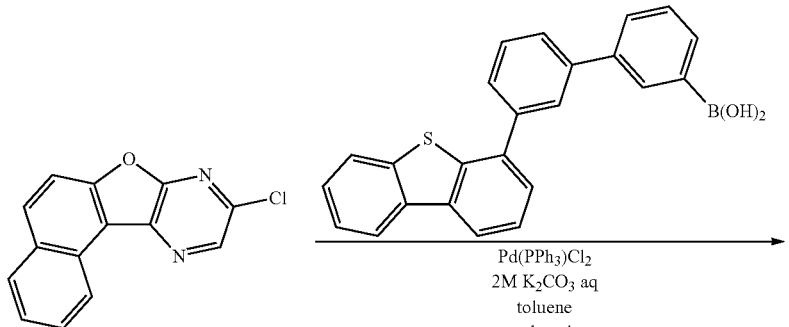

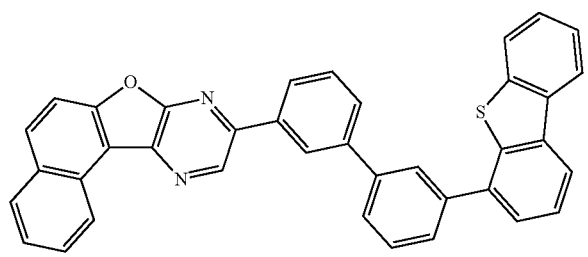

9mDBtBPNfpr

Results of analysis by nuclear magnetic resonance ($^1$H-NMR) spectroscopy of the pale yellow solid obtained in Step 3 are shown below. The results reveal that 9mDBtBPNfpr was obtained.

$^1$H-NMR. δ (CD$_2$Cl$_2$): 7.47-7.51 (m, 2H), 7.60-7.69 (m, 5H), 7.79-7.89 (m, 6H), 8.05 (d, 1H), 8.10-8.11 (m, 2H), 8.18-8.23 (m, 3H), 8.53 (s, 1H), 9.16 (d, 1H), 9.32 (s, 1H).

Synthesis Method of 8(βN2)-4mDBtBPBfpm

A synthesis method of 8-[(2,2'-binaphthalen)-6-yl]-4-[3-(dibenzothiophen-4-yl)phenyl]-[1]benzofuro[3,2-d]pyrimidine (abbreviation: 8(βN2)-4mDBtPBfpm), which is represented by Structural Formula (ix) in Example 1, is described. The structure of 8(βN2)-4mDBtPBfpm is shown below.

[Chemical Formula 24]

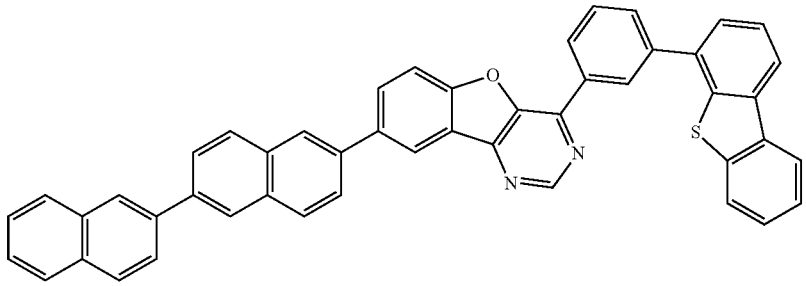

8(βN2)-4mDBtPBfpm

Synthesis of 8-[(2,2'-binaphthalen)-6-yl]-4-[3-(dibenzothiophen-4-yl)phenyl]-[1]benzofuro[3,2-d]pyrimidine Into a three-neck flask, 1.21 g of 8-chloro-4-[3-(dibenzothiophen-4-yl)phenyl]-[1]benzofuro[3,2-d]pyrimidine, 0.857 g of [2,2'-binaphthalen]-6-ylboronic acid, 1.67 g of tripotassium phosphate, 26 mL of diglyme, and 0.583 g of t-butanol were put, the mixture in the flask was degassed by being stirred under reduced pressure, and the air in the flask was replaced with nitrogen.

This mixture was heated to 60° C. and 18.9 mg of palladium(II) acetate and 61.1 mg of di(1-adamantyl)-n-butylphosphine were added, followed by stirring at 120° C. for 10 hours. Water was added to this reaction liquid, suction filtration was performed, and the obtained residue was washed with water, ethanol, and toluene. This residue was dissolved in heated toluene, followed by filtration through a filter aid filled with Celite, alumina, and Celite in this order. The obtained solution was concentrated and dried to give a white solid.

Into a three-neck flask, all of the obtained solid, 0.348 g of [2,2'-binaphthalen]-6-ylboronic acid, 0.621 g of tripotassium phosphate, 13 mL of diglyme, and 0.239 g of t-butanol were put, they were degassed by being stirred under reduced pressure, and the air in the flask was replaced with nitrogen. This mixture was heated to 60° C. and 8.7 mg of palladium(II) acetate and 25.1 mg of di(1-adamantyl)-n-butylphosphine were added, followed by stirring at 120° C. for 18.5 hours. Water was added to this reaction liquid, suction filtration was performed, and the obtained residue was washed with water, ethanol, and toluene.

This residue was dissolved in heated toluene, followed by filtration through a filter aid filled with Celite, alumina, and Celite in this order. The obtained solution was concentrated and dried, and then recrystallized with toluene to give 1.16 g of a target white solid in a yield of 65%. By a train sublimation method, 1.15 g of the obtained white solid was sublimated and purified. The conditions of the sublimation purification were such that the solid was heated under a pressure of 2.64 Pa at 365° C. while the argon gas flowed at a flow rate of 10 mL/min. After the sublimation purification, 0.958 g of 8(βN2)-4mDBtPBfpm was obtained (a collection rate was 83%, a white solid). The synthesis scheme is shown below.

[Chemical Formula 25]

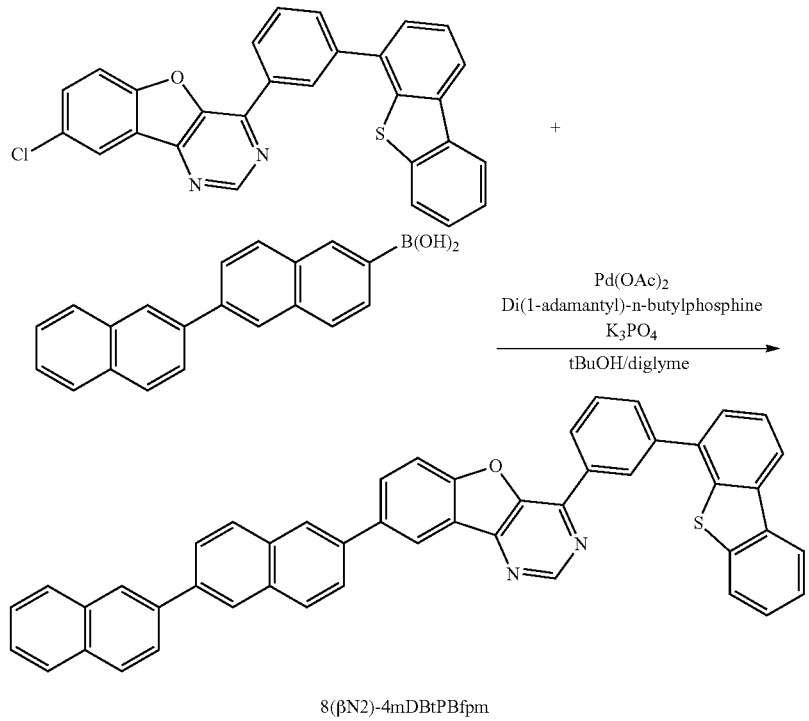

8(βN2)-4mDBtPBfpm

Note that analysis results by nuclear magnetic resonance ($^1$H-NMR) spectroscopy of the white solid obtained by the above-described reaction are shown below. The results reveal that 8(βN2)-4mDBtPBfpm was obtained.

$^1$H-NMR. δ (CDCl$_3$): 7.50-7.7.57 (m, 4H), 7.64-7.67 (m, 2H), 7.82 (t, 1H), 7.86-8.00 (m, 9H), 8.05-8.09 (m, 2H), 8.14 (d, 1H), 8.22-8.26 (m, 5H), 8.69 (s, 1H), 8.74 (d, 1H), 9.07 (s, 1H), 9.35 (s, 1H).

Synthesis Method of 8BP-4mDBtPBfpm

A synthesis method of 8-(1,1'-biphenyl-4-yl)-4-[3-(dibenzothiophen-4-yl)phenyl]-[1]benzofuro[3,2-d]pyrimidine (abbreviation: 8BP-4mDBtPBfpm), which is represented by Structural Formula (xii) in Example 2, is described. The structure of 8BP-4mDBtPBfpm is shown below.

[Chemical Formula 26]

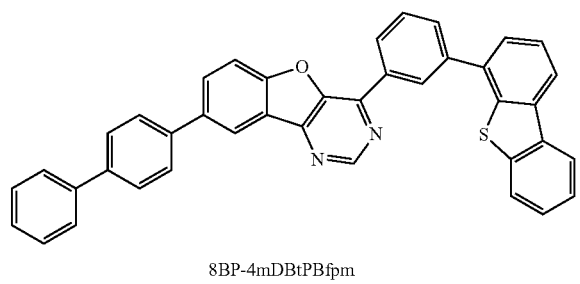

8BP-4mDBtPBfpm

Synthesis of 8-(1,1'-biphenyl-4-yl)-4-[3-(dibenzothiophen-4-yl)phenyl]-[1]benzofuro[3,2-d]pyrimidine Into a three-neck flask, 1.37 g of 8-chloro-4-[3-(dibenzothiophen-4-yl)phenyl]-[1]benzofuro[3,2-d]pyrimidine, 0.657 g of 4-biphenylboronic acid, 1.91 g of tripotassium phosphate, 30 mL of diglyme, and 0.662 g of t-butanol were put, the mixture in the flask was degassed by being stirred under reduced pressure, and the air in the flask was replaced with nitrogen.

This mixture was heated to 60° C. and 23.3 mg of palladium(II) acetate and 66.4 mg of di(1-adamantyl)-n-butylphosphine were added, followed by stirring at 120° C. for 27 hours. Water was added to this reaction liquid, suction filtration was performed, and the obtained residue was washed with water, ethanol, and toluene. This residue was dissolved in heated toluene, followed by filtration through a filter aid filled with Celite, alumina, and Celite in this order. The obtained solution was concentrated and dried to give a white solid. The obtained solution was concentrated and dried, and then recrystallized with toluene to give 1.28 g of a target white solid in a yield of 74%.

By a train sublimation method, 1.26 g of the white solid was sublimated and purified. The conditions of the sublimation purification were such that the solid was heated under a pressure of 2.56 Pa at 310° C. while the argon gas flowed at a flow rate of 10 mL/min. After the sublimation purification, 1.01 g of a target pale yellow solid was obtained at a collection rate of 80%. The synthesis scheme is shown below.

[Chemical Formula 27]

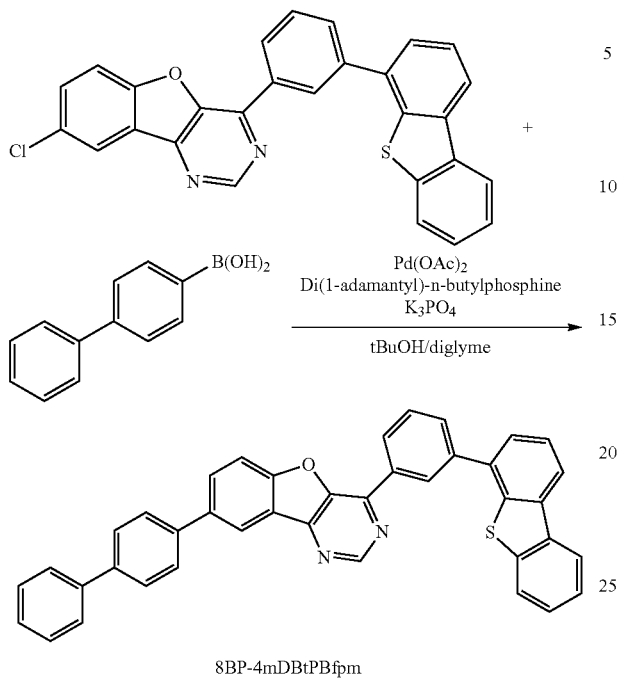

Analysis results by nuclear magnetic resonance ($^1$H-NMR) spectroscopy of the pale yellow solid obtained in the above reaction are shown below. The results reveal that 8BP-4mDBtPBfpm was obtained.

$^1$H-NMR. δ (CDCl$_3$): 7.39 (t, 1H), 7.47-7.53 (m, 4H), 7.63-7.67 (m, 2H), 7.68 (d, 2H), 7.75 (d, 2H), 7.79-7.83 (m, 4H), 7.87 (d, 1H), 7.98 (d, 1H), 8.02 (d, 1H), 8.23-8.26 (m, 2H), 8.57 (s, 1H), 8.73 (d, 1H), 9.05 (s, 1H), 9.34 (s, 1H).

REFERENCE NUMERALS

1: anode, 102: cathode 103: EL layer, 104: cap layer, 111: hole-injection layer, 112: hole-transport layer, 113: light-emitting layer, 114: electron-transport layer, 115: electron-injection layer, 116: charge-generation layer, 117: p-type layer, 118: electron-relay layer, 119: electron-injection buffer layer, 400: substrate, 401: anode, 403: EL layer, 404: cathode, 405: sealing material, 406: sealing material, 407: sealing substrate, 408: space, 412: pad, 420: IC chip, 501: anode, 502: cathode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealing material, 607: space, 608: wiring, 609: FPC (flexible printed circuit), 610: element substrate, 611: switching FET, 612: current controlling FET, 613: anode, 614: insulator, 616: EL layer, 617: cathode, 618: EL device, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: anode, 1024R: anode, 1024G: anode, 1024B: anode, 1025: partition wall, 1028: EL layer, 1029: cathode, 1031: sealing substrate, 1032: sealing material, 1033: transparent base material, 1034R: red coloring layer, 1034G: green coloring layer, 1034B: blue coloring layer, 1035: black matrix, 1036: overcoat layer, 1037: third interlayer insulating film, 1040: pixel portion, 1041: driver circuit portion, 1042: peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: second display portion, 5003: speaker, 5004: LED lamp, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153: bend portion, 5120: dust, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 9310: portable information terminal, 9311: display panel, 9312: display region, 9313: hinge, 9315: housing.

The invention claimed is:
1. A composition for an EL device comprising:
a first organic compound; and
a second organic compound,
wherein a difference in the 5% weight loss temperature between the first organic compound and the second organic compound measured by thermogravimetry under a pressure of 0.1 Pa or lower is less than or equal to 50° C.,
wherein the first organic compound has a benzofurodiazine skeleton or a benzothiodiazine skeleton, and
wherein the second organic compound has a carbazole skeleton.
2. The composition for an EL device according to claim 1,
wherein the first organic compound has any one of a naphthofuropyrazine skeleton, a phenanthrofuropyrazine skeleton, a naphthothiopyrazine skeleton, and a phenanthrothiopyrazine skeleton.
3. The composition for an EL device according to claim 1,
wherein the first organic compound is represented by General Formula (G1):

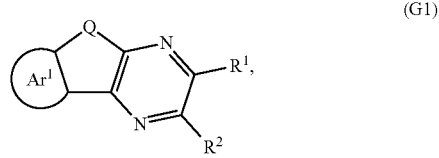

wherein Q represents oxygen or sulfur,
wherein Ar$^1$ represents a substituted or unsubstituted condensed aromatic ring, wherein one of R¹ and R² represents hydrogen and the other represents a group having 1 to 100 carbon atoms in total, and
wherein the group has a hole-transport property skeleton.

4. The composition for an EL device according to claim 1,
wherein the first organic compound is represented by Structural Formula (100):

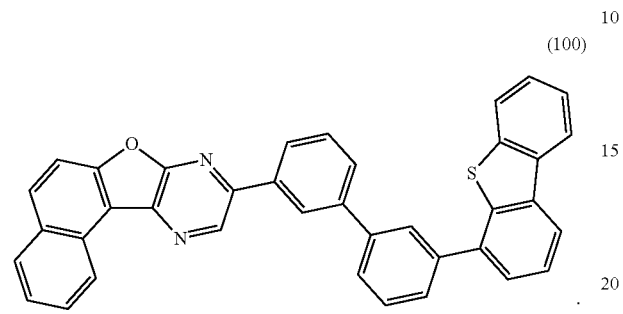
(100)

5. The composition for an EL device according to claim 1,
wherein the first organic compound has a benzofuropyrimidine skeleton or a benzothiopyrimidine skeleton.

6. The composition for an EL device according to claim 1,
wherein the first organic compound is represented by General Formula (G2);

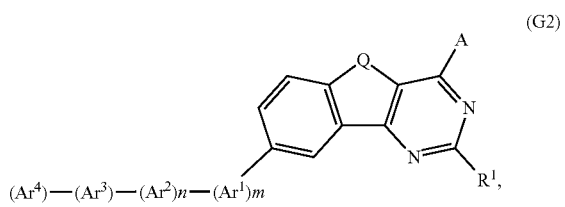
(G2)

wherein Q represents oxygen or sulfur; each of Ar¹, Ar², Ar³, and Ar⁴ independently represents a substituted or unsubstituted aromatic hydrocarbon ring; a substituent of the aromatic hydrocarbon ring represents any one of an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group; and the number of carbon atoms included in the aromatic hydrocarbon ring is greater than or equal to 6 and less than or equal to 25,
wherein each of m and n independently represents 0 or 1,
wherein A represents a group having 12 to 100 carbon atoms in total and includes one or more of a benzene ring, a naphthalene ring, a fluorene ring, a phenanthrene ring, a triphenylene ring, a dibenzothiophene ring, a dibenzofuran ring, a carbazole ring, a benzimidazole ring, and a triphenylamine structure, and
wherein R¹ represents hydrogen, an alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, a substituted or unsubstituted aryl group having 6 to 13 carbon atoms, or a substituted or unsubstituted heteroaryl group having 3 to 12 carbon atoms.

7. The composition for an EL device according to claim 1,
wherein the first organic compound is represented by Structural Formula (200) or (201):

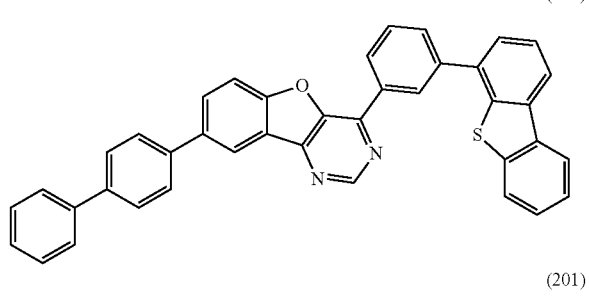
(200)

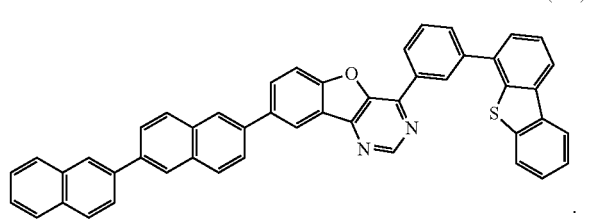
(201)

8. The composition for an EL device according to claim 1,
wherein the second organic compound has a bicarbazole skeleton.

9. The composition for an EL device according to claim 8,
wherein two carbazolyl groups in the bicarbazole skeleton are bonded to each other at any of the 2-position to the 4-position.

10. The composition for an EL device according to claim 1,
wherein the second organic compound further has a triarylamine skeleton.

11. The composition for an EL device according to claim 10,
wherein a nitrogen atom in the triarylamine and the carbazole skeleton are bonded through a phenylene group.

12. The composition for an EL device according to claim 10,
wherein the carbazole skeleton is bonded at any one of the 2-position, the 3-position, the 4-position, and the 9-position.

13. The composition for an EL device according to claim 1,
wherein the second organic compound has at least one fluorene skeleton.

14. The composition for an EL device according to claim 1,
wherein the first organic compound and the second organic compound are a combination that forms an exciplex.

15. The composition for an EL device according to claim 1,
wherein the difference in the 5% weight loss temperature is less than or equal to 40° C.

16. The composition for an EL device according to claim 1,
wherein the difference in the 5% weight loss temperature is less than or equal to 30° C.

17. A composition for an EL device comprising:
a first organic compound; and
a second organic compound,
wherein a difference in the 5% weight loss temperature between the first organic compound and the second organic compound measured by thermogravimetry under a pressure of 0.1 Pa or lower is less than or equal to 50° C.,
wherein the first organic compound has any one of a naphthofuropyrazine skeleton, a phenanthrofuropyrazine skeleton, a naphthothiopyrazine skeleton, and a phenanthrothiopyrazine skeleton, and
wherein the second organic compound has a triarylamine.

18. The composition for an EL device according to claim 17,
wherein the first organic compound is represented by General Formula (G1):

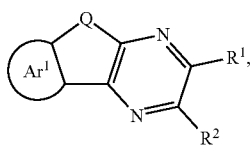

(G1)

wherein Q represents oxygen or sulfur,
wherein Ar¹ represents a substituted or unsubstituted condensed aromatic ring,
wherein one of $R^1$ and $R^2$ represents hydrogen and the other represents a group having 1 to 100 carbon atoms in total, and
wherein the group has hole-transport property skeleton.

19. The composition for an EL device according to claim 17,
wherein the first organic compound is represented by Structural Formula (100):

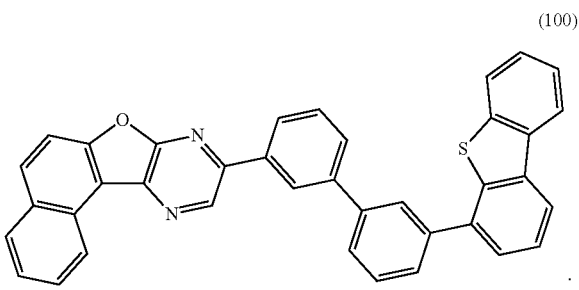 [SMILES: c1cc(-c2cccc(-c3cccc4c3sc3ccccc34)c2)cc(-c2cnc3c(n2)oc2ccc4ccccc4c23)c1]

(100)

20. The composition for an EL device according to claim 17,
wherein the second organic compound has at least one of fluorene skeleton.

21. The composition for an EL device according to claim 17,
wherein the first organic compound and the second organic compound are a combination that forms an exciplex.

* * * * *